(12) United States Patent
Almansa-Rosales et al.

(10) Patent No.: US 11,236,110 B2
(45) Date of Patent: Feb. 1, 2022

(54) SALTS OF (R)-9-(2,5-DIFLUOROPHENETHYL)-4-ETHYL-2-METHYL-1-OXA-4,9-DIAZASPIRO[5.5]UNDECAN-3-ONE

(71) Applicant: ESTEVE PHARMACEUTICALS, S.A., Barcelona (ES)

(72) Inventors: Carmen Almansa-Rosales, Barcelona (ES); Nicolas Tesson, Barcelona (ES)

(73) Assignee: ESTEVE PHARMACEUTICALS, S.A., Barcelona (ES)

( * ) Notice: Subject to any disclaimer, the term of this patent is extended or adjusted under 35 U.S.C. 154(b) by 0 days.

(21) Appl. No.: 16/649,824

(22) PCT Filed: Oct. 16, 2018

(86) PCT No.: PCT/EP2018/000470
§ 371 (c)(1),
(2) Date: Mar. 23, 2020

(87) PCT Pub. No.: WO2019/076475
PCT Pub. Date: Apr. 25, 2019

(65) Prior Publication Data
US 2020/0331929 A1 Oct. 22, 2020

(30) Foreign Application Priority Data
Oct. 17, 2017 (EP) .................................. 17382695

(51) Int. Cl.
*A61K 31/5386* (2006.01)
*A61P 29/00* (2006.01)
*C07D 498/10* (2006.01)

(52) U.S. Cl.
CPC ........ *C07D 498/10* (2013.01); *C07B 2200/13* (2013.01)

(58) Field of Classification Search
CPC ... A61K 31/5386; A61P 29/00; C07D 498/10; C07B 2200/13
See application file for complete search history.

(56) References Cited

U.S. PATENT DOCUMENTS

| | | | |
|---|---|---|---|
| 4,353,900 A | 10/1982 | Clark | |
| 6,114,541 A | 9/2000 | Abrecht | |
| 8,168,783 B2 | 5/2012 | Kokubo et al. | |
| 10,246,465 B2 * | 4/2019 | Virgili-Bernado ... | C07D 498/10 |
| 2009/0105290 A1 | 4/2009 | Sundermann et al. | |
| 2010/0120841 A1 | 5/2010 | Nakano et al. | |
| 2012/0264749 A1 | 10/2012 | Hadida-Ruah | |
| 2017/0101420 A1 | 4/2017 | Virgili-Bernado et al. | |
| 2017/0197984 A1 | 7/2017 | Virgili-Bernado et al. | |
| 2019/0177337 A1 * | 6/2019 | Virgili-Bernado ...... | A61P 25/04 |

FOREIGN PATENT DOCUMENTS

| | | |
|---|---|---|
| DE | 102005030051 | 12/2006 |
| EP | 0 061 333 | 9/1982 |
| EP | 1982714 | 10/2008 |
| WO | WO 2008/105497 | 9/2008 |
| WO | WO 2008/155132 | 12/2008 |
| WO | WO 2009/032667 | 3/2009 |
| WO | WO 2009/098448 | 8/2009 |
| WO | WO 2012/156693 | 11/2012 |
| WO | WO 2015/017305 | 2/2015 |
| WO | WO 2015/185209 | 12/2015 |

OTHER PUBLICATIONS

Bornot et al., J. Med. Chem, 2013, 56, 1197-1210.
Dickenson, et al., Eur J Pain 9, 113-116 (2005).
Bastin, Richard, J., et al., "Salt selection and optimization procedures for pharmaceutical new chemical entities", Organic Process Research & Development, 4, 2000, pp. 427-435.
Caira, Mino, R., "Crystalline polymorphism of organic compounds", Topics in Current Chemistry, 198, 1998, pp. 163-208.
Chien, et al., Neuroscience Letters, 1995, 190, pp. 137-139.
Clark, Robin D., Journal of Medicinal Chemistry, vol. 26, No. 6, p. 855-861, Jan. 1, 1983.
Database Registry, XP-002730855, Chemical Abstracts, May 12, 2010, Accession No. 1222524-76-6.
Friedman, et al., Angew. Chem. Int. Ed. 2013, 52, pp. 9755-9758.
Goldberg, et al., BMC Public Health, 11, 770 (2011).
International Search Report for PCT/EP2015/001115 dated Jun. 23, 2015.
International Search Report for PCT/EP2018/000470 dated Dec. 4, 2018.
Kato, et al., Bioorganic & Medicinal Chemistry Letters, 2014, 24, 565-570.
Mao, et al., J. Pain 12, 157-166 (2011).
Stocks, et al., Bioorganic & Medicinal Chemistry Letters, 2010, 20, 7458-7461.
Turk, et al., Lancet 377, 2226-2235 (2011).
Zamanillo, et al., Eur. J. Pharmacol, 716, 78-93 (2013).

* cited by examiner

*Primary Examiner* — Brenda L Coleman
(74) *Attorney, Agent, or Firm* — Hueschen and Sage

(57) ABSTRACT

The present invention relates to (R)-9-(2,5-difluorophenethyl)-4-ethyl-2-methyl-1-oxa-4,9-diazaspiro[5.5]undecan-3-one salts, to pharmaceutical compositions comprising them, and to their use in therapy and/or prophylaxis of sigma receptor and/or µ-opioid receptor associated disease.

10 Claims, 42 Drawing Sheets

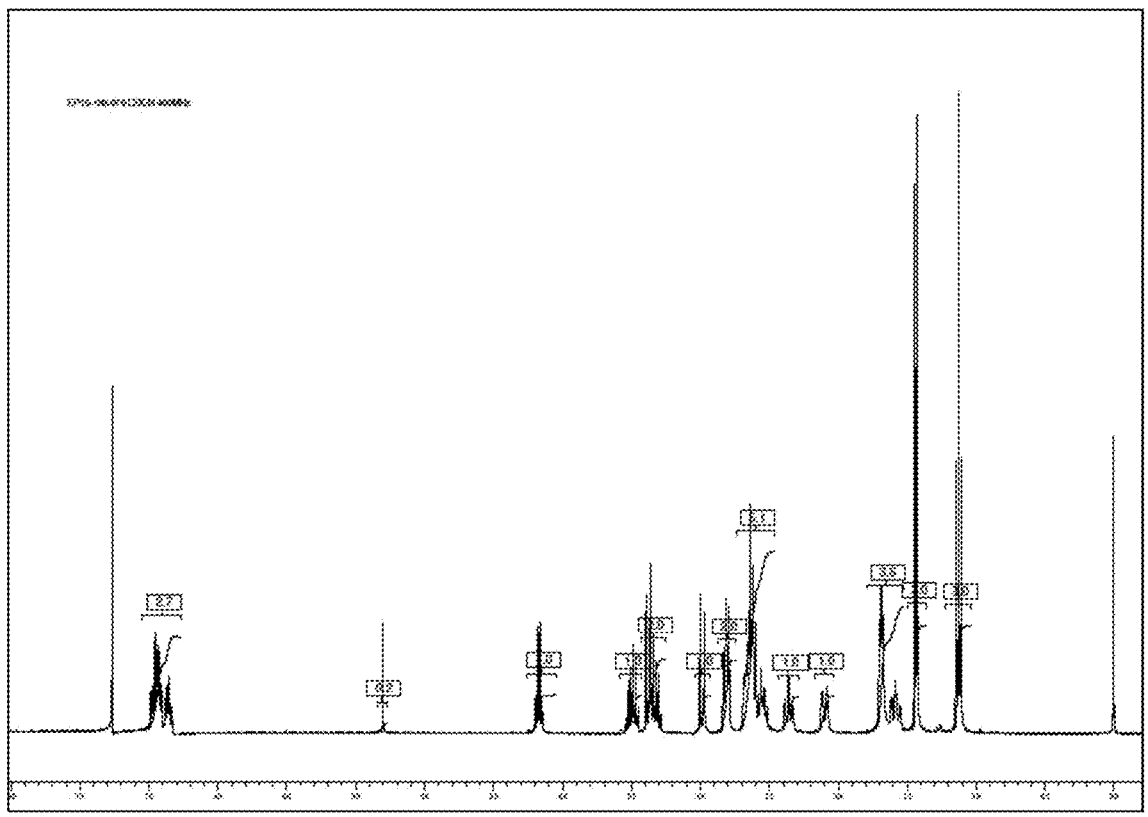
Figure 1. $^1$H-NMR of (R)-9-(2,5-difluorophenethyl)-4-ethyl-2-methyl-1-oxa-4,9-diazaspiro[5.5]undecan-3-one free base (d-CHCl$_3$, 400 MHz).

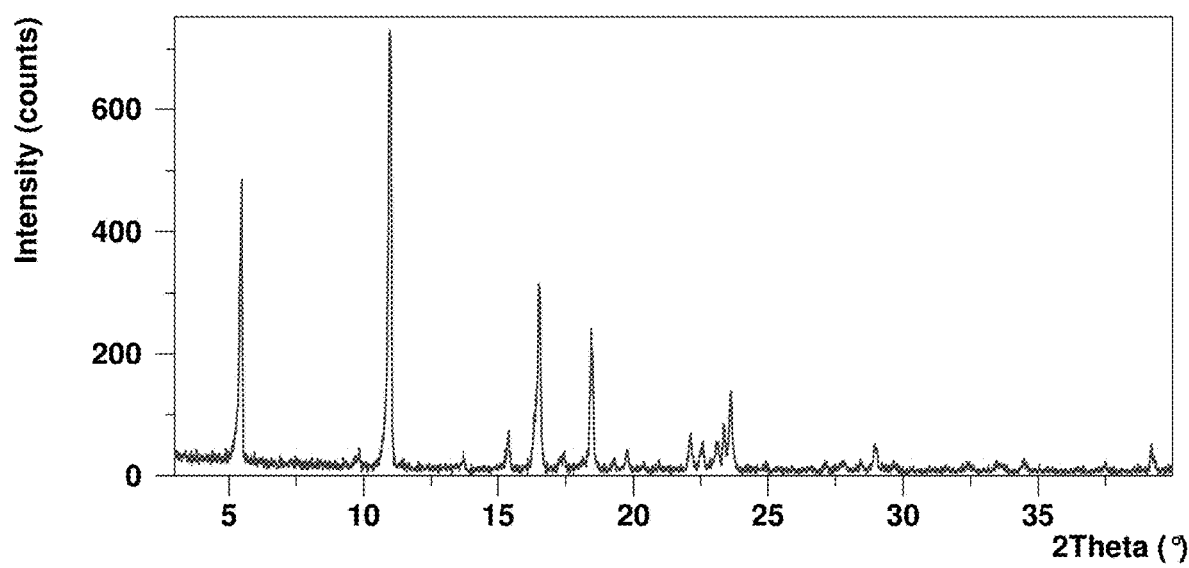
Figure 2. XRPD pattern of hydrochloride salt form P1 obtained by precipitation from a water solution by addition of 1 eq. 1 M HCl.

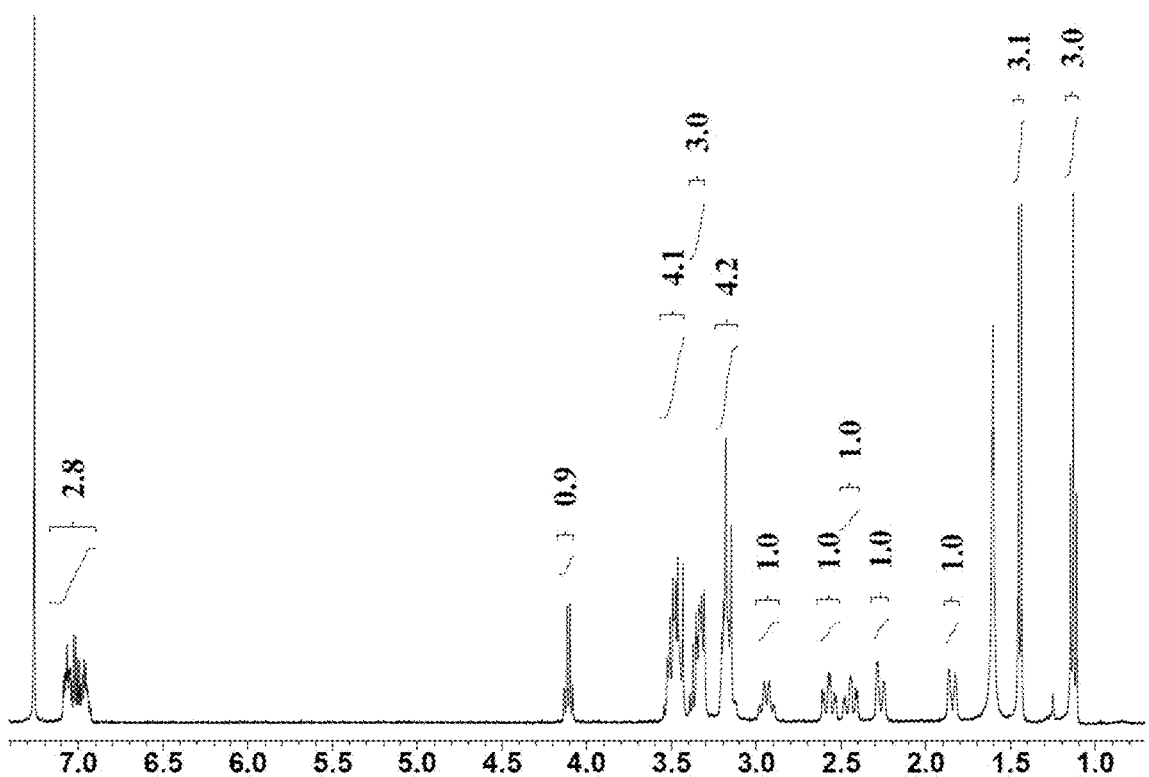
Figure 3. $^1$H-NMR (d-CHCl$_3$, 400 MHz) of hydrochloride salt form P1.

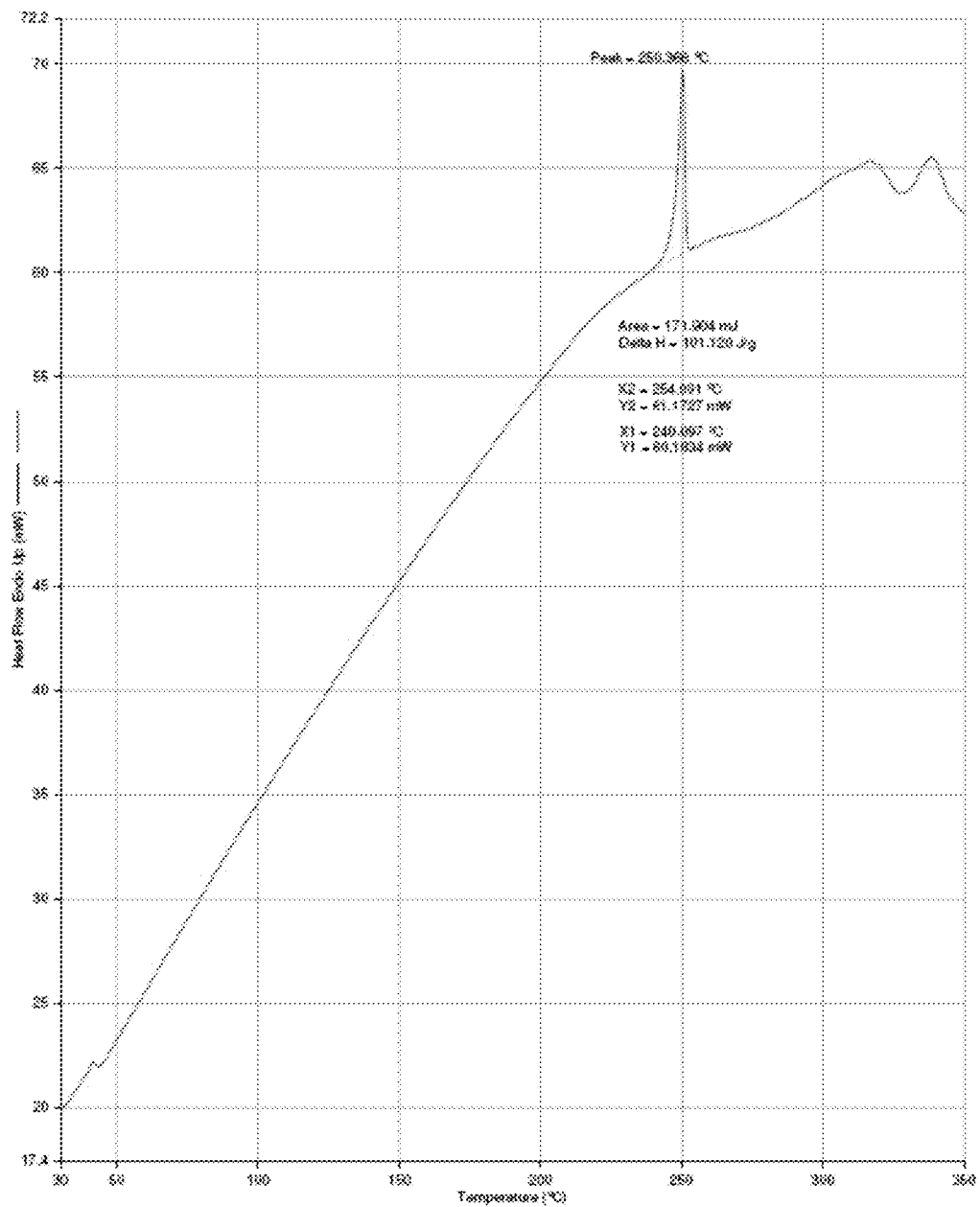
Figure 4. DSC analysis of hydrochloride salt form P1. A single endothermic event is observed at 250 °C (max. peak) attributed to the melting of form P1.

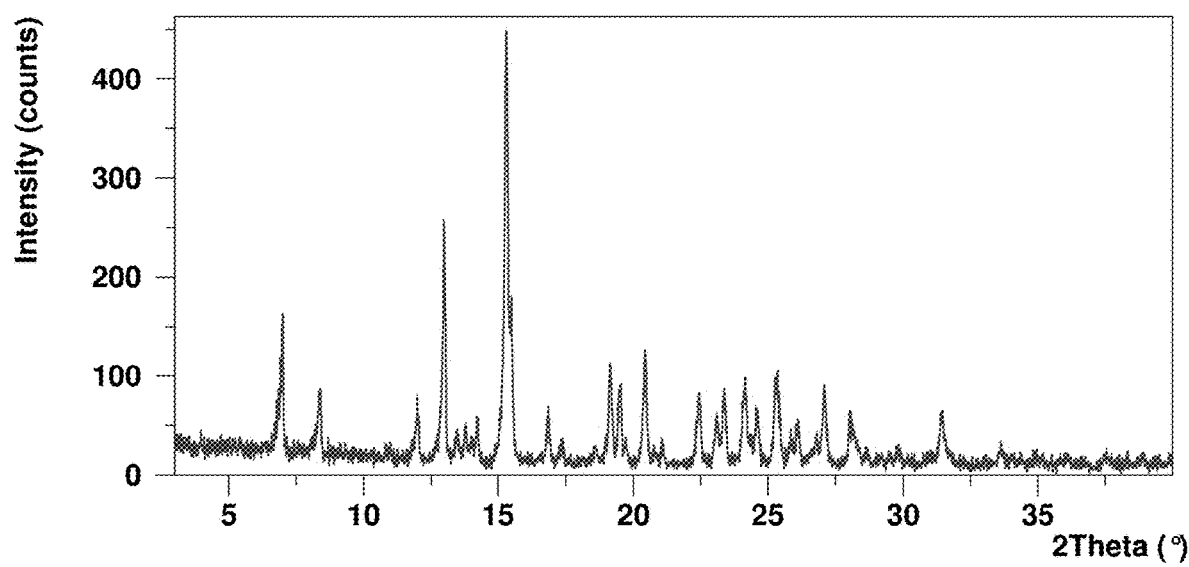
Figure 5. XRPD pattern of hydrochloride salt form P2 obtained by slow evaporation from an IPA solution with 1 eq. of 1 M HCl.

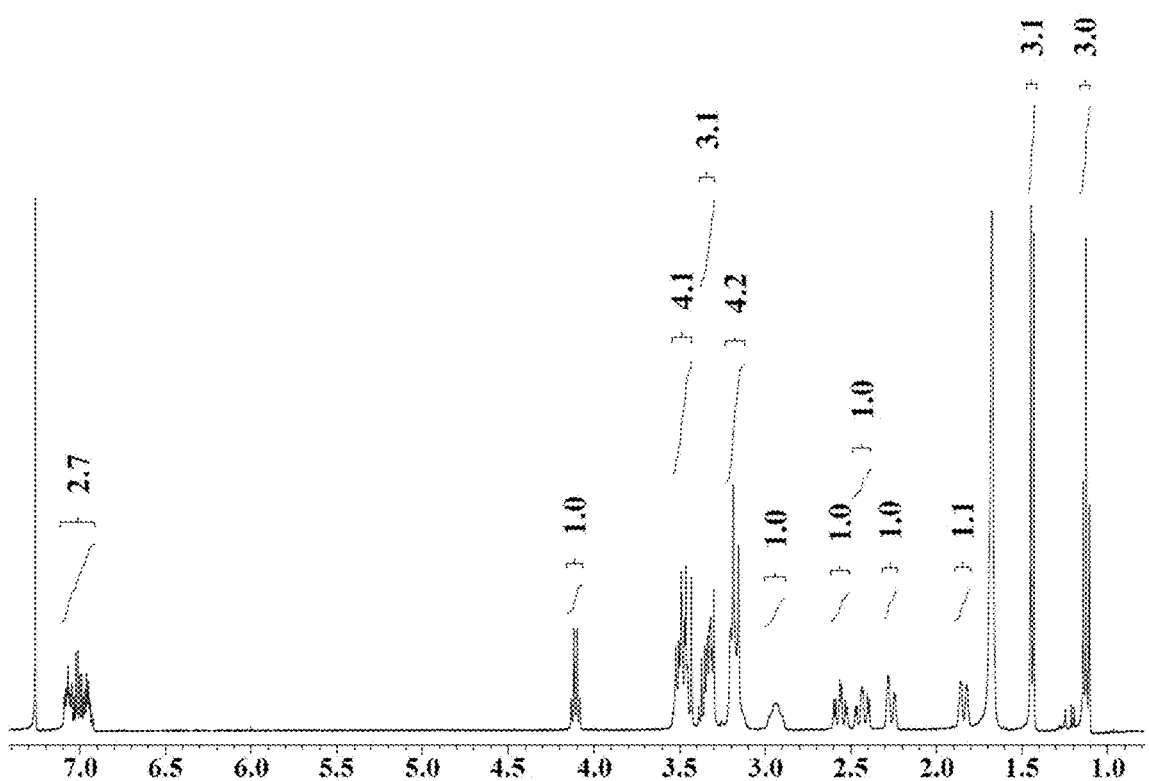
Figure 6. $^1$H-NMR (d-CHCl$_3$, 400 MHz) of hydrochloride salt form P2.

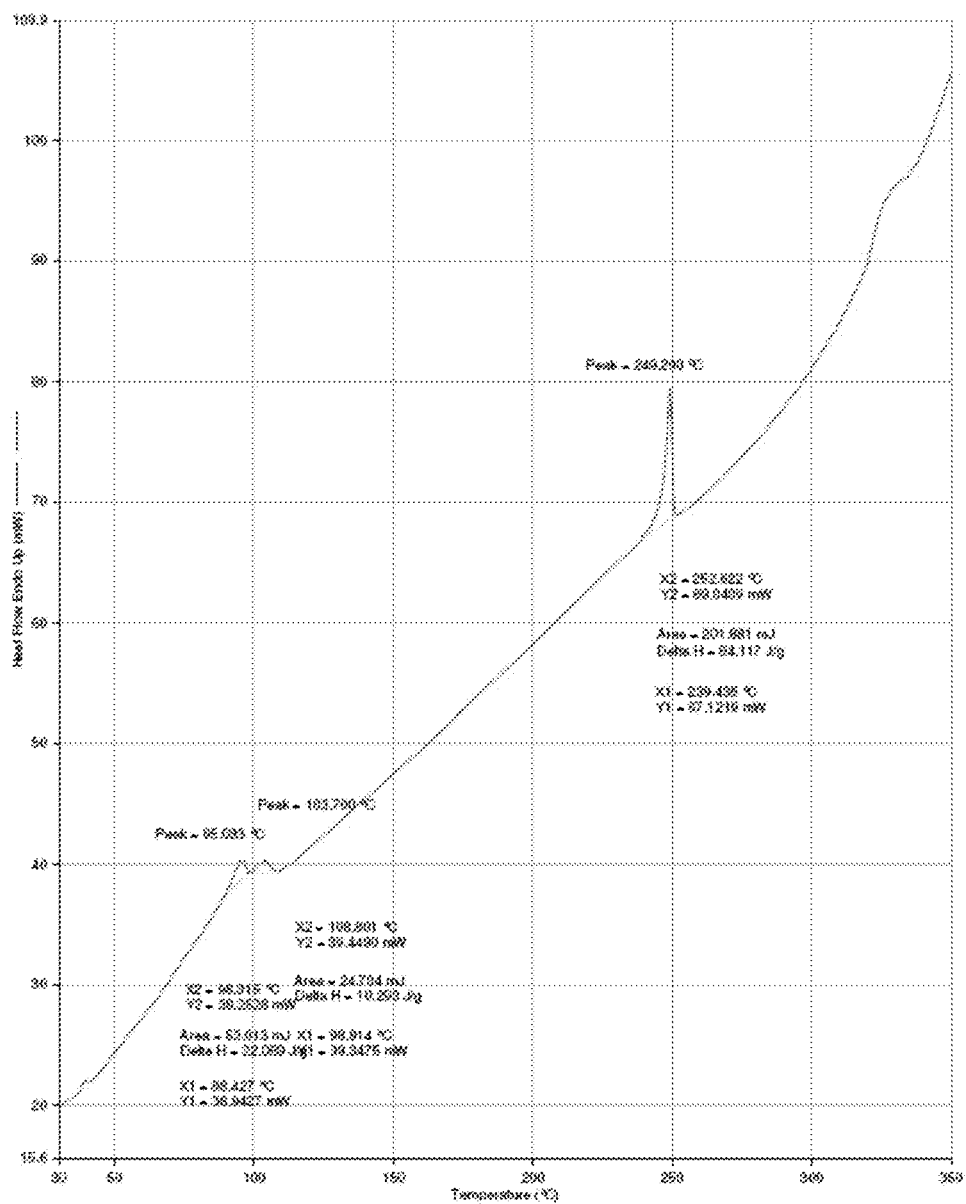
Figure 7. DSC analysis of hydrochloride salt form P2. The first two endothermic events observed at 95 °C and 104 °C might correspond to the dehydration process of the salt. Subsequently, a sharp endothermic peak observed at 249 °C (max. peak) might be attributed to the melting of the anhydrous hydrochloride salt –form P1.

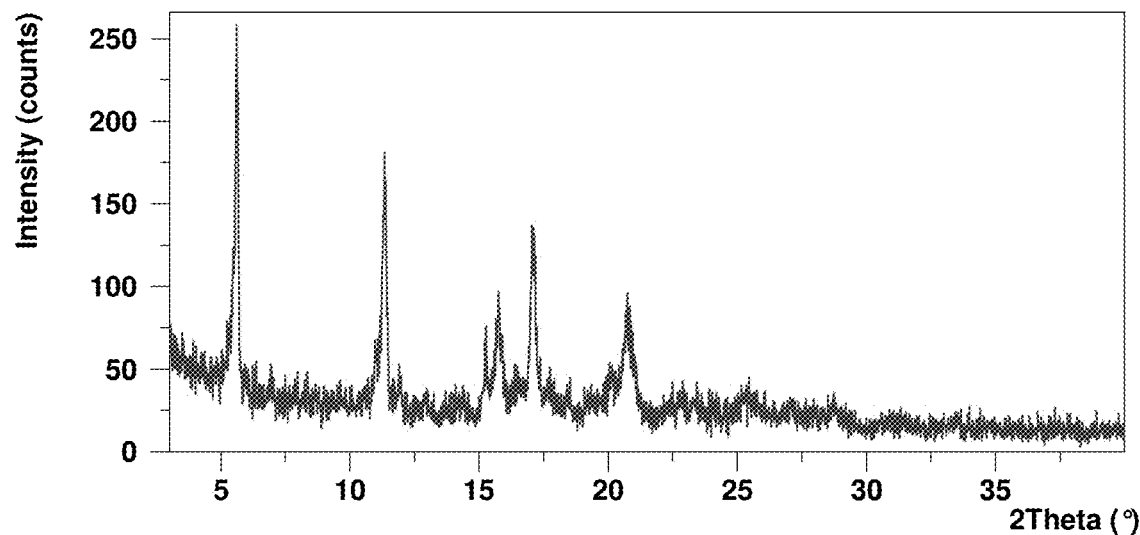
Figure 8. XRPD pattern of hydrochloride salt form P3 obtained by dehydration of hydrochloride Form P2 at 50 °C under vacuum for 1h.
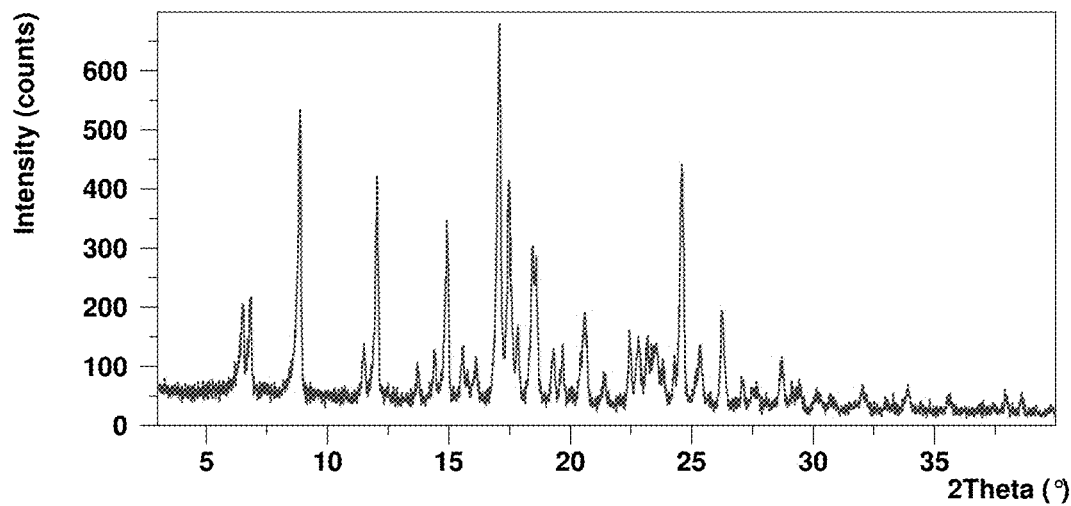
Figure 9. XRPD pattern of fumarate salt form P1 obtained by slurry at rt of the free base in AcOiBu with 1 eq. of fumaric acid.

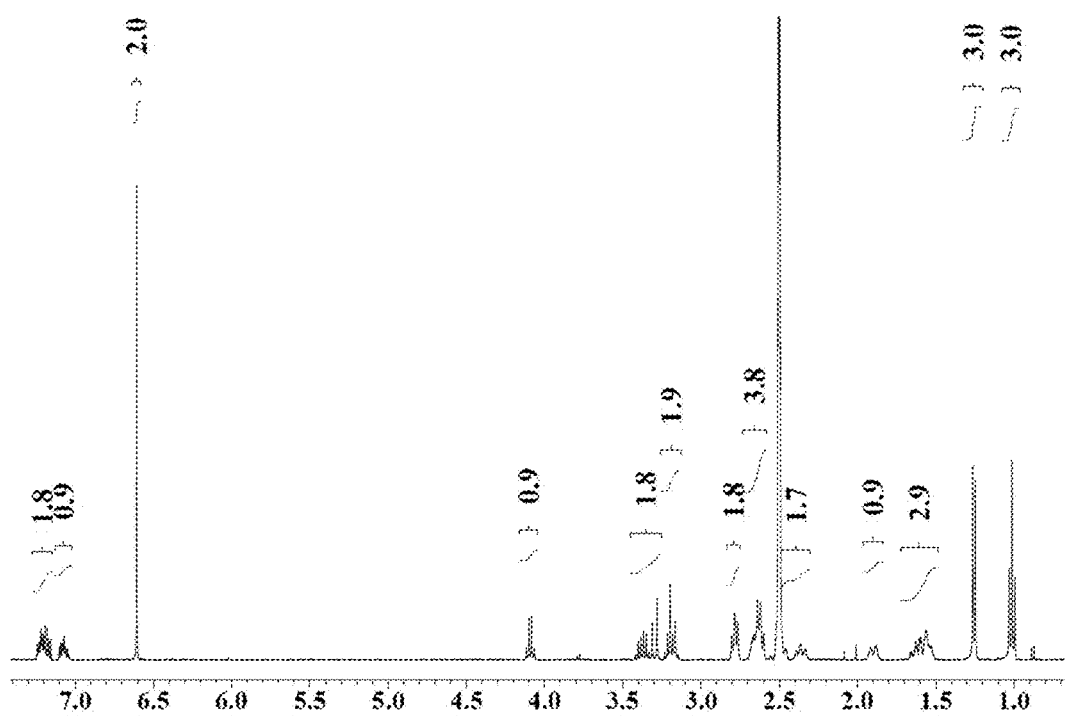
Figure 10. ¹H-NMR (DMSO, 400 MHz) of fumarate salt form P1.

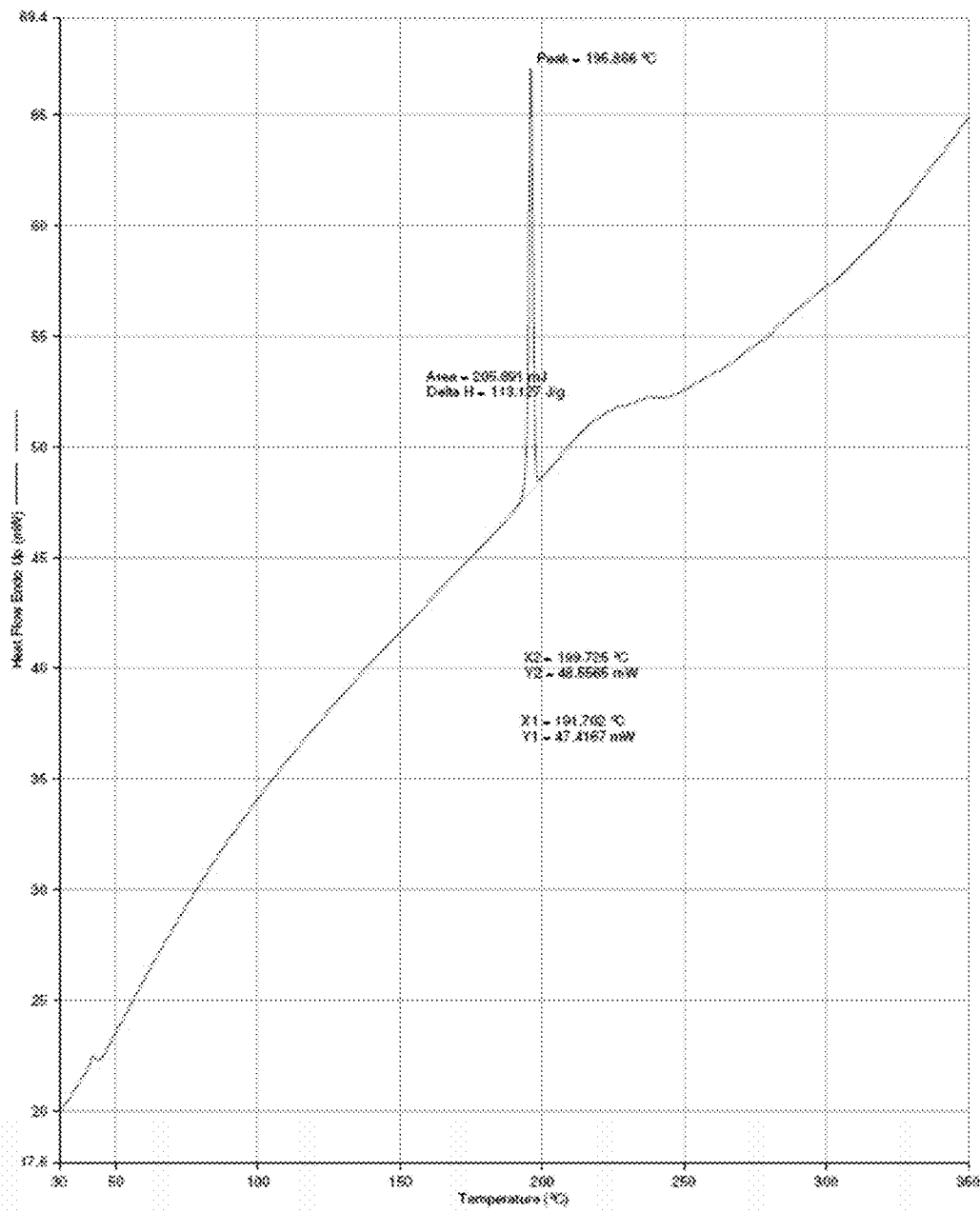
Figure 11. DSC analysis of fumarate salt form P1. A single endothermic event is observed at 197 °C (max. peak) attributed to the melting of the form P1.

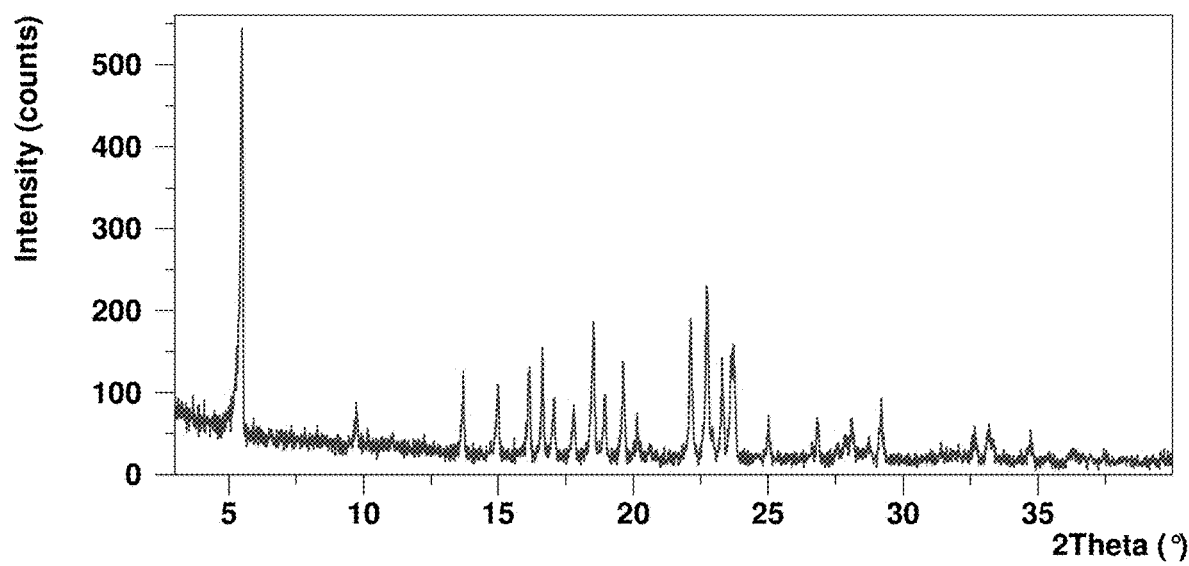
Figure 12: XRPD pattern of hydrobromide salt Form P1 obtained by precipitation in THF.

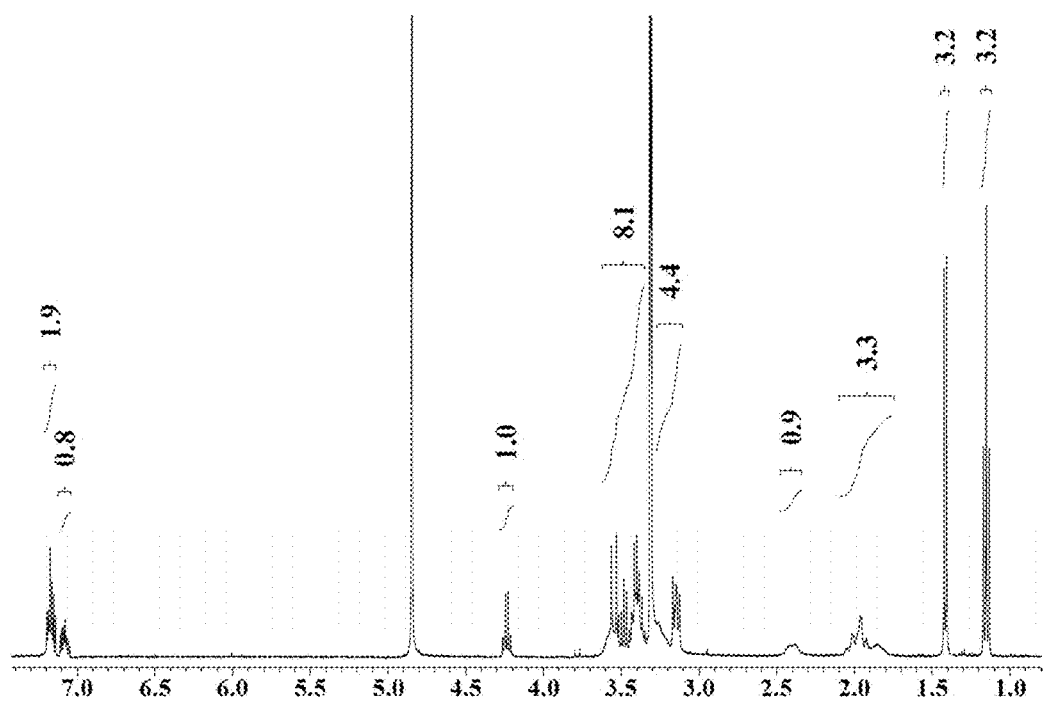
Figure 13: ¹H-NMR (d4-MeOH, 400 MHz) of hydrobromide salt Form P1.

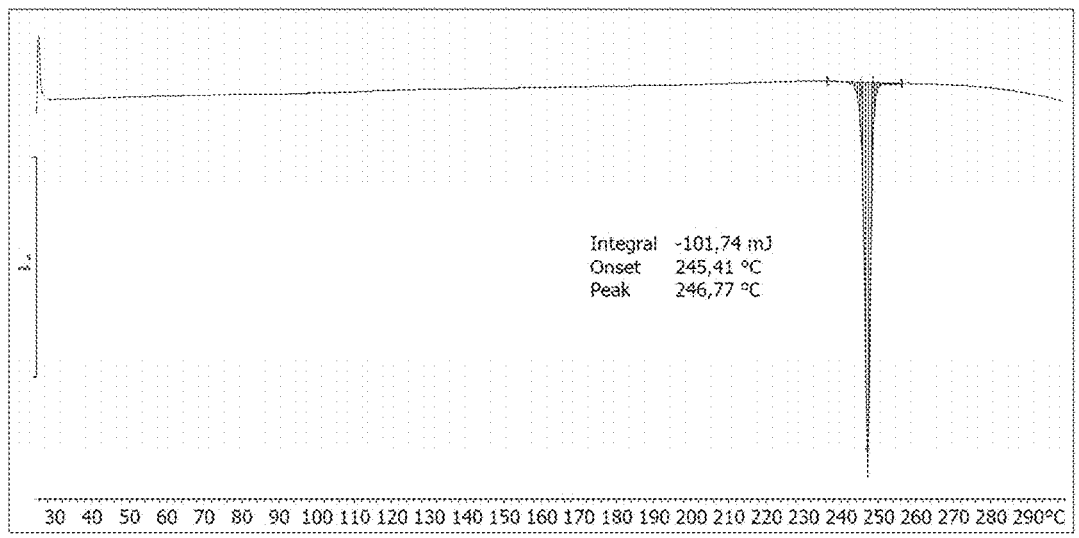
Figure 14: DSC analysis of hydrobromide salt Form P1. A single endothermic event is observed at 245 °C (onset) attributed to the melting of hydrobromide salt Form P1.
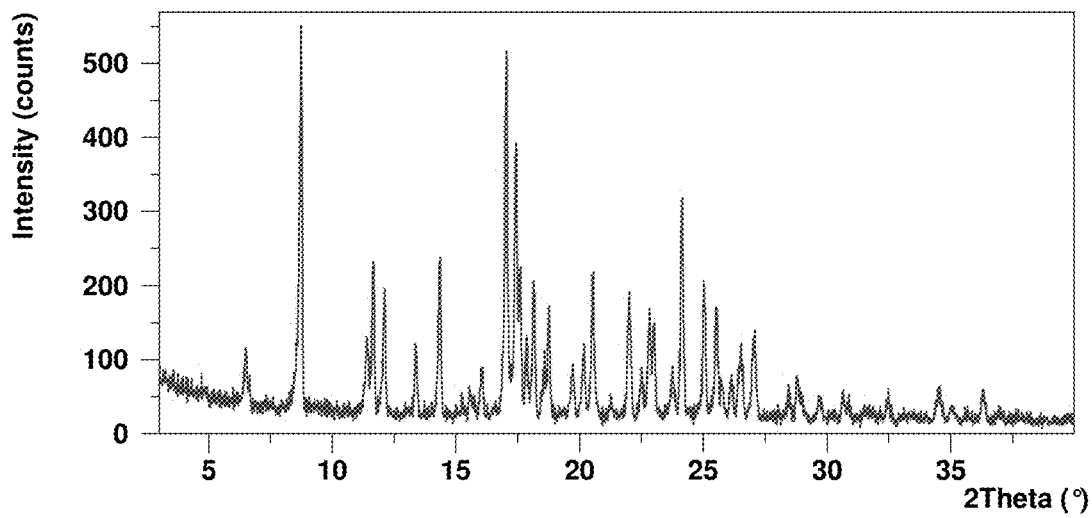
Figure 15: XRPD pattern of maleate salt Form P1 obtained by thermal treatment of form P2.

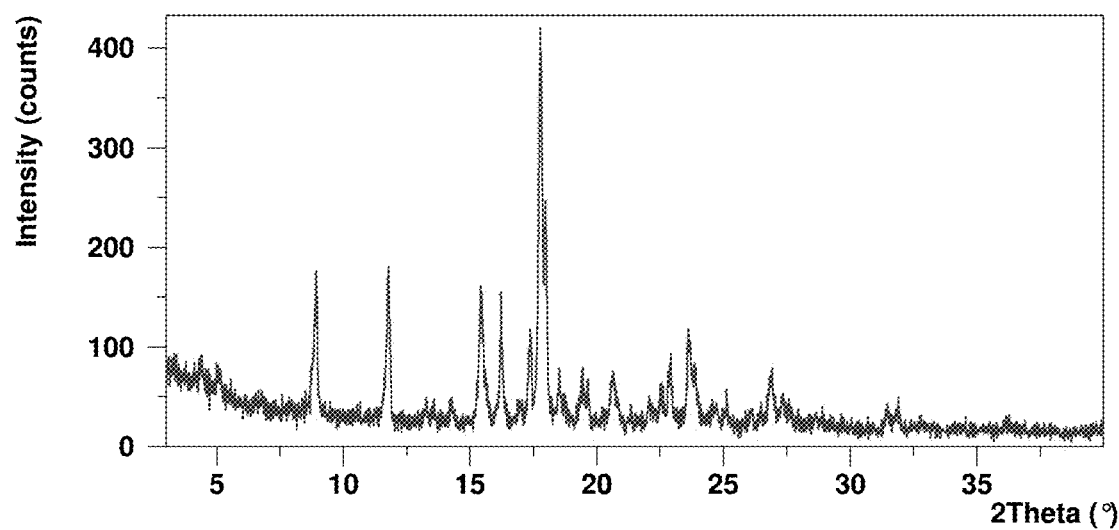
Figure 16: XRPD pattern of maleate salt Form P2 obtained by slurry in MIK.

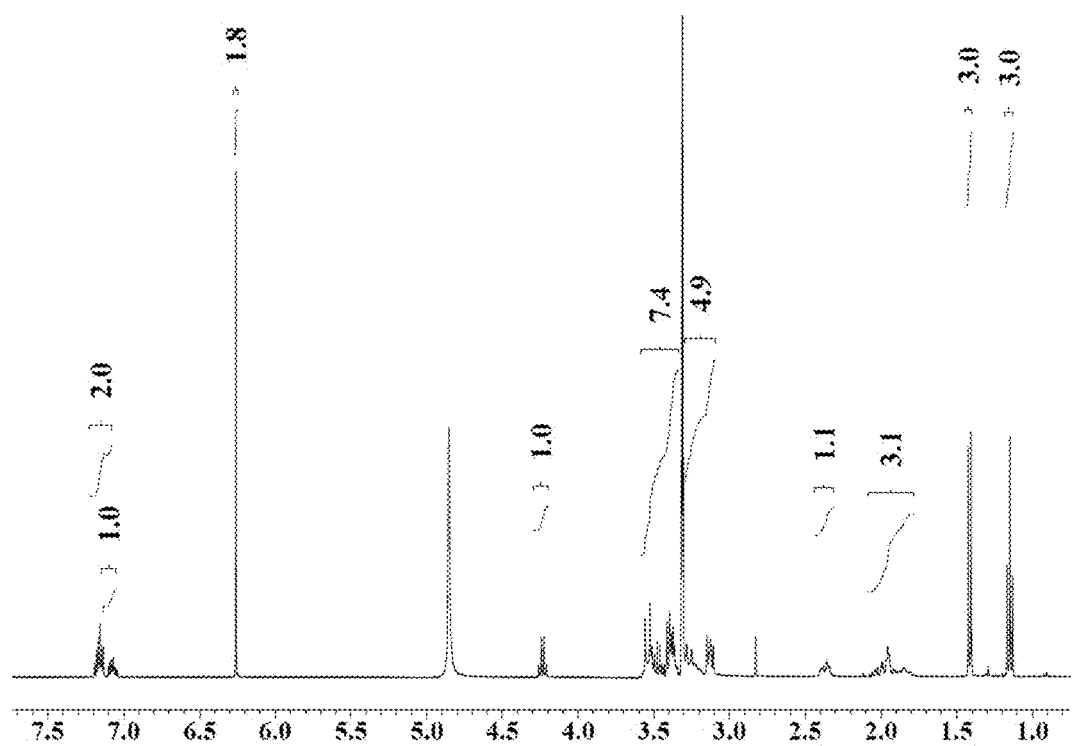
Figure 17: ¹H-NMR (*d4*-MeOH, 400 MHz) of maleate salt Form P2.

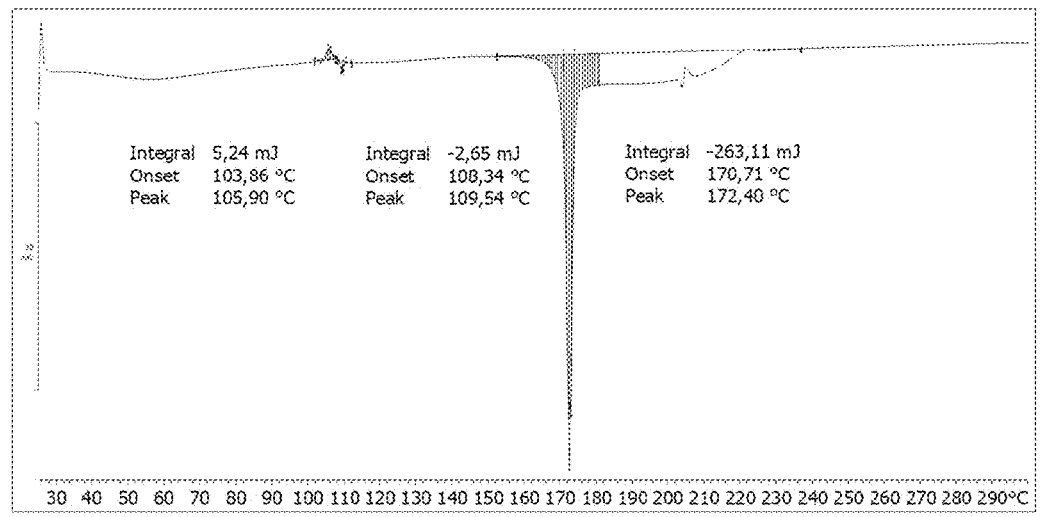
Figure 18: DSC analysis of maleate salt Form P2 obtained by slurry in MIK. A small exothermic event (104 °C) followed by a small endotherm (108 °C) is observed, which nature are unknown. The melting of the solids is observed at 171 °C (onset).
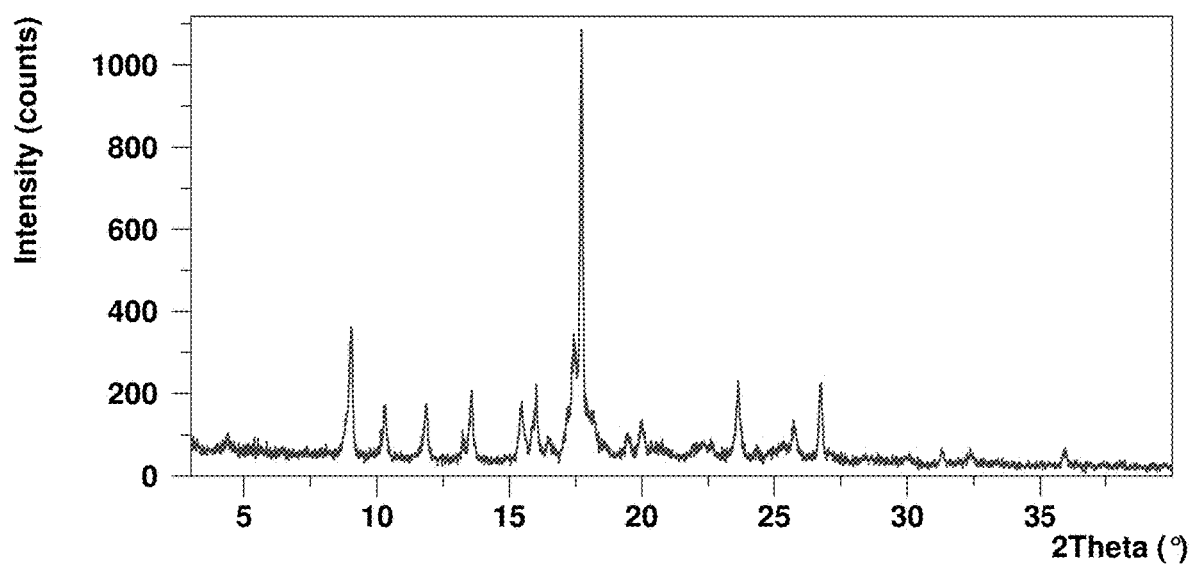
Figure 19: XRPD pattern of maleate salt Form P3 obtained by precipitation in IPA.

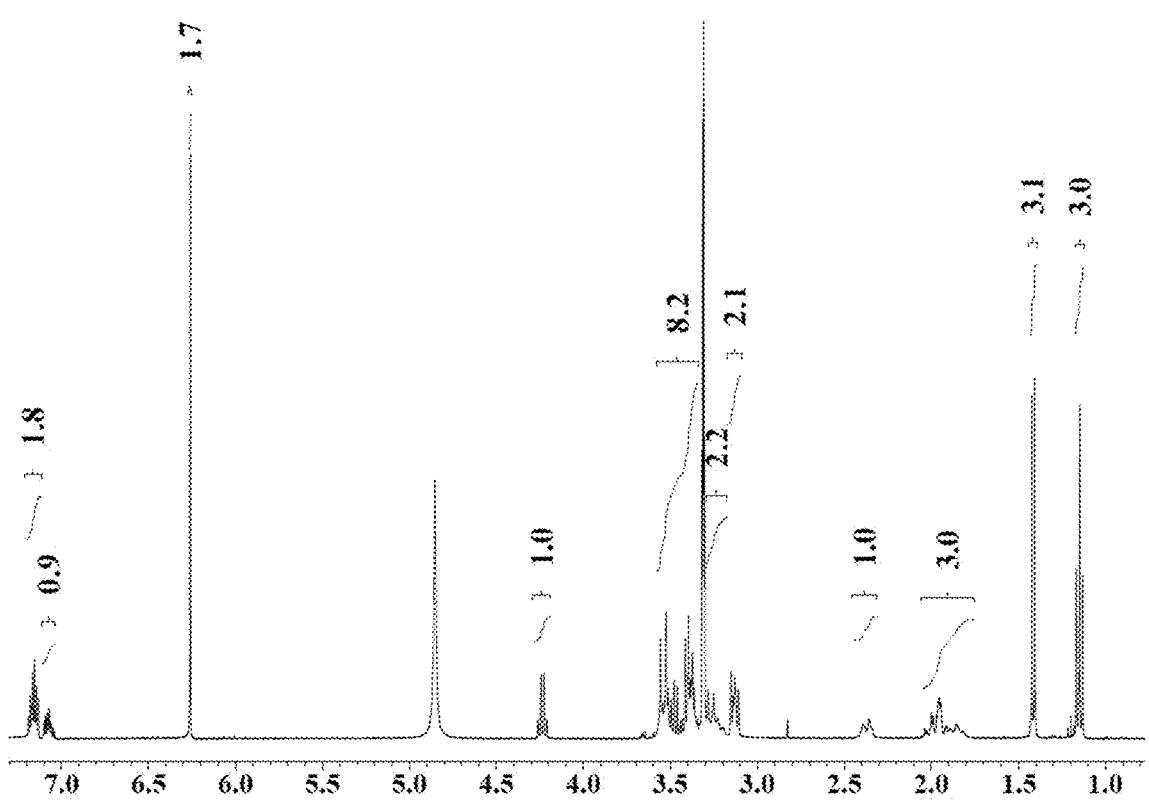
Figure 20: $^1$H-NMR (d4-MeOH, 400 MHz) of maleate salt Form P3.

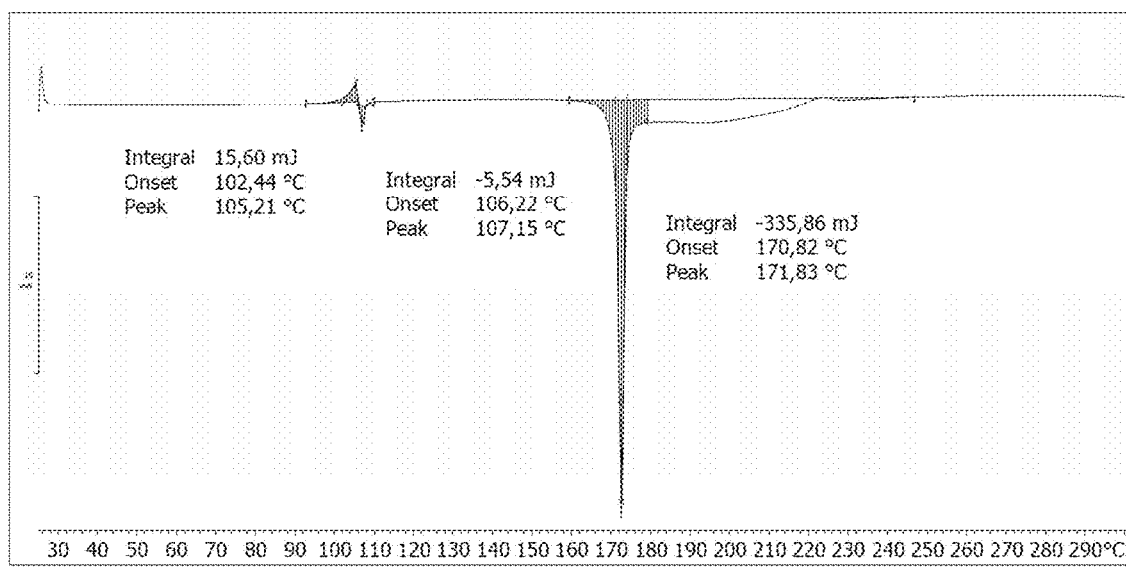
Figure 21: DSC analysis of maleate salt Form P3. A small exothermic event (102 °C) followed by a small endotherm (106 °C) is observed which nature are unknown. The melting of the solids is observed at 171 °C (onset).

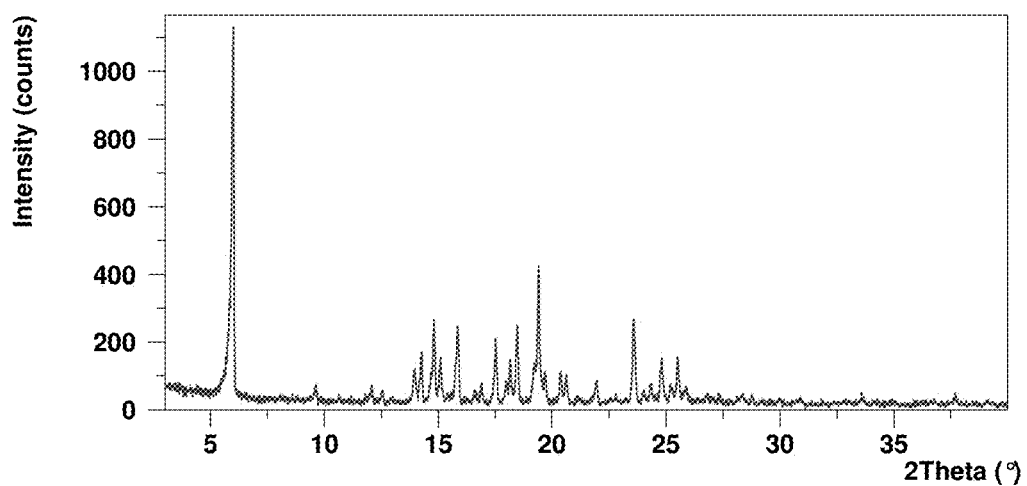
Figure 22: XRPD pattern of besylate salt Form P1 obtained by precipitation from IPA.

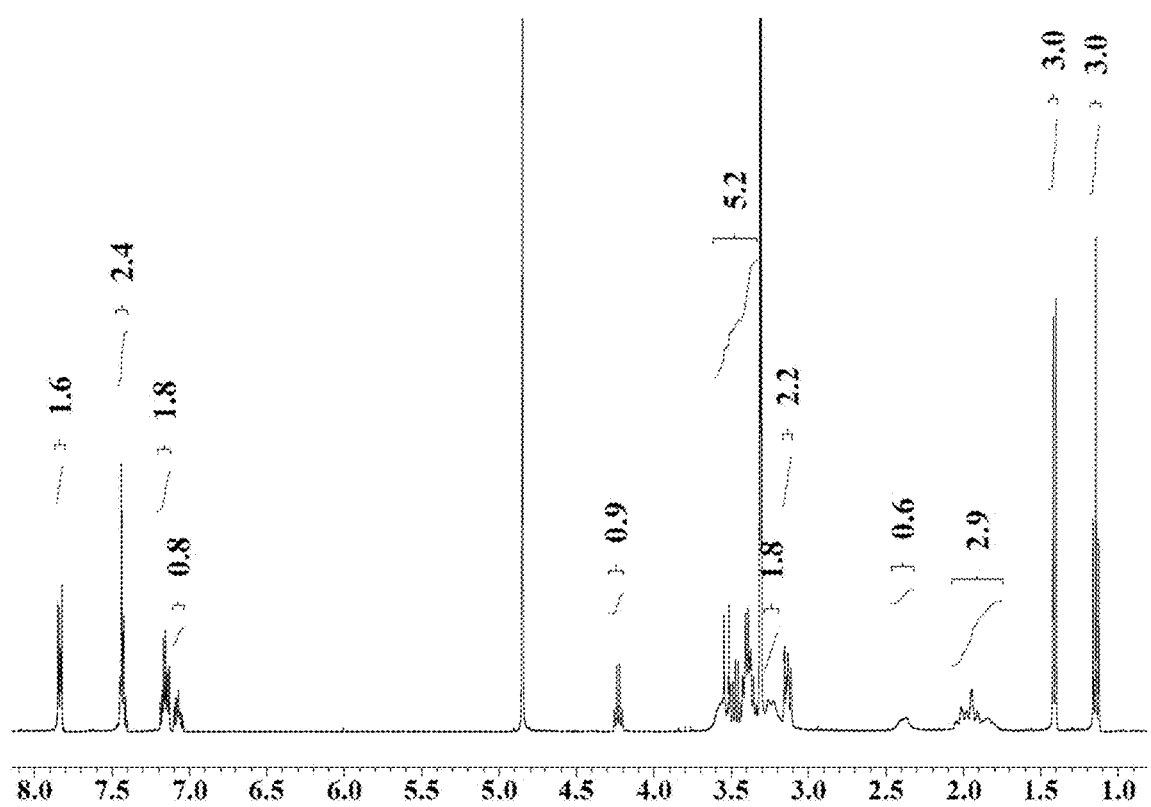
Figure 23: ¹H-NMR (*d4*-MeOH, 400 MHz) of besylate salt Form P1.

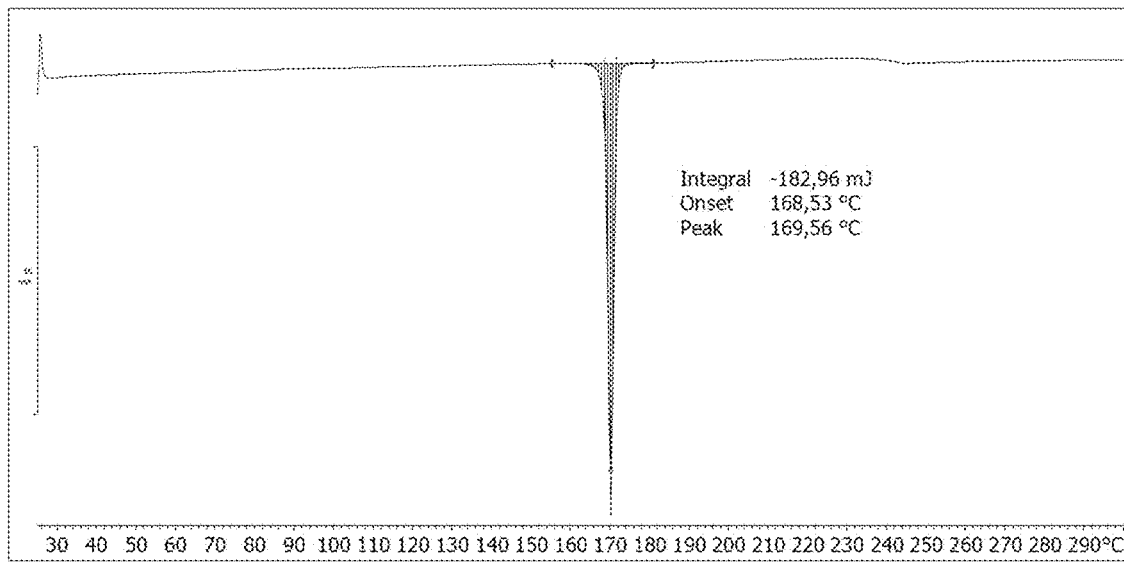
Figure 24: DSC analysis of besylate salt Form P1. A single endothermic event is observed at 169 °C (onset), which is attributed to the melting of the potential besylate salt Form P1.
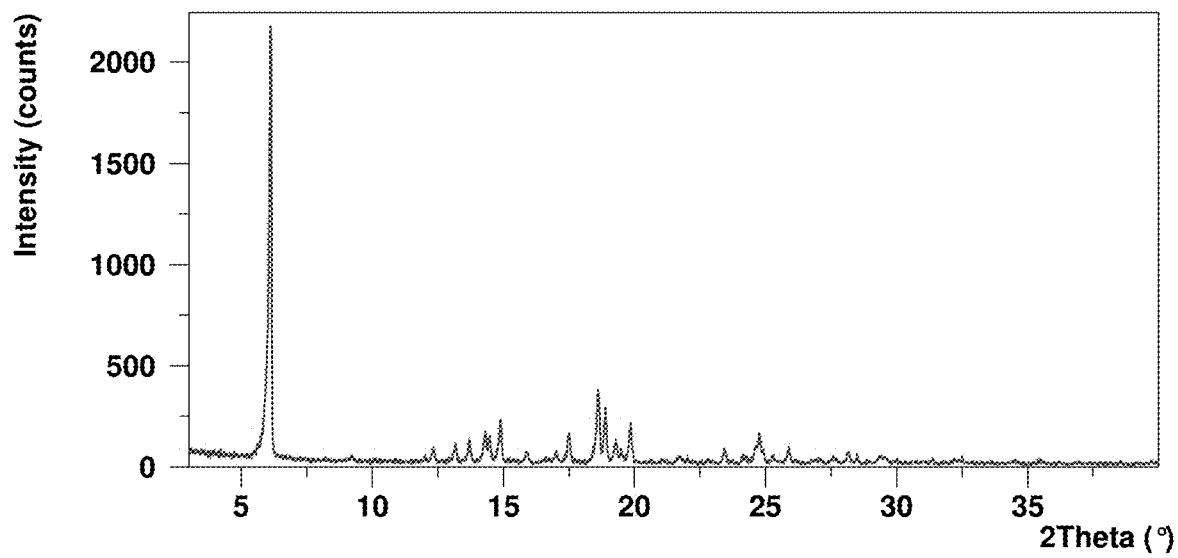
Figure 25: XRPD pattern of besylate salt Form P2 obtained upon exposure of Form P1 to elevated humidity conditions (90%).

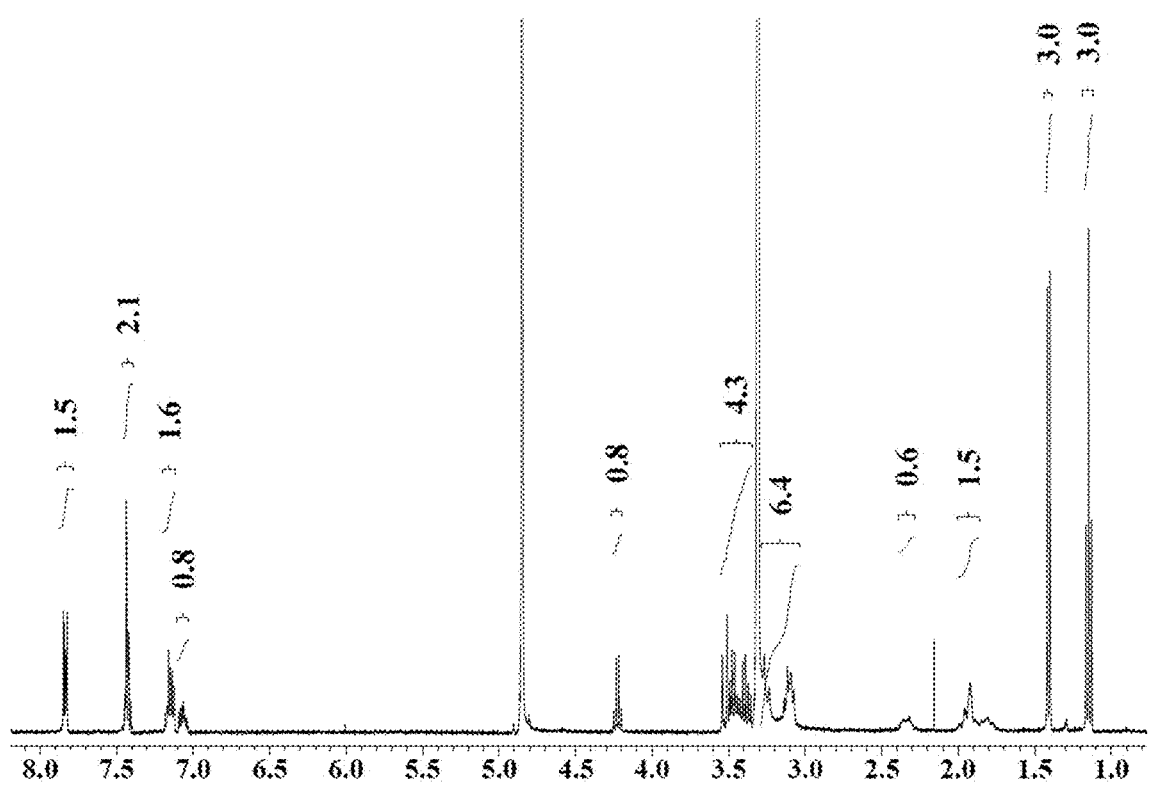
Figure 26: ¹H-NMR (*d4*-MeOH, 400 MHz) of besylate salt Form P2.

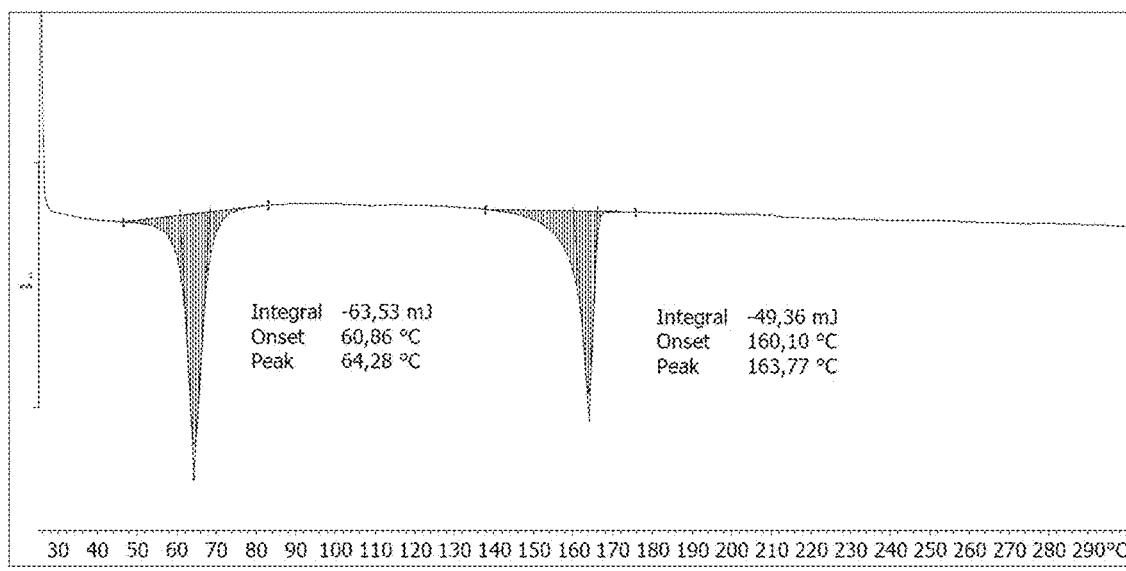
Figure 27: DSC analysis of besylate salt Form P2. A first endothermic event is observed at 61 °C (onset), which is attributed to water release. This event might indicate the hydrated nature of the salt Form P2. The melting of the besylate salt is observed ad 160 °C (onset).

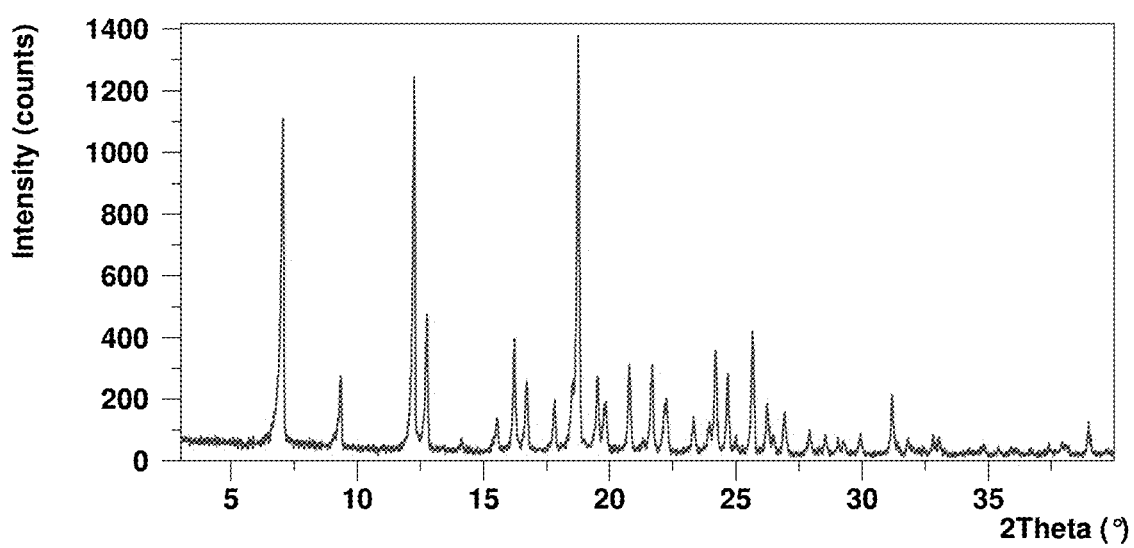
Figure 28: XRPD pattern of phosphate salt Form P1 obtained by precipitation in THF

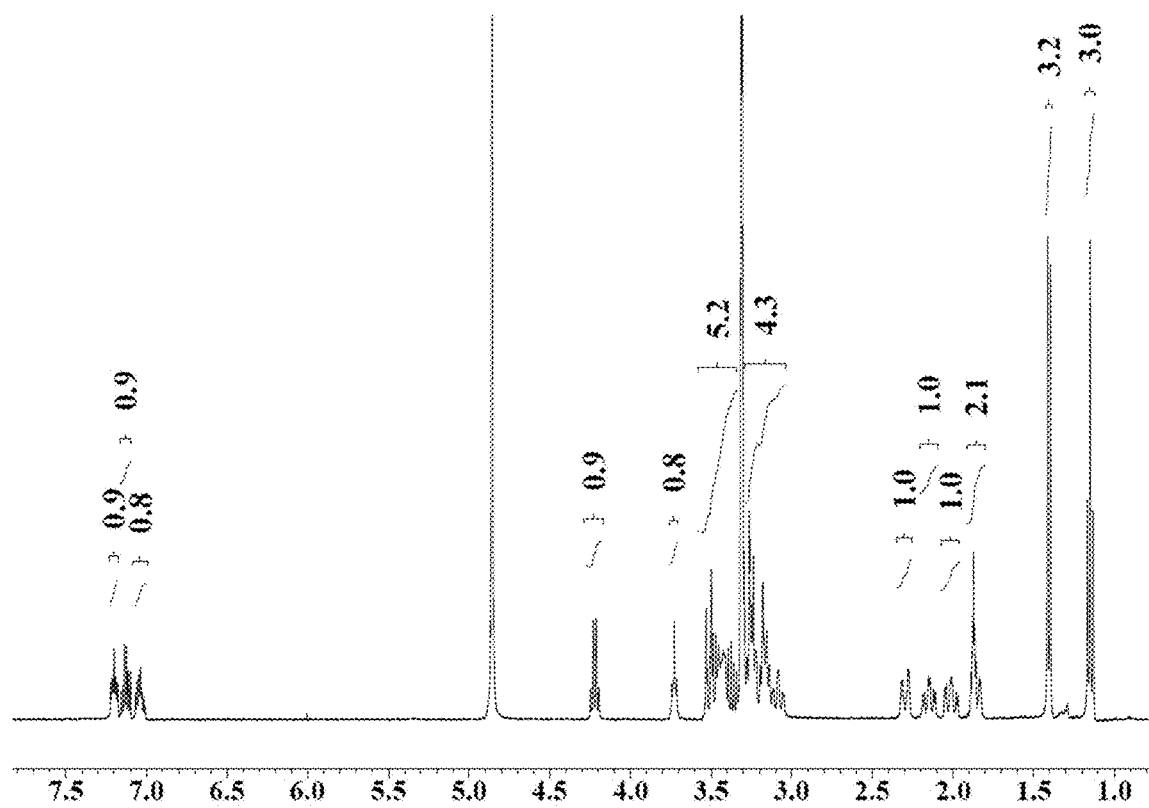
Figure 29: $^1$H-NMR (*d4*-MeOH, 400 MHz) of phosphate salt Form P1.

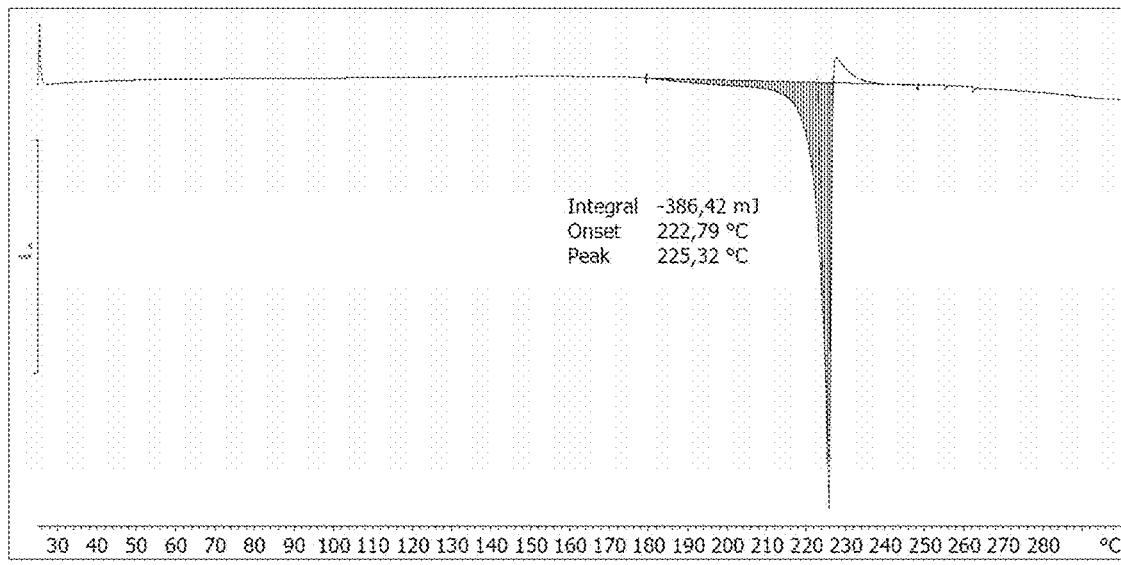
Figure 30: DSC analysis of phosphate salt Form P1. A single endothermic event is observed at 223 °C, which is attributed to the melting of the potential phosphate salt Form P1. The exothermic event observed after the melting might correspond to the salt disproportionation.
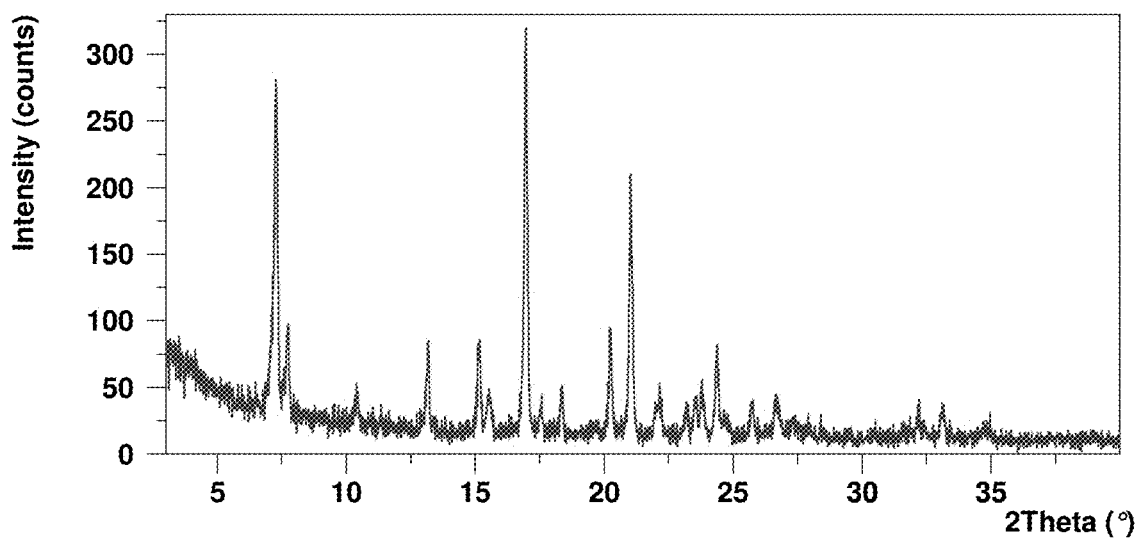
Figure 31: XRPD pattern of sulfate salt Form P1 obtained by precipitation in IPA.

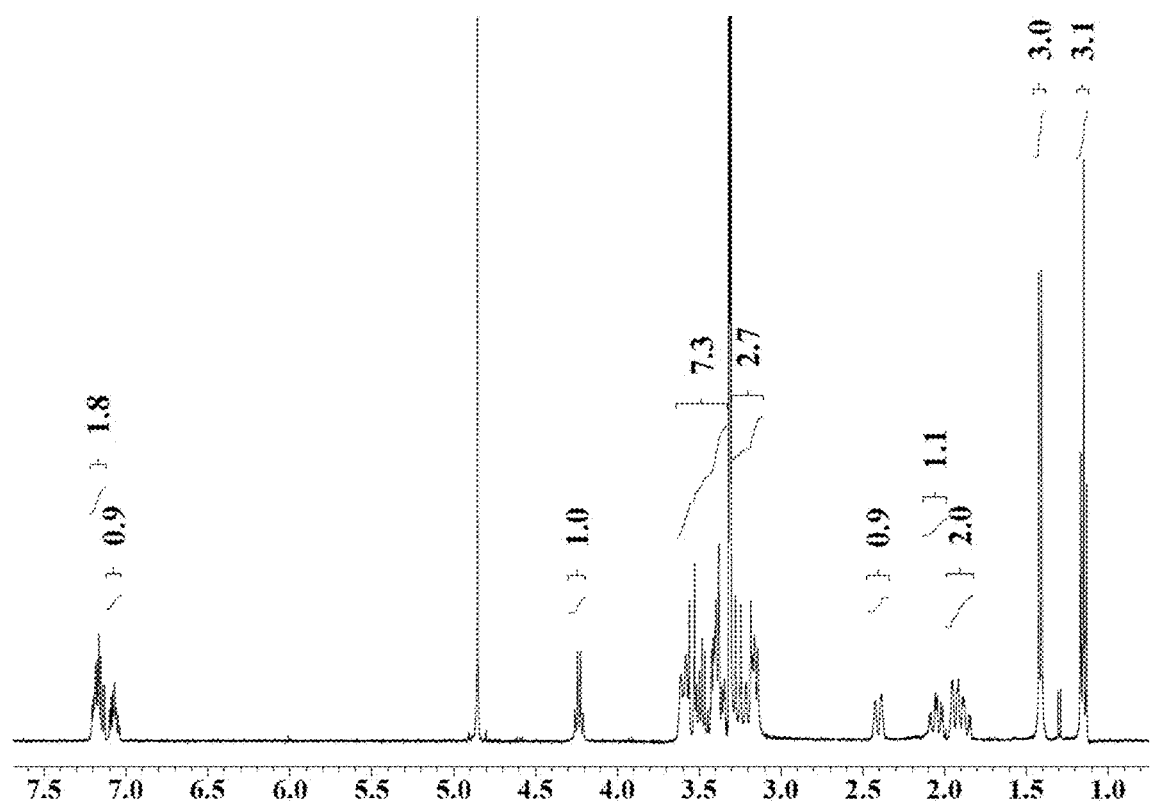
Figure 32: $^1$H-NMR (d4-MeOH, 400 MHz) of sulfate salt Form P1.

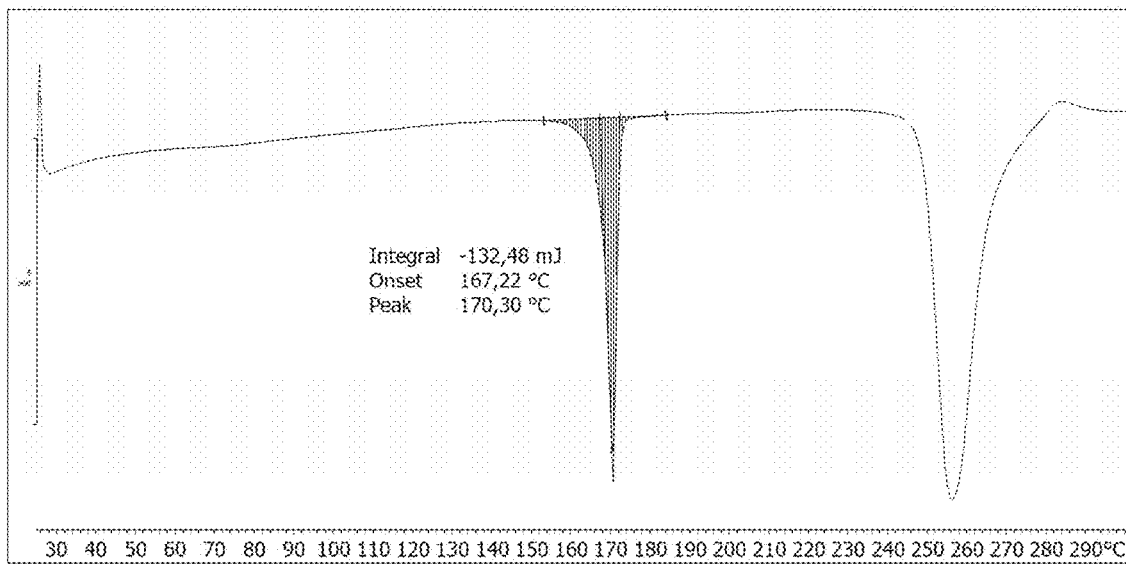
Figure 33: DSC analysis of sulfate salt Form P1. A single endothermic event is observed at 167 °C, which is attributed to the melting of the potential sulfate salt Form P1. A second endothermic event is attributed to the salt decomposition.
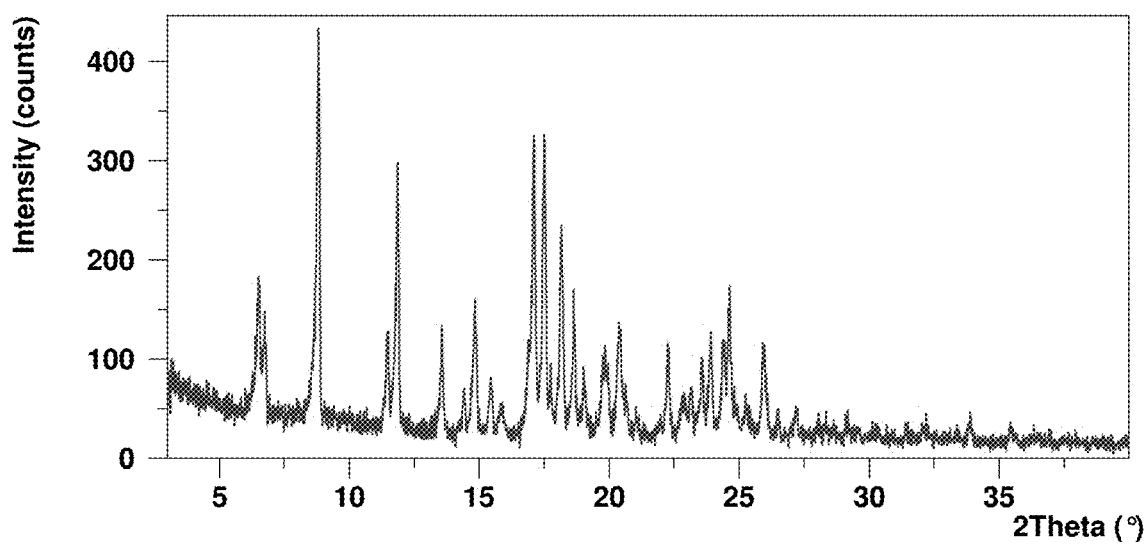
Figure 34: XRPD pattern of succinate salt Form P1 obtained by slurry in MIK.

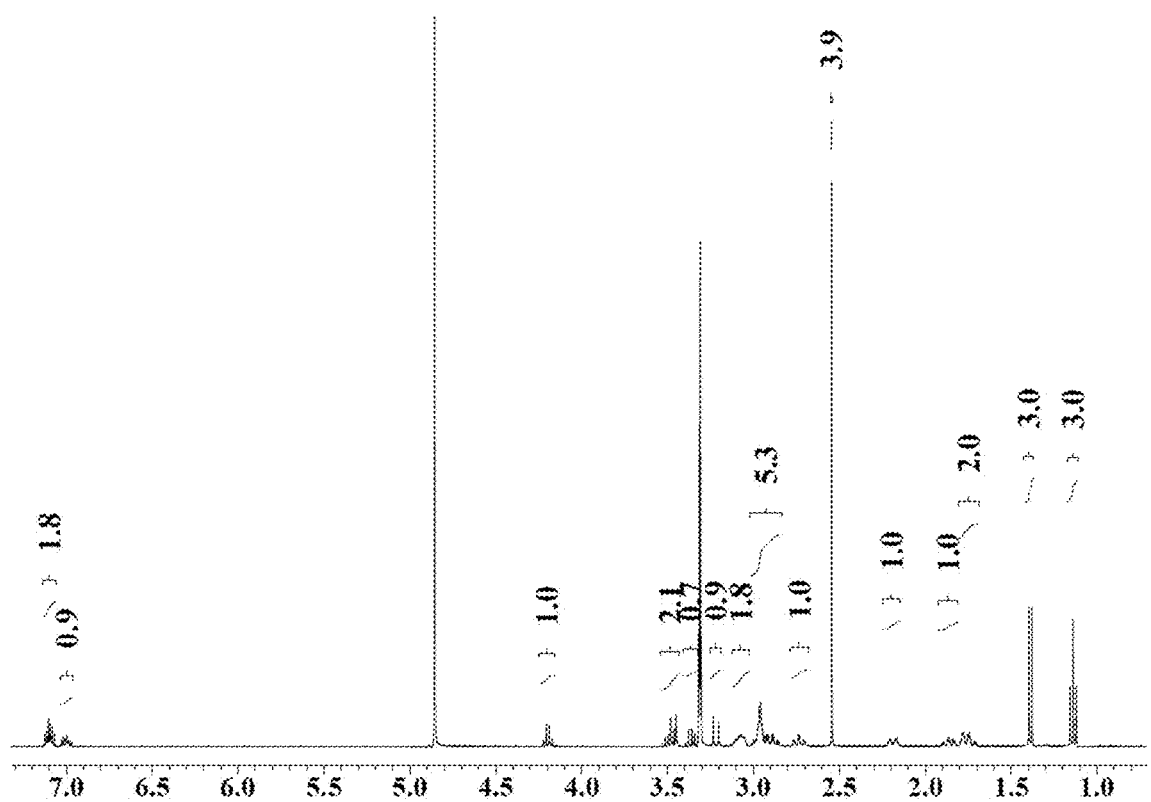
Figure 35: ¹H-NMR (*d4*-MeOH, 400 MHz) of succinate salt Form P1.

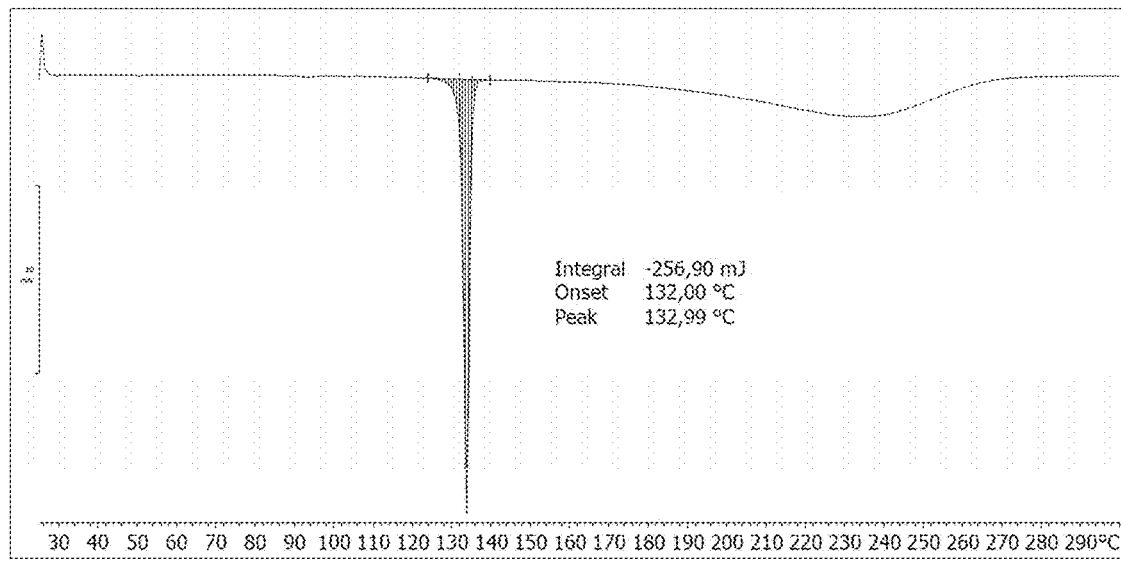
Figure 36: DSC analysis of succinate salt Form P1. A single endothermic event is observed at 132 °C (onset) which is attributed to the melting of the potential succinate salt Form P1.
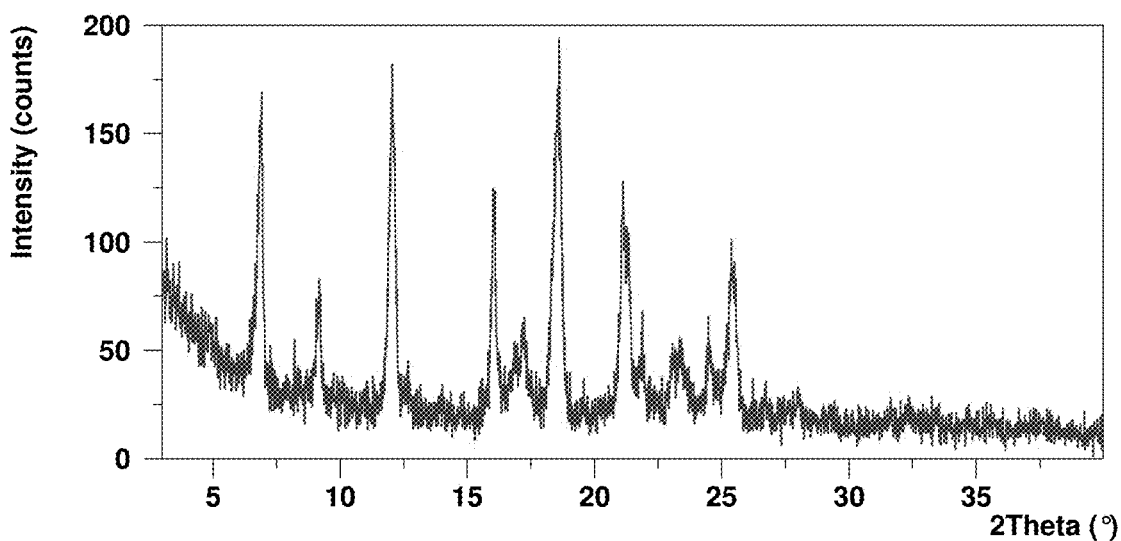
Figure 37: XRPD pattern of oxalate salt Form P1 obtained by precipitation in IPA

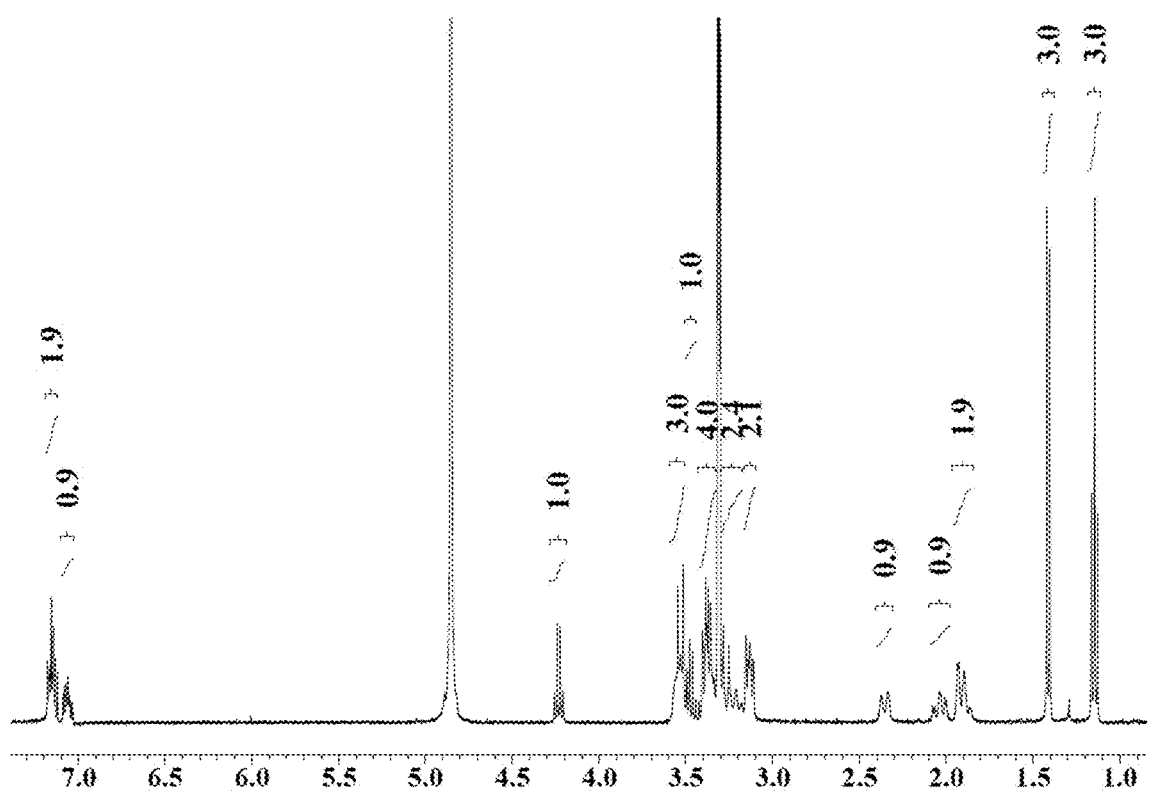
Figure 38: ¹H-NMR (d4-MeOH, 400 MHz) of oxalate salt Form P1.

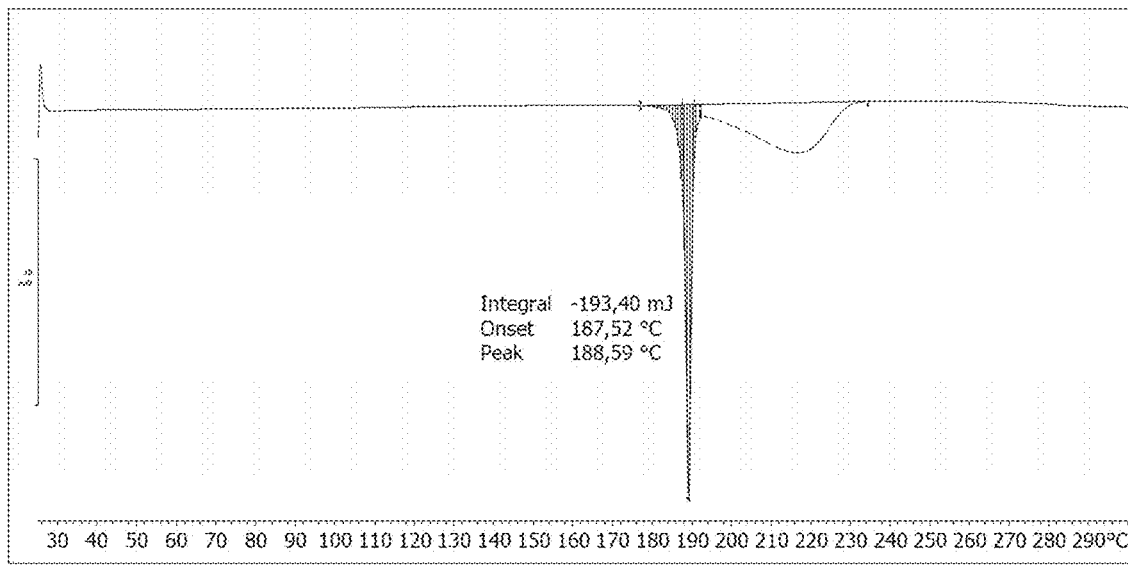

Figure 39: DSC analysis of oxalate salt Form P1. A single endothermic event is observed at 188 °C (onset) which is attributed to the melting of the potential oxalate salt Form P1. A broad endothermic event is observed after the melting, which is attributed to the salt disproportionation or thermal decomposition.

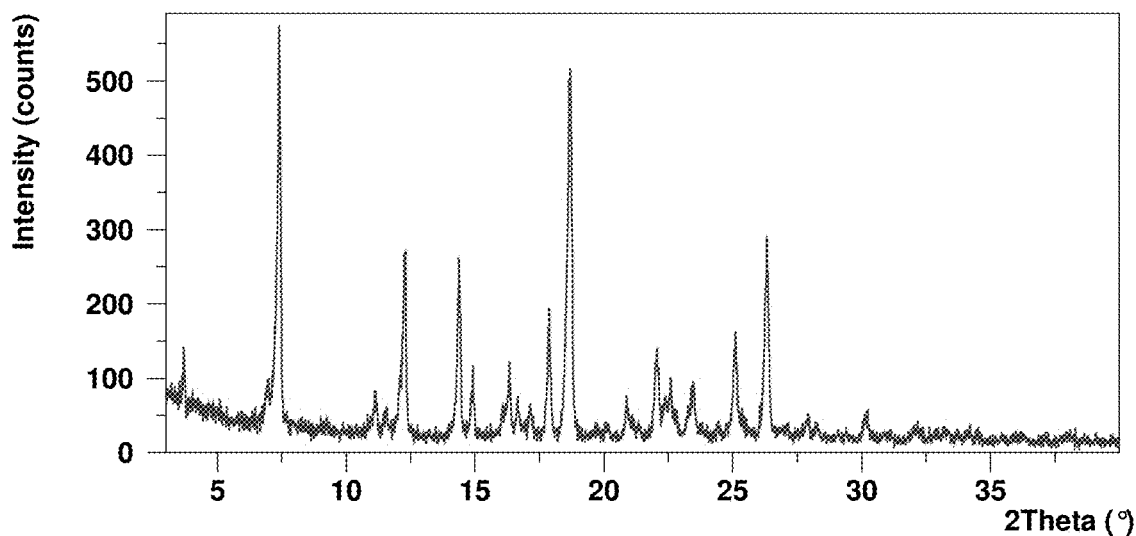

Figure 40: XRPD pattern of oxalate salt Form P2 obtained by precipitation in MIK.

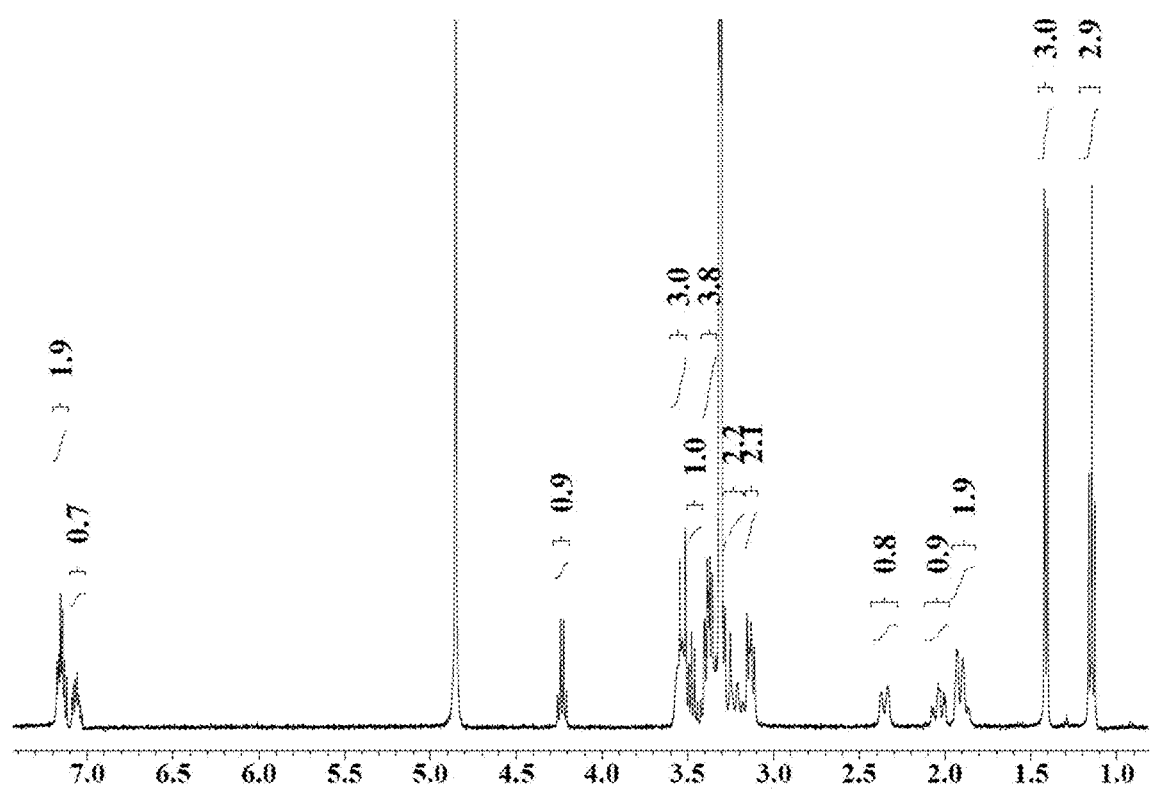
Figure 41: ¹H-NMR (d4-MeOH, 400 MHz) of oxalate salt Form P2.

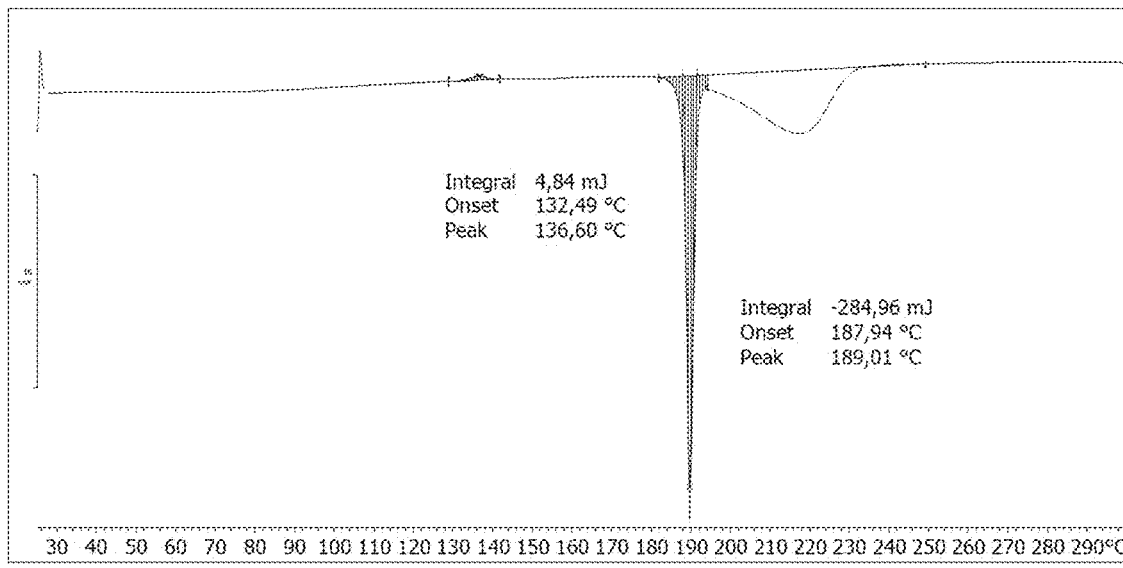

Figure 42: DSC analysis of oxalate salt Form P2. A small exothermic event is observed at 132 °C which nature is not clear. The melting point of this potential oxalate salt is the same as Form P1–188°C, onset –. Additional investigation led to the conclusion that a solid-solid transition occurs –depicted by the exothermic event observed at 132 °C – from P2 to P1.

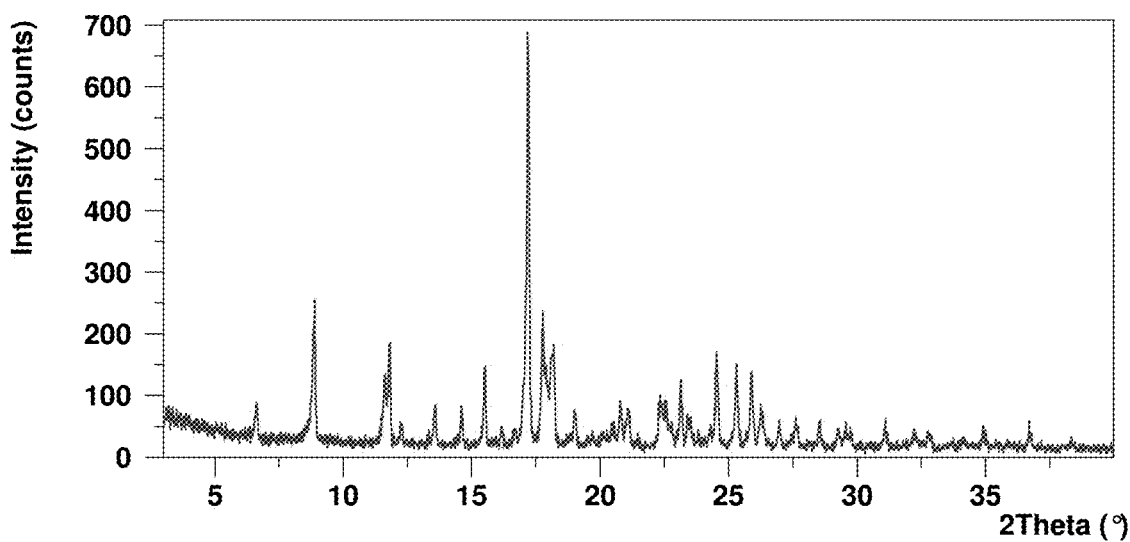

Figure 43: XRPD pattern of malonate salt Form P1 obtained by precipitation in IPA.

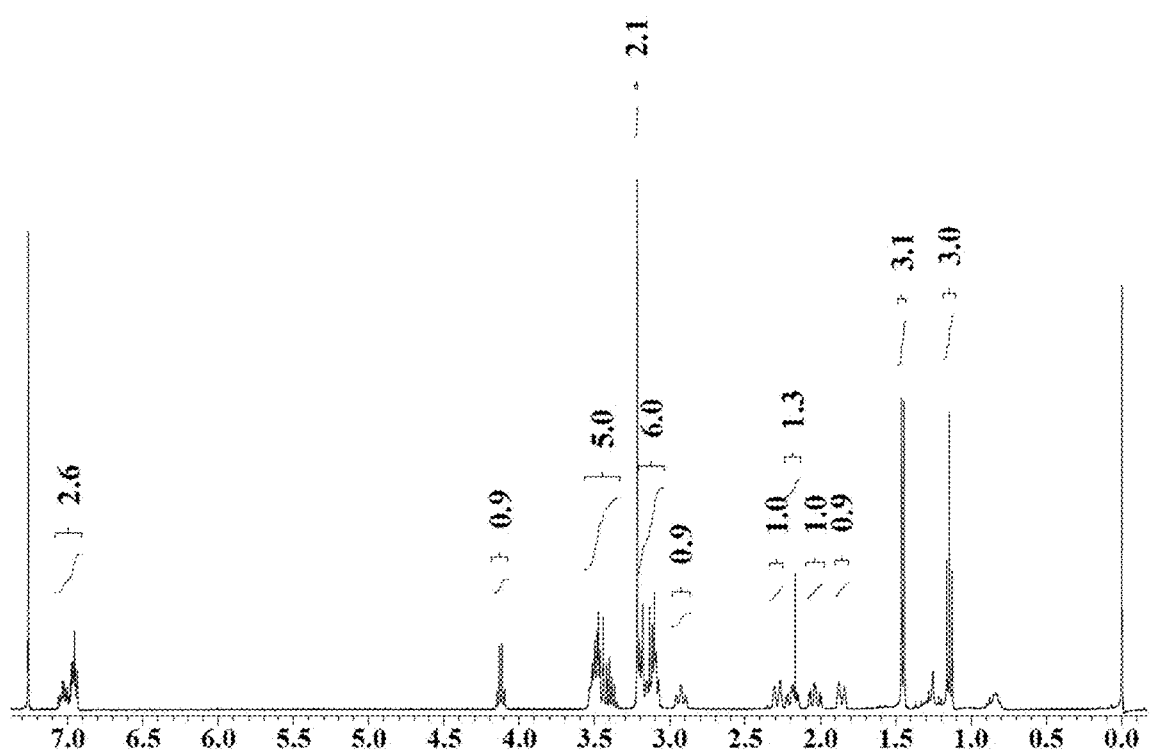
Figure 44: $^1$H-NMR (*d3*-CHCl$_3$, 400 MHz) of malonate salt Form P1.

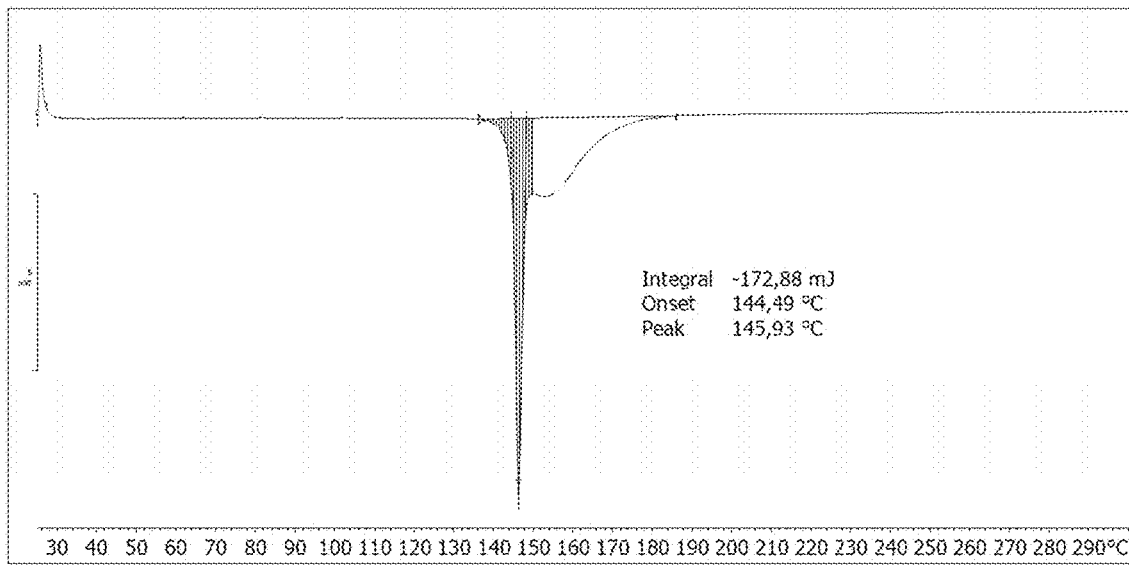
Figure 45: DSC analysis of malonate salt Form P1. A single endothermic event is observed at 144 °C (onset). A broad endothermic event is observed after the melting which is attributed to the salt disproportionation.
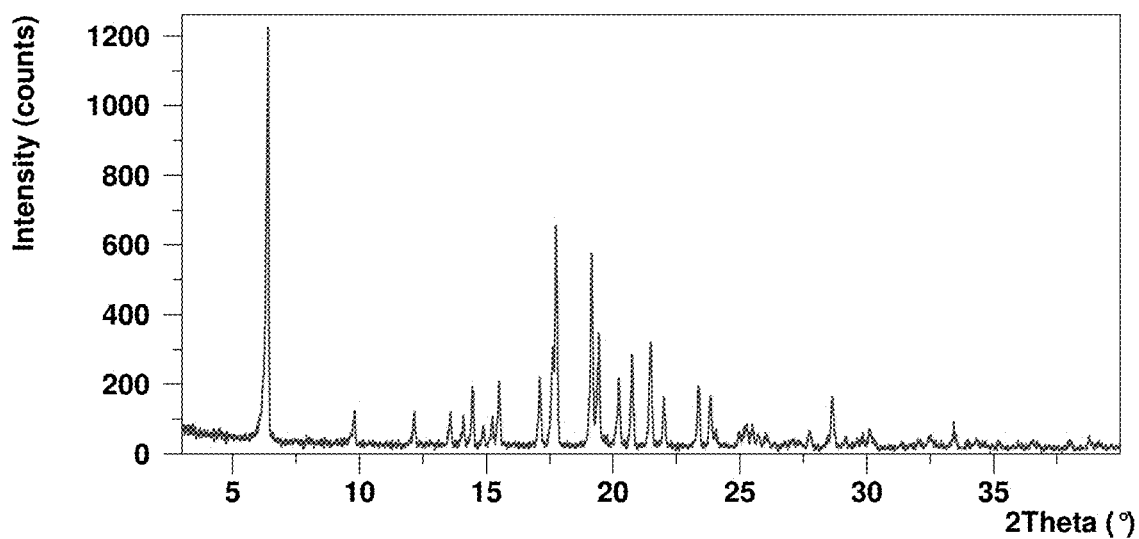
Figure 46: XRPD pattern of esylate salt Form P1 obtained by precipitation in toluene.

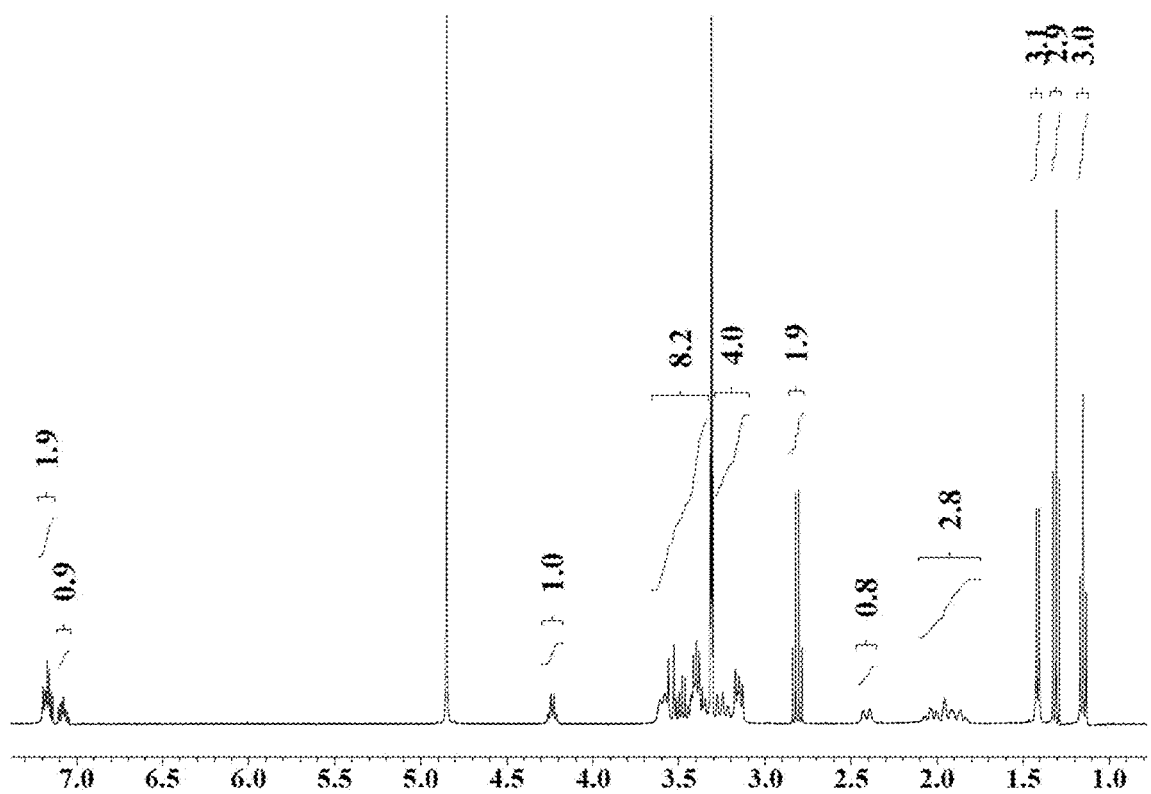
Figure 47: $^1$H-NMR (d4-MeOH, 400 MHz) of esylate salt Form P1.

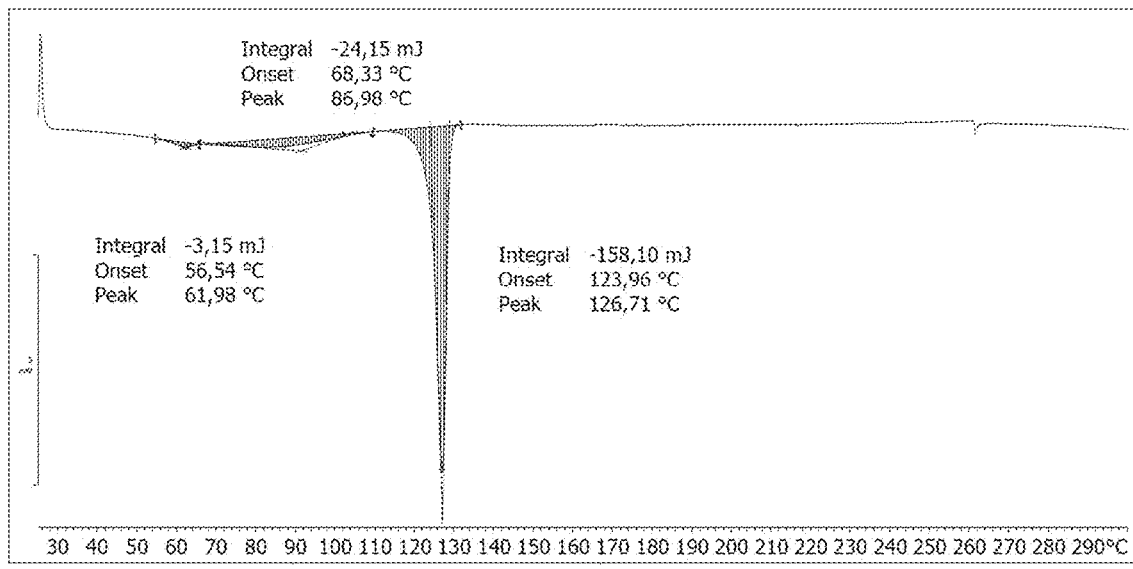
Figure 48: DSC analysis of esylate salt Form P1. Two broad endothermic events at 56 °C and 68 °C are observed prior the melting of the potential esylate salt Form P1 at 124 °C (onset). The nature of the two first events is not clear with the available data.
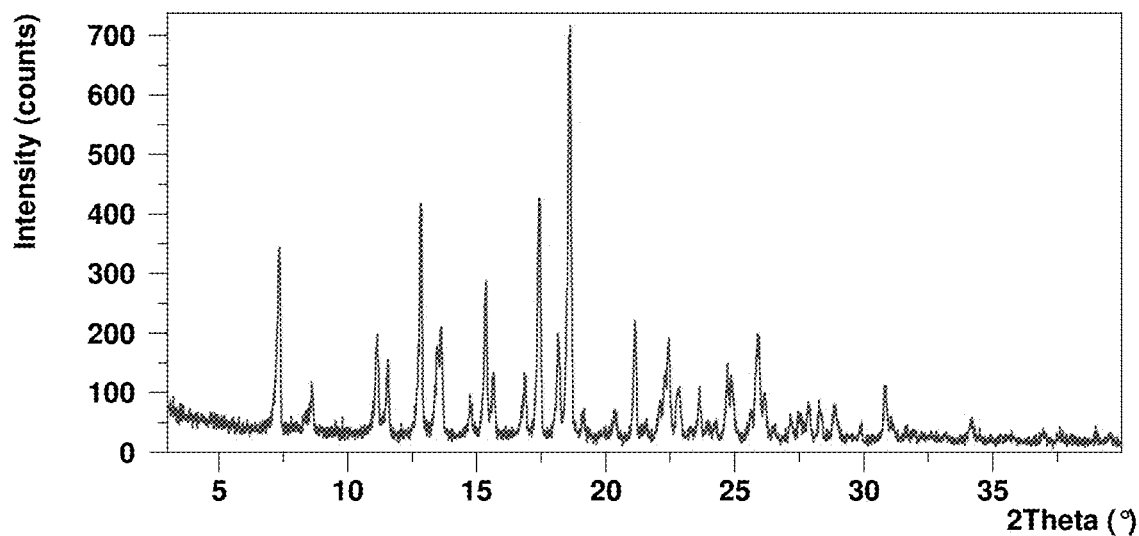
Figure 49: XRPD pattern of nitrate salt Form P1 obtained by precipitation in toluene.

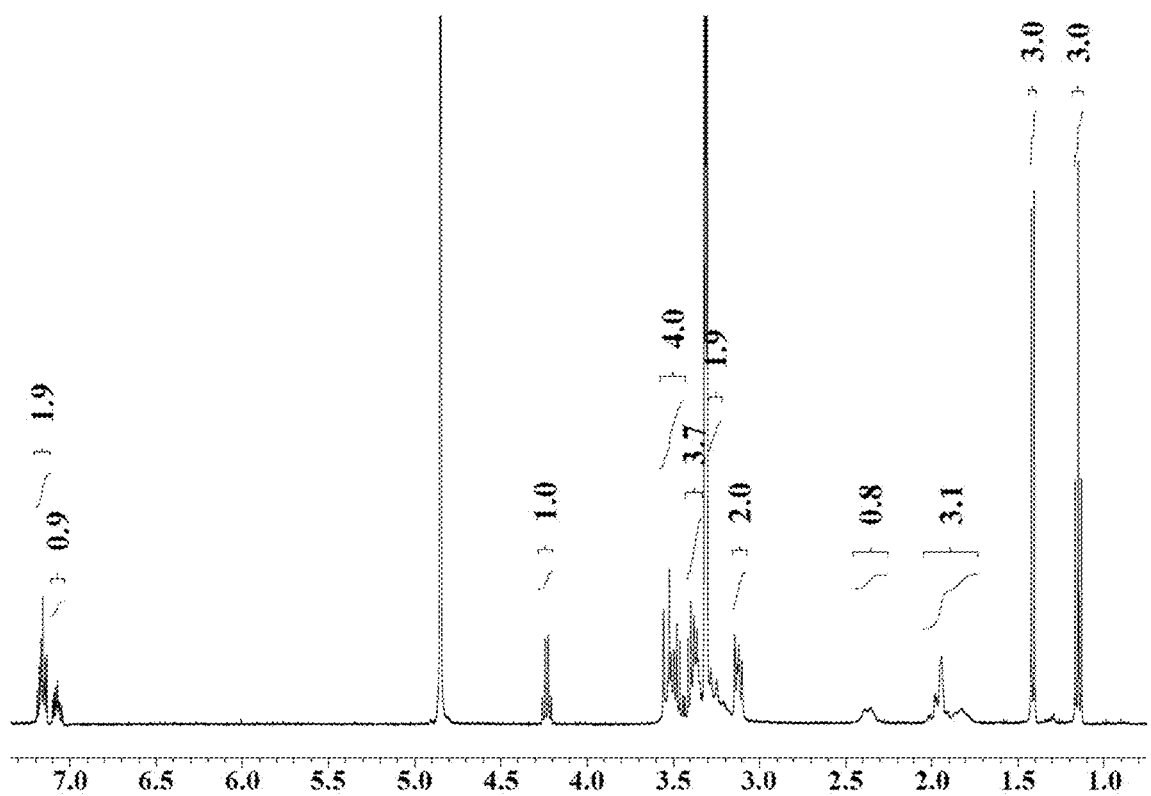
Figure 50: $^1$H-NMR (d4-MeOH, 400 MHz) of nitrate salt Form P1.

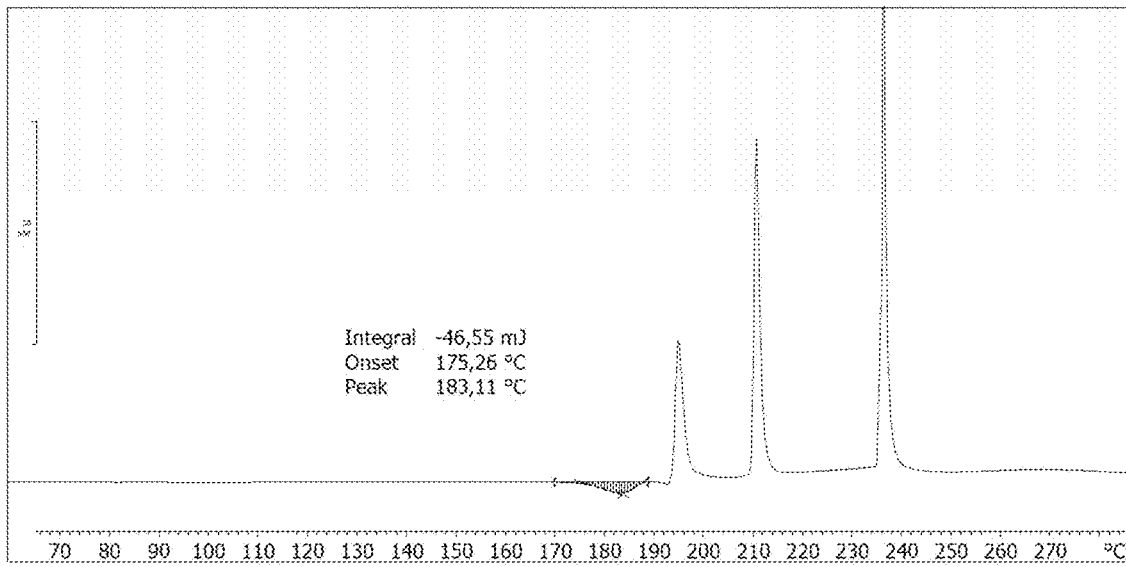
Figure 51: DSC analysis of nitrate salt Form P1. A single endothermic melt is observed at 175 °C (onset) followed by three consecutive exothermic peaks attributed to the decomposition of the compound.
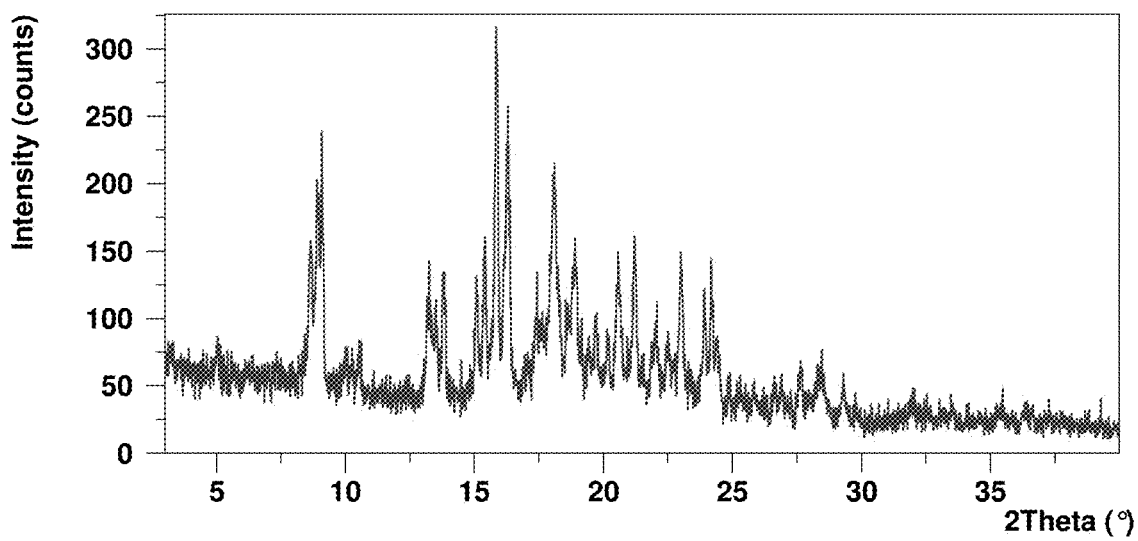
Figure 52: XRPD pattern of (S)-(+)-mandelate salt Form P1 obtained by slow evaporation in MIK.

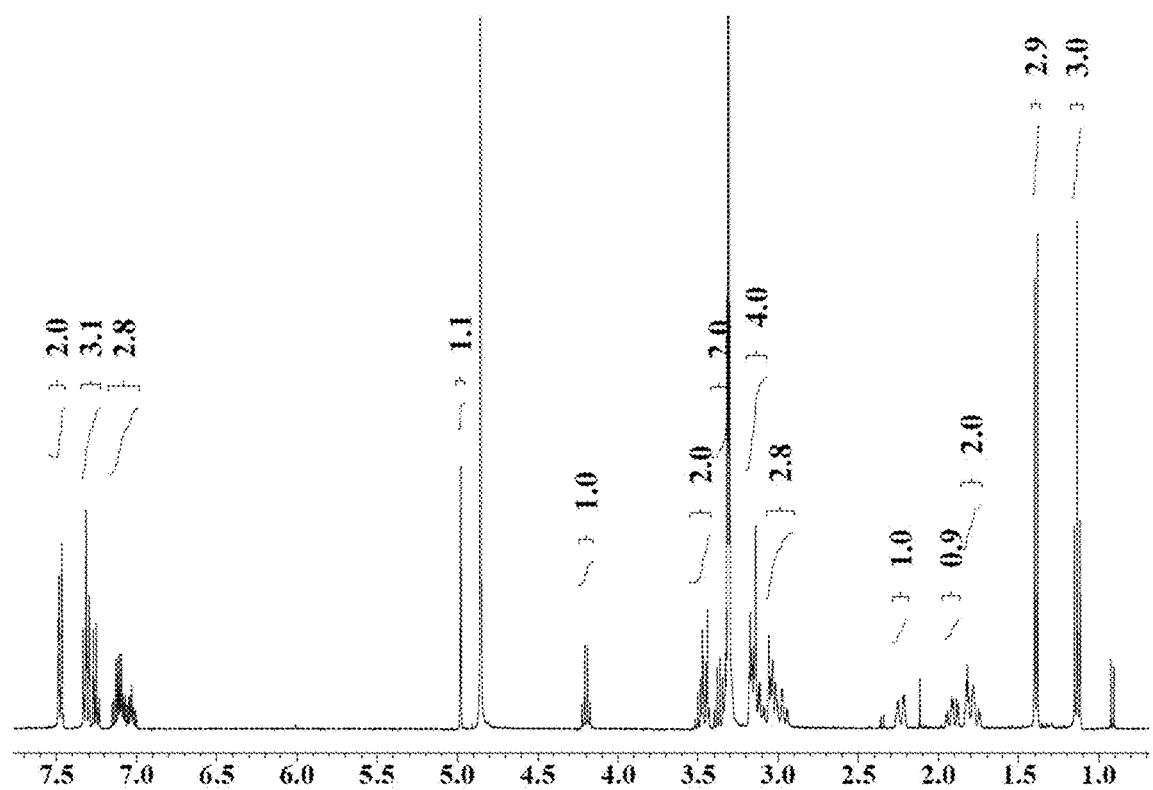
Figure 53: ¹H-NMR (d4-MeOH, 400 MHz) of (S)-(+)-mandelate salt Form P1.

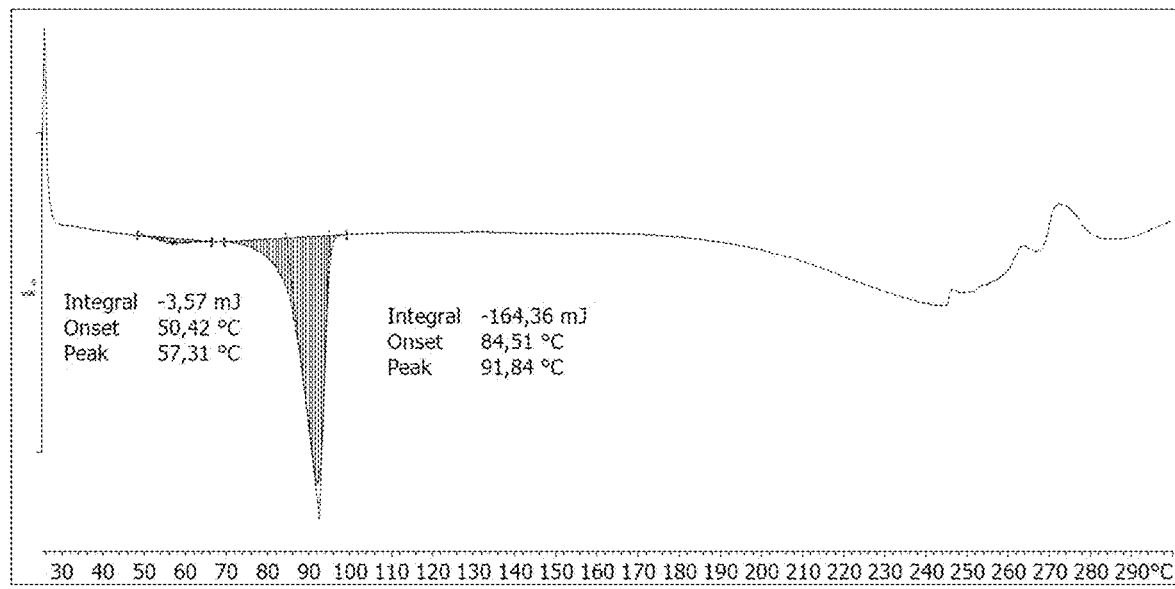
Figure 54: DSC analysis of (S)-(+)-mandelate salt Form P1. A single endothermic melt is observed at 84.5 °C (onset), which might correspond to the melting point of the salt. Such low melting temperature might explain the sticky nature of the solids at ambient temperature.

SALTS OF (R)-9-(2,5-DIFLUOROPHENETHYL)-4-ETHYL-2-METHYL-1-OXA-4,9-DIAZASPIRO [5.5]UNDECAN-3-ONE

FIELD OF THE INVENTION

The present invention relates to salts of (R)-9-(2,5-difluorophenethyl)-4-ethyl-2-methyl-1-oxa-4,9-diazaspiro [5.5]undecan-3-one, specifically to the fumarate, maleate, besylate, succinate, malonate, esylate, (S)-(+)-mandelate, oxalate, nitrate, sulfate, phosphate, hydrochloride and hydrobromide salts, to pharmaceutical compositions comprising them, and to their use in therapy and/or prophylaxis of sigma and/or µ-opioid receptor associated diseases.

BACKGROUND

The adequate management of pain constitutes an important challenge, since currently available treatments provide in many cases only modest improvements, leaving many patients unrelieved [Turk D C, Wilson H D, Cahana A. Treatment of chronic non-cancer pain. *Lancet* 377, 2226-2235 (2011)]. Pain affects a big portion of the population with an estimated prevalence of around 20% and its incidence, particularly in the case of chronic pain, is increasing due to the population ageing. Additionally, pain is clearly related to comorbidities, such as depression, anxiety and insomnia, which lead to important productivity losses and socio-economic burden [Goldberg D S, McGee S J. Pain as a global public health priority. *BMC Public Health.* 11, 770 (2011)]. Existing pain therapies include non-steroidal anti-inflammatory drugs (NSAIDs), opioid agonists, calcium channel blockers and antidepressants, but they are much less than optimal regarding their safety ratio. All of them show limited efficacy and a range of secondary effects that preclude their use, especially in chronic settings.

As mentioned before, there are few available therapeutic classes for the treatment of pain, and opioids are among the most effective, especially when addressing severe pain states. They act through three different types of opioid receptors (mu, kappa and gamma) which are transmembrane G-protein coupled receptors (GPCRs). Still, the main analgesic action is attributed to the activation of the µ-opioid receptor (or mu-opioid receptor or MOR). However, the general administration of MOR agonists is limited due to their important side effects, such as constipation, respiratory depression, tolerance, emesis and physical dependence [Meldrum, M. L. (Ed.). Opioids and Pain Relief: A Historical Perspective. Progress in Pain Research and Management, Vol 25. IASP Press, Seattle, 2003]. Additionally, MOR agonists are not optimal for the treatment of chronic pain as indicated by the diminished effectiveness of morphine against chronic pain conditions. This is especially proven for the chronic pain conditions of neuropathic or inflammatory origin, in comparison to its high potency against acute pain. The finding that chronic pain can lead to MOR down-regulation may offer a molecular basis for the relative lack of efficacy of morphine in long-term treatment settings [Dickenson, A. H., Suzuki, R. *Opioids in neuropathic pain: Clues from animal studies.* Eur J Pain 9, 113-6 (2005)]. Moreover, prolonged treatment with morphine may result in tolerance to its analgesic effects, most likely due to treatment-induced MOR down-regulation, internalization and other regulatory mechanisms. As a consequence, long-term treatment can result in substantial increases in dosing in order to maintain a clinically satisfactory pain relief, but the narrow therapeutic window of MOR agonists finally results in unacceptable side effects and poor patient compliance.

The sigma-1 ($\sigma_1$) receptor was discovered 35 years ago and initially assigned to a new subtype of the opioid family, but later on and based on the studies of the enantiomers of SKF-10,047, its independent nature was established. The first link of the $\sigma_1$ receptor to analgesia was established by Chien and Pasternak [Chien C C, Pasternak G W. Sigma antagonists potentiate opioid analgesia in rats. *Neurosci. Lett.* 190, 137-9 (1995)], who described it as an endogenous anti-opioid system, based on the finding that $\sigma_1$ receptor agonists counteracted opioid receptor mediated analgesia, while σ1 receptor antagonists, such as haloperidol, potentiated it.

Many additional preclinical evidences have indicated a clear role of the $\sigma_1$ receptor in the treatment of pain [Zamanillo D, Romero L, Merlos M, Vela J M. Sigma-1 receptor: A new therapeutic target for pain. *Eur. J. Pharmacol,* 716, 78-93 (2013)]. The development of the $\sigma_1$ receptor knockout mice, which show no obvious phenotype and perceive normally sensory stimuli, was a key milestone in this endeavour. In physiological conditions the responses of the $\sigma_1$ receptor knockout mice to mechanical and thermal stimuli were found to be undistinguishable from WT ones but they were shown to possess a much higher resistance to develop pain behaviors than WT mice when hypersensitivity entered into play. Hence, in the $\sigma_1$ receptor knockout mice capsaicin did not induce mechanical hypersensitivity, both phases of formalin-induced pain were reduced, and cold and mechanical hypersensitivity were strongly attenuated after partial sciatic nerve ligation or after treatment with paclitaxel, which are models of neuropathic pain. Many of these actions were confirmed by the use of $\sigma_1$ receptor antagonists and led to the advancement of one compound, S1RA, into clinical trials for the treatment of different pain states. Compound S1RA exerted a substantial reduction of neuropathic pain and anhedonic state following nerve injury (i.e., neuropathic pain conditions) and, as demonstrated in an operant self-administration model, the nerve-injured mice, but not sham-operated mice, acquired the operant responding to obtain it (presumably to get pain relief), indicating that $\sigma_1$ receptor antagonism relieves neuropathic pain and also address some of the comorbidities (i.e., anhedonia, a core symptom in depression) related to pain states.

Pain is multimodal in nature, since in nearly all pain states several mediators, signaling pathways and molecular mechanisms are implicated. Consequently, monomodal therapies fail to provide complete pain relief. Currently, combining existing therapies is a common clinical practice and many efforts are directed to assess the best combination of available drugs in clinical studies [Mao J, Gold M S, Backonja M. Combination drug therapy for chronic pain: a call for more clinical studies. *J. Pain* 12, 157-166 (2011)]. Hence, there is an urgent need for innovative therapeutics to address this unmet medical need.

As mentioned previously, opioids are among the most potent analgesics but they are also responsible for various adverse effects which seriously limit their use.

Accordingly, there is still a need to find compounds that have an alternative or improved pharmacological activity in the treatment of pain, being both effective and showing the desired selectivity, and having good "drugability" properties, i.e. good pharmaceutical properties related to administration, distribution, metabolism and excretion.

Alkyl derivatives of 1-oxa-4,9-diazaspiro undecane compounds are such promising dual ligands. These compounds and their synthesis are disclosed and claimed in WO 2015185209.

Alkyl derivatives of 1-oxa-4,9-diazaspiro undecane compounds bind to both the μ-opioid receptor and to the $σ_1$ receptor. They display strong analgesic activity in the treatment and prevention of chronic and acute pain, and particularly, neuropathic pain. The compounds have the structural formula:

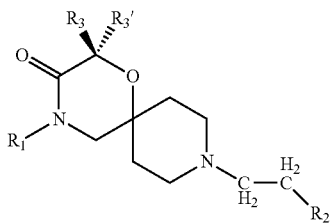

To carry out its pharmaceutical development and take advantage of its potential, there is a need in the art for additional forms of alkyl derivatives of 1-oxa-4,9-diazaspiro undecane compounds that will facilitate the preparation of better formulations of this active pharmaceutical ingredient.

In particular, (R)-9-(2,5-difluorophenethyl)-4-ethyl-2-methyl-1-oxa-4,9-diazaspiro[5.5]undecan-3-one is one of such promising $σ_1$-μ receptor ligands. The compound and its synthesis are disclosed and claimed in WO 2015185209.

(R)-9-(2,5-difluorophenethyl)-4-ethyl-2-methyl-1-oxa-4,9-diazaspiro[5.5] undecan-3-one is a new compound that shows both antagonist affinity for the sigma-1 receptor and agonist affinity for the mu-opioid receptor. However, as a free base is an oily product and hence not convenient for formulation development. The study of salt formation is desirable in order to identify suitable salts that could provide an important advantage to the formulation of this compound.

(R)-9-(2,5-difluorophenethyl)-4-ethyl-2-methyl-1-oxa-4,9-diazaspiro[5.5]undecan-3-one displays strong analgesic activity in the treatment and prevention of chronic and acute pain, and particularly, neuropathic pain. The compound has a molecular weight of 353.1 Da and a pKa of 7.9. The structural formula of the compound is:

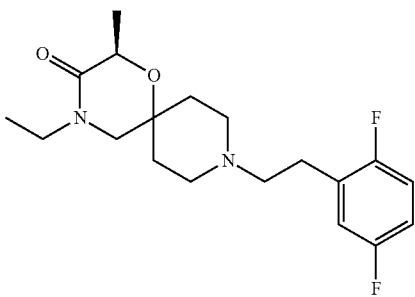 [SMILES: CCN1CC2(CCN(CCc3cc(F)ccc3F)CC2)O[C@H](C)C1=O]

To carry out its pharmaceutical development and take advantage of its potential, there is a need in the art for additional forms of (R)-9-(2,5-difluorophenethyl)-4-ethyl-2-methyl-1-oxa-4,9-diazaspiro[5.5]undecan-3-one that will facilitate the preparation of better formulations of this active pharmaceutical ingredient.

In this regard, alternative forms of the compound may have widely different properties such as, for example, enhanced thermodynamic stability, higher purity or improved bioavailability (e.g. better absorption, dissolution patterns). Specific compound forms could also facilitate the manufacturing (e.g. enhanced flowability), handling and storage (e.g. non-hygroscopic, long shelf life) of the compound formulations or allow the use of a lower dose of the therapeutic agent, thus decreasing its potential side effects. Thus, it is important to provide such forms, having improved properties for pharmaceutical use.

BRIEF DESCRIPTION OF THE INVENTION

In the present invention, after an extensive research on different forms of (R)-9-(2,5-difluorophenethyl)-4-ethyl-2-methyl-1-oxa-4,9-diazaspiro[5.5]undecan-3-one, it has been surprisingly found and demonstrated that some of its salts provide advantageous production, handling, storage and/or therapeutic properties.

Thus, in a first aspect the present invention relates to a (R)-9-(2,5-difluorophenethyl)-4-ethyl-2-methyl-1-oxa-4,9-diazaspiro[5.5]undecan-3-one salt.

Thus, in another aspect the present invention relates to a (R)-9-(2,5-difluorophenethyl)-4-ethyl-2-methyl-1-oxa-4,9-diazaspiro[5.5]undecan-3-one solid salt.

In a further aspect the present invention relates to a (R)-9-(2,5-difluorophenethyl)-4-ethyl-2-methyl-1-oxa-4,9-diazaspiro[5.5]undecan-3-one crystalline salt.

In another aspect the present invention relates to a (R)-9-(2,5-difluorophenethyl)-4-ethyl-2-methyl-1-oxa-4,9-diazaspiro[5.5]undecan-3-one amorphous salt.

In a preferred embodiment, the salt of (R)-9-(2,5-difluorophenethyl)-4-ethyl-2-methyl-1-oxa-4,9-diazaspiro[5.5]undecan-3-one is selected from inorganic acids.

In a preferred embodiment, the salt of (R)-9-(2,5-difluorophenethyl)-4-ethyl-2-methyl-1-oxa-4,9-diazaspiro[5.5]undecan-3-one is selected from organic acids.

In a preferred embodiment, the salt of (R)-9-(2,5-difluorophenethyl)-4-ethyl-2-methyl-1-oxa-4,9-diazaspiro[5.5]undecan-3-one is selected from the group consisting of sulfonic acids.

In a preferred embodiment, the salt of (R)-9-(2,5-difluorophenethyl)-4-ethyl-2-methyl-1-oxa-4,9-diazaspiro[5.5]undecan-3-one is selected from the group consisting of di-acids.

In a still further preferred embodiment, the salt of (R)-9-(2,5-difluorophenethyl)-4-ethyl-2-methyl-1-oxa-4,9-diazaspiro[5.5]undecan-3-one is selected from the group consisting of mono-acids.

A further aspect of the present invention includes pharmaceutical compositions comprising a (R)-9-(2,5-difluorophenethyl)-4-ethyl-2-methyl-1-oxa-4,9-diazaspiro[5.5]undecan-3-one salt and at least a pharmaceutically acceptable carrier, adjuvant or vehicle.

A further aspect of the present invention includes pharmaceutical compositions comprising a (R)-9-(2,5-difluorophenethyl)-4-ethyl-2-methyl-1-oxa-4,9-diazaspiro[5.5]undecan-3-one solid salt and at least a pharmaceutically acceptable carrier, adjuvant or vehicle.

A further aspect of the present invention includes pharmaceutical compositions comprising a (R)-9-(2,5-difluorophenethyl)-4-ethyl-2-methyl-1-oxa-4,9-diazaspiro[5.5]undecan-3-one crystalline salt and at least a pharmaceutically acceptable carrier, adjuvant or vehicle.

A further aspect of the present invention includes pharmaceutical compositions comprising a (R)-9-(2,5-difluorophenethyl)-4-ethyl-2-methyl-1-oxa-4,9-diazaspiro[5.5]undecan-3-one amorphous salt and at least a pharmaceutically acceptable carrier, adjuvant or vehicle.

In a further aspect, the invention is directed to a (R)-9-(2,5-difluorophenethyl)-4-ethyl-2-methyl-1-oxa-4,9-diazaspiro[5.5]undecan-3-one salt for use as medicament, preferably as sigma ligand and/or μ-opioid ligand, i.e., for use in the treatment and/or prophylaxis of a sigma and/or μ-opioid receptor mediated disease or condition.

In a further aspect, the invention is directed to a (R)-9-(2,5-difluorophenethyl)-4-ethyl-2-methyl-1-oxa-4,9-diazaspiro[5.5]undecan-3-one solid salt for use as medicament, preferably as sigma ligand and/or μ-opioid ligand, i.e., for use in the treatment and/or prophylaxis of a sigma and/or μ-opioid receptor mediated disease or condition.

In a further aspect, the invention is directed to a (R)-9-(2,5-difluorophenethyl)-4-ethyl-2-methyl-1-oxa-4,9-diazaspiro[5.5]undecan-3-one crystalline salt for use as medicament, preferably as sigma ligand and/or μ-opioid ligand, i.e., for use in the treatment and/or prophylaxis of a sigma and/or μ-opioid receptor mediated disease or condition.

In a further aspect the invention is directed to a (R)-9-(2,5-difluorophenethyl)-4-ethyl-2-methyl-1-oxa-4,9-diazaspiro[5.5]undecan-3-one amorphous salt for use as medicament, preferably as sigma ligand and/or μ-opioid ligand, i.e., for use in the treatment and/or prophylaxis of a sigma and/or μ-opioid receptor mediated disease or condition.

Another aspect of this invention relates to a method of treating and/or preventing a sigma and/or μ-opioid receptor mediated disease which method comprises administering to a patient in need of such a treatment a therapeutically effective amount of a compound as above defined or a pharmaceutical composition thereof.

The compound according to the invention is a salt of (R)-9-(2,5-difluorophenethyl)-4-ethyl-2-methyl-1-oxa-4,9-diazaspiro[5.5]undecan-3-one solving thereby the above-mentioned problem.

The compound according to the invention is a polymorphic salt of (R)-9-(2,5-difluorophenethyl)-4-ethyl-2-methyl-1-oxa-4,9-diazaspiro[5.5]undecan-3-one solving thereby the above-mentioned problem.

These aspects and preferred embodiments thereof are additionally also defined in the claims.

BRIEF DESCRIPTION OF THE FIGURES

FIG. 1. $^1$H-NMR of (R)-9-(2,5-difluorophenethyl)-4-ethyl-2-methyl-1-oxa-4,9-diazaspiro[5.5]undecan-3-one free base.
FIG. 2. XRPD pattern of hydrochloride salt Form P1
FIG. 3. $^1$H-NMR of hydrochloride salt Form P1
FIG. 4. DSC analysis of hydrochloride salt Form P1
FIG. 5. XRPD pattern of hydrochloride salt Form P2
FIG. 6. $^1$H-NMR of hydrochloride salt Form P2
FIG. 7. DSC analysis of hydrochloride salt Form P2
FIG. 8. XRPD pattern of hydrochloride salt Form P3
FIG. 9. XRPD pattern of fumarate salt Form P1
FIG. 10. $^1$H-NMR of fumarate salt Form P1
FIG. 11. DSC analysis of fumarate salt Form P1
FIG. 12: XRPD pattern of hydrobromide salt Form P1
FIG. 13: $^1$H-NMR of hydrobromide salt Form P1
FIG. 14: DSC analysis of hydrobromide salt Form P1
FIG. 15: XRPD pattern of maleate salt Form P1
FIG. 16: XRPD pattern of maleate salt Form P2
FIG. 17: $^1$H-NMR of maleate salt Form P2
FIG. 18: DSC analysis of maleate salt Form P2
FIG. 19: XRPD pattern of maleate salt Form P3
FIG. 20: $^1$H-NMR of maleate salt Form P3
FIG. 21: DSC analysis of maleate salt Form P3
FIG. 22: XRPD pattern of besylate salt Form P1
FIG. 23: $^1$H-NMR of besylate salt Form P1
FIG. 24: DSC analysis of besylate salt Form P1
FIG. 25: XRPD pattern of besylate salt Form P2
FIG. 26: $^1$H-NMR of besylate salt Form P2
FIG. 27: DSC analysis of besylate salt Form P2
FIG. 28: XRPD pattern of phosphate salt Form P1
FIG. 29: $^1$H-NMR of phosphate salt Form P1
FIG. 30: DSC analysis of phosphate salt Form P1
FIG. 31: XRPD pattern of sulfate salt Form P1.
FIG. 32: $^1$H-NMR of sulfate salt Form P1.
FIG. 33: DSC analysis of sulfate salt Form P1.
FIG. 34: XRPD pattern of succinate salt Form P1
FIG. 35: $^1$H-NMR of succinate salt Form P1
FIG. 36: DSC analysis of succinate salt Form P1
FIG. 37: XRPD pattern of oxalate salt Form P1
FIG. 38: $^1$H-NMR of oxalate salt Form P1
FIG. 39: DSC analysis of oxalate salt Form P1
FIG. 40: XRPD pattern of oxalate salt Form P2
FIG. 41: $^1$H-NMR of oxalate salt Form P2
FIG. 42: DSC analysis of oxalate salt Form P2
FIG. 43: XRPD pattern of malonate salt Form P1
FIG. 44: $^1$H-NMR of malonate salt Form P1
FIG. 45: DSC analysis of malonate salt Form P1
FIG. 46: XRPD pattern of esylate salt Form P1
FIG. 47: $^1$H-NMR of esylate salt Form P1
FIG. 48: DSC analysis of esylate salt Form P1
FIG. 49: XRPD pattern of nitrate salt Form P1
FIG. 50: $^1$H-NMR of nitrate salt Form P1
FIG. 51: DSC analysis of nitrate salt Form P1
FIG. 52: XRPD pattern of (S)-(+)-mandelate salt Form P1
FIG. 53: $^1$H-NMR of (S)-(+)-mandelate salt Form P1
FIG. 54: DSC analysis of (S)-(+)-mandelate salt Form P1

DETAILED DESCRIPTION OF THE INVENTION (R)-9-(2,5-difluorophenethyl)-4-ethyl-2-methyl-1-oxa-4,9-diazaspiro[5.5] undecan-3-one, is a compound that shows both antagonist affinity for the sigma-1 receptor and agonist affinity for the mu-opioid receptor (WO 2015185209). However, (R)-9-(2,5-difluorophenethyl)-4-ethyl-2-methyl-1-oxa-4,9-diazaspiro[5.5] undecan-3-one as a free base is an oily product and hence not convenient for formulation development. The study of salt formation is desirable in order to identify suitable salts that could provide an important advantage to the formulation of this compound.

The new "salts", in particular solid salts, of a pharmaceutical compound provides an opportunity to improve the physical or performance characteristics of a pharmaceutical product in that it enlarges the repertoire of materials that a formulation scientist has available for designing, for example, a pharmaceutical dosage form of a drug with a targeted release profile or other desired characteristics.

In this particular case there is a need in the art for additional forms of (R)-9-(2,5-difluorophenethyl)-4-ethyl-2-methyl-1-oxa-4,9-diazaspiro[5.5]undecan-3-one to carry out its pharmaceutical development and release its potential, and facilitate the preparation of better formulations of this active pharmaceutical ingredient. In particular, (R)-9-(2,5-difluorophenethyl)-4-ethyl-2-methyl-1-oxa-4,9-diazaspiro[5.5]undecan-3-one, as the free base, is an oily product and thus not suitable for development. In this regard, different salts, in particular solid salts, of the compound may provide a substantial improvement in handling and may as well have widely different properties such as, for example, enhanced thermodynamic stability, higher purity or improved bioavailability (e.g. better absorption, dissolution patterns) and could either become intermediates for other forms or provide in themselves a still better formulation of this active pharmaceutical ingredient. Specific compound forms could also facilitate the manufacturing (e.g. enhanced flowability), handling and storage (e.g. non-hygroscopic, long shelf life) of the compound formulations or allow the use of a lower dose of the therapeutic agent, thus decreasing its potential side effects. Thus, it is important to find such forms, having desirable properties for pharmaceutical use.

The inventors of the present invention have surprisingly found and demonstrated that new salts, in particular solid salts, of (R)-9-(2,5-difluorophenethyl)-4-ethyl-2-methyl-1-oxa-4,9-diazaspiro[5.5]undecan-3-one may achieve one or more of the above mentioned objectives. The novel salts, in particular solid salts, of (R)-9-(2,5-difluorophenethyl)-4-ethyl-2-methyl-1-oxa-4,9-diazaspiro[5.5]undecan-3-one herein disclosed are fairly stable over the time and have good flow and dissolution characteristics. Particularly, novel and highly stable salts, in particular solid salts, of the compound provide advantageous production, handling, storage and therapeutic properties.

Thus, the present invention relates to salts, in particular solid salts, of (R)-9-(2,5-difluorophenethyl)-4-ethyl-2-methyl-1-oxa-4,9-diazaspiro[5.5]undecan-3-one, to their use and to several processes for their preparation.

The inventors of the present invention, after an extensive research on different forms of (R)-9-(2,5-difluorophenethyl)-4-ethyl-2-methyl-1-oxa-4,9-diazaspiro[5.5]undecan-3-one, have additionally and surprisingly found and demonstrated that most of its salts, in particular solid salts, provide advantageous production, handling, storage and/or therapeutic properties.

For example, it is surprisingly found and demonstrated that some of the salts, in particular solid salts, of (R)-9-(2,5-difluorophenethyl)-4-ethyl-2-methyl-1-oxa-4,9-diazaspiro[5.5]undecan-3-one and specifically the hydrogen halides salts and simple carboxylic diacid salts provides advantageous production, handling, storage and/or therapeutic properties.

Further, among the acids suitable for obtaining a salt in solid form, it has been surprisingly found that the strong inorganic monoacids and the organic diacids provided good results in terms of easiness of preparation, physical stability, scaling-up, solubility, etc. This is particularly true for hydrochloride, hydrobromide, phosphate, sulfate, nitrate, fumarate, maleate, succinate, oxalate and malonate. These results are shown through the increment achieved regarding the melting point and the values for some specific properties as thermodynamic solubility or pharmacokinetic parameters as Cmax or AUC in order to find new alternative forms having desirable properties for pharmaceutical use.

For clarity reasons, the salts of the present invention are sometimes referring to as the corresponding acid or as the salt as such. There are two different ways of describing the same product. For example, malonate salts are also referring to salts of malonic acid or malonic salts, oxalate salts to salts of oxalic acid or oxalic salts, succinate salts to salts of succinic acid or succinic salts, etc.

Thus, in a first aspect, the present invention is directed to a (R)-9-(2,5-difluorophenethyl)-4-ethyl-2-methyl-1-oxa-4,9-diazaspiro[5.5]undecan-3-one salt.

Thus, in another aspect the present invention relates to a (R)-9-(2,5-difluorophenethyl)-4-ethyl-2-methyl-1-oxa-4,9-diazaspiro[5.5]undecan-3-one solid salt.

In another aspect the present invention relates to (R)-9-(2,5-difluorophenethyl)-4-ethyl-2-methyl-1-oxa-4,9-diazaspiro[5.5]undecan-3-one crystalline salts.

In another aspect the present invention relates to (R)-9-(2,5-difluorophenethyl)-4-ethyl-2-methyl-1-oxa-4,9-diazaspiro[5.5]undecan-3-one amorphous salts.

In a preferred embodiment, the salt of (R)-9-(2,5-difluorophenethyl)-4-ethyl-2-methyl-1-oxa-4,9-diazaspiro[5.5]undecan-3-one is selected from the group consisting of inorganic acids.

In a preferred embodiment, the salt of (R)-9-(2,5-difluorophenethyl)-4-ethyl-2-methyl-1-oxa-4,9-diazaspiro[5.5]undecan-3-one is selected from organic acids.

In a preferred embodiment, the salt of (R)-9-(2,5-difluorophenethyl)-4-ethyl-2-methyl-1-oxa-4,9-diazaspiro[5.5]undecan-3-one is selected from the group consisting of sulfonic acids.

In a preferred embodiment, the salt of (R)-9-(2,5-difluorophenethyl)-4-ethyl-2-methyl-1-oxa-4,9-diazaspiro[5.5]undecan-3-one is selected from the group consisting of di-acids.

In a preferred embodiment, the salt of (R)-9-(2,5-difluorophenethyl)-4-ethyl-2-methyl-1-oxa-4,9-diazaspiro[5.5]undecan-3-one is selected from the group consisting of mono-acids.

In a preferred embodiment, the salt of (R)-9-(2,5-difluorophenethyl)-4-ethyl-2-methyl-1-oxa-4,9-diazaspiro[5.5]undecan-3-one is selected from hydrochloride, fumarate, hydrobromide, maleate, phosphate, sulfate, succinate, oxalate, malonate, mesylate, esylate, besylate, nitrate, and (S)-(+)-mandelate.

In a preferred embodiment, the salt of (R)-9-(2,5-difluorophenethyl)-4-ethyl-2-methyl-1-oxa-4,9-diazaspiro[5.5]undecan-3-one is selected from hydrochloride, fumarate, hydrobromide, maleate, phosphate, sulfate, succinate, oxalate, malonate, mesylate, esylate, besylate and nitrate.

In a preferred embodiment, the salt of (R)-9-(2,5-difluorophenethyl)-4-ethyl-2-methyl-1-oxa-4,9-diazaspiro[5.5]undecan-3-one is selected from hydrochloride, hydrobromide, phosphate, sulfate and nitrate.

In a preferred embodiment, the salt of (R)-9-(2,5-difluorophenethyl)-4-ethyl-2-methyl-1-oxa-4,9-diazaspiro[5.5]undecan-3-one is selected from fumarate, maleate, succinate, oxalate, malonate, mesylate, esylate, besylate and (S)-(+)-mandelate.

In a preferred embodiment, the salt of (R)-9-(2,5-difluorophenethyl)-4-ethyl-2-methyl-1-oxa-4,9-diazaspiro[5.5]undecan-3-one is selected from mesylate, esylate and besylate.

In a preferred embodiment, the salt of (R)-9-(2,5-difluorophenethyl)-4-ethyl-2-methyl-1-oxa-4,9-diazaspiro[5.5]undecan-3-one is selected from fumarate, maleate, succinate, oxalate and malonate.

In a preferred embodiment, the salt of (R)-9-(2,5-difluorophenethyl)-4-ethyl-2-methyl-1-oxa-4,9-diazaspiro[5.5]undecan-3-one is selected from fumarate, maleate, succinate, oxalate and malonate.

In a preferred embodiment, the salt of (R)-9-(2,5-difluorophenethyl)-4-ethyl-2-methyl-1-oxa-4,9-diazaspiro[5.5]undecan-3-one is selected from mesylate, esylate, besylate and (S)-(+)-mandelate.

In a preferred embodiment, the salt of (R)-9-(2,5-difluorophenethyl)-4-ethyl-2-methyl-1-oxa-4,9-diazaspiro[5.5]undecan-3-one is selected from mesylate, esylate and besylate.

In a preferred embodiment, the salt of (R)-9-(2,5-difluorophenethyl)-4-ethyl-2-methyl-1-oxa-4,9-diazaspiro[5.5]undecan-3-one is (S)-(+)-mandelate.

In a preferred embodiment, the salt of (R)-9-(2,5-difluorophenethyl)-4-ethyl-2-methyl-1-oxa-4,9-diazaspiro[5.5]undecan-3-one is selected from hydrochloride, fumarate, hydrobromide, maleate, phosphate, sulfate, succinate, oxalate, malonate, mesylate, esylate, besylate and nitrate.

In a preferred embodiment, the salt of (R)-9-(2,5-difluorophenethyl)-4-ethyl-2-methyl-1-oxa-4,9-diazaspiro[5.5]undecan-3-one is selected from hydrochloride, fumarate, hydrobromide, maleate, phosphate, sulfate, succinate, oxalate, malonate, mesylate, esylate, besylate, nitrate and (S)-(+)-mandelate.

In a preferred embodiment, the salt of (R)-9-(2,5-difluorophenethyl)-4-ethyl-2-methyl-1-oxa-4,9-diazaspiro[5.5]undecan-3-one is selected from hydrochloride, fumarate, hydrobromide, maleate, phosphate, sulfate, succinate, oxalate, malonate, mesylate, esylate, besylate, nitrate and (S)-(+)-mandelate.

In a preferred embodiment, the salt of (R)-9-(2,5-difluorophenethyl)-4-ethyl-2-methyl-1-oxa-4,9-diazaspiro[5.5]undecan-3-one is selected from hydrochloride, fumarate, hydrobromide, maleate, phosphate, sulfate, succinate, oxalate, malonate, mesylate, esylate, besylate and nitrate.

In a preferred embodiment, the salt of (R)-9-(2,5-difluorophenethyl)-4-ethyl-2-methyl-1-oxa-4,9-diazaspiro[5.5]undecan-3-one is selected from mesylate.

In a preferred embodiment, the salt of (R)-9-(2,5-difluorophenethyl)-4-ethyl-2-methyl-1-oxa-4,9-diazaspiro[5.5]undecan-3-one is not the hydrochloride salt.

In a preferred embodiment, the salt of (R)-9-(2,5-difluorophenethyl)-4-ethyl-2-methyl-1-oxa-4,9-diazaspiro[5.5]undecan-3-one is the hydrochloride salt.

In a preferred embodiment, the salt of (R)-9-(2,5-difluorophenethyl)-4-ethyl-2-methyl-1-oxa-4,9-diazaspiro[5.5]undecan-3-one is the hydrobromide salt.

In a preferred embodiment, the salt of (R)-9-(2,5-difluorophenethyl)-4-ethyl-2-methyl-1-oxa-4,9-diazaspiro[5.5]undecan-3-one is the fumarate salt.

In a preferred embodiment, the salt of (R)-9-(2,5-difluorophenethyl)-4-ethyl-2-methyl-1-oxa-4,9-diazaspiro[5.5]undecan-3-one is the maleate salt.

In a preferred embodiment, the salt of (R)-9-(2,5-difluorophenethyl)-4-ethyl-2-methyl-1-oxa-4,9-diazaspiro[5.5]undecan-3-one is the besylate salt.

In a preferred embodiment, the salt of (R)-9-(2,5-difluorophenethyl)-4-ethyl-2-methyl-1-oxa-4,9-diazaspiro[5.5]undecan-3-one is the phosphate salt.

In a preferred embodiment, the salt of (R)-9-(2,5-difluorophenethyl)-4-ethyl-2-methyl-1-oxa-4,9-diazaspiro[5.5]undecan-3-one is the sulfate salt.

In a preferred embodiment, the salt of (R)-9-(2,5-difluorophenethyl)-4-ethyl-2-methyl-1-oxa-4,9-diazaspiro[5.5]undecan-3-one is the succinate salt.

In a preferred embodiment, the salt of (R)-9-(2,5-difluorophenethyl)-4-ethyl-2-methyl-1-oxa-4,9-diazaspiro[5.5]undecan-3-one is the oxalate salt.

In a preferred embodiment, the salt of (R)-9-(2,5-difluorophenethyl)-4-ethyl-2-methyl-1-oxa-4,9-diazaspiro[5.5]undecan-3-one is the malonate salt.

In a preferred embodiment, the salt of (R)-9-(2,5-difluorophenethyl)-4-ethyl-2-methyl-1-oxa-4,9-diazaspiro[5.5]undecan-3-one is the esylate salt.

In a preferred embodiment, the salt of (R)-9-(2,5-difluorophenethyl)-4-ethyl-2-methyl-1-oxa-4,9-diazaspiro[5.5]undecan-3-one is the nitrate salt.

In a preferred embodiment, the salt of (R)-9-(2,5-difluorophenethyl)-4-ethyl-2-methyl-1-oxa-4,9-diazaspiro[5.5]undecan-3-one is the (S)-(+)-mandelate salt.

As noted previously, it has been reported that (R)-9-(2,5-difluorophenethyl)-4-ethyl-2-methyl-1-oxa-4,9-diazaspiro[5.5]undecan-3-one is a selective sigma-1 ($\sigma_1$) receptor antagonist and/or µ-opioid receptor agonist, displaying strong analgesic activity in the treatment and prevention of pain (see WO 2015185209).

It has now been found that the (R)-9-(2,5-difluorophenethyl)-4-ethyl-2-methyl-1-oxa-4,9-diazaspiro[5.5]undecan-3-one salts according to the present invention are particularly suitable for use as medicament.

In a preferred embodiment the invention relates to (R)-9-(2,5-difluorophenethyl)-4-ethyl-2-methyl-1-oxa-4,9-diazaspiro[5.5]undecan-3-one salts for use as a medicament.

In a preferred embodiment the invention relates to (R)-9-(2,5-difluorophenethyl)-4-ethyl-2-methyl-1-oxa-4,9-diazaspiro[5.5]undecan-3-one salts for the manufacture of a medicament.

In a preferred embodiment the invention relates to (R)-9-(2,5-difluorophenethyl)-4-ethyl-2-methyl-1-oxa-4,9-diazaspiro[5.5]undecan-3-one salts for use in the manufacture of a medicament.

In a preferred embodiment the invention relates to (R)-9-(2,5-difluorophenethyl)-4-ethyl-2-methyl-1-oxa-4,9-diazaspiro[5.5]undecan-3-one salts for use in the treatment and/or prophylaxis of pain.

In a preferred embodiment the invention relates to (R)-9-(2,5-difluorophenethyl)-4-ethyl-2-methyl-1-oxa-4,9-diazaspiro[5.5]undecan-3-one salts for use in the treatment and/or prophylaxis of medium to severe pain, visceral pain, chronic pain, cancer pain, migraine, inflammatory pain, acute pain or neuropathic pain, allodynia or hyperalgesia, also preferably including mechanical allodynia or thermal hyperalgesia.

In a preferred embodiment the invention relates to a method for the treatment and/or prophylaxis of pain, said method comprises administering to a patient in need a (R)-9-(2,5-difluorophenethyl)-4-ethyl-2-methyl-1-oxa-4,9-diazaspiro[5.5]undecan-3-one salt.

In a preferred embodiment the invention relates to a method for the treatment and/or prophylaxis of medium to severe pain, visceral pain, chronic pain, cancer pain, migraine, inflammatory pain, acute pain or neuropathic pain, allodynia or hyperalgesia, also preferably including mechanical allodynia or thermal hyperalgesia, said method comprises administering to a patient in need a (R)-9-(2,5-difluorophenethyl)-4-ethyl-2-methyl-1-oxa-4,9-diazaspiro[5.5]undecan-3-one salt.

In a preferred embodiment the invention relates to (R)-9-(2,5-difluorophenethyl)-4-ethyl-2-methyl-1-oxa-4,9-diazaspiro[5.5]undecan-3-one salts, for the manufacture of a medicament for the treatment and/or prophylaxis of pain.

In a preferred embodiment the invention relates to (R)-9-(2,5-difluorophenethyl)-4-ethyl-2-methyl-1-oxa-4,9-diazaspiro[5.5]undecan-3-one salts, for the manufacture of a medicament for the treatment and/or prophylaxis of medium to severe pain, visceral pain, chronic pain, cancer pain, migraine, inflammatory pain, acute pain or neuropathic pain, allodynia or hyperalgesia, also preferably including mechanical allodynia or thermal hyperalgesia.

In a preferred embodiment the invention relates to (R)-9-(2,5-difluorophenethyl)-4-ethyl-2-methyl-1-oxa-4,9-diazaspiro[5.5]undecan-3-one salts for use in the manufacture of a medicament for the treatment and/or prophylaxis of pain.

In a preferred embodiment the invention relates to (R)-9-(2,5-difluorophenethyl)-4-ethyl-2-methyl-1-oxa-4,9-diazaspiro[5.5]undecan-3-one salts for use in the manufacture of a medicament for the treatment and/or prophylaxis of medium to severe pain, visceral pain, chronic pain, cancer pain, migraine, inflammatory pain, acute pain or neuropathic pain, allodynia or hyperalgesia, also preferably including mechanical allodynia or thermal hyperalgesia.

The present invention therefore further provides medicaments or pharmaceutical compositions comprising a (R)-9-(2,5-difluorophenethyl)-4-ethyl-2-methyl-1-oxa-4,9-diazaspiro[5.5]undecan-3-one salt together with at least a pharmaceutically acceptable carrier, adjuvant, or vehicle, for administration to a patient.

Examples of pharmaceutical compositions include any solid (tablets, pills, capsules, granules etc.) or liquid (solutions, suspensions or emulsions) composition for oral, topical or parenteral administration.

In a preferred embodiment the pharmaceutical compositions are in oral form, either solid or liquid. Suitable dose forms for oral administration may be tablets, capsules, syrops or solutions and may contain conventional excipients known in the art such as binding agents, for example syrup, acacia, gelatin, sorbitol, tragacanth, or polyvinylpyrrolidone; fillers, for example lactose, sugar, maize starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulfate.

The solid oral compositions may be prepared by conventional methods of blending, filling or tabletting. Repeated blending operations may be used to distribute the active agent throughout those compositions employing large quantities of fillers. Such operations are conventional in the art. The tablets may for example be prepared by wet or dry granulation and optionally coated according to methods well known in normal pharmaceutical practice, in particular with an enteric coating.

The pharmaceutical compositions may also be adapted for parenteral administration, such as sterile solutions, suspensions or lyophilized products in the appropriate unit dosage form. Adequate excipients can be used, such as bulking agents, buffering agents or surfactants.

Administration of the compounds or compositions of the present invention may be by any suitable method, such as intravenous infusion, oral preparations, and intraperitoneal and intravenous administration. Oral administration is preferred because of the convenience for the patient and the chronic character of the diseases to be treated.

The compounds and compositions of this invention may be used with other drugs to provide a combination therapy. The other drugs may form part of the same composition, or be provided as a separate composition for administration at the same time or at different time.

The auxiliary materials or additives of a pharmaceutical composition according to the present invention can be selected among carriers, excipients, support materials, lubricants, fillers, solvents, diluents, colorants, flavour conditioners such as sugars, antioxidants, binders, adhesives, disintegrants, anti-adherents, glidants and/or agglutinants. In the case of suppositories, this may imply waxes or fatty acid esters or preservatives, emulsifiers and/or carriers for parenteral application. The selection of these auxiliary materials and/or additives and the amounts to be used will depend on the form of application of the pharmaceutical composition.

The medicament or pharmaceutical composition according to the present invention may be in any form suitable for the application to humans and/or animals, preferably humans including infants, children and adults and can be produced by standard procedures known to those skilled in the art. Therefore, the formulation in accordance with the invention may be adapted for topical or systemic application, particularly for dermal, transdermal, subcutaneous, intramuscular, intra-articular, intraperitoneal, intravenous, intra-arterial, intravesical, intraosseous, intracavernosal, pulmonary, buccal, sublingual, ocular, intravitreal, intranasal, percutaneous, rectal, vaginal, oral, epidural, intrathecal, intraventricular, intracerebral, intracerebroventricular, intra cisternal, intraspinal, perispinal, intracranial, delivery via needles or catheters with or without pump devices, or other application routes.

The mentioned formulations will be prepared using standard methods such as those described or referred to in the Spanish and US Pharmacopoeias and similar reference texts.

In one embodiment of the invention the (R)-9-(2,5-difluorophenethyl)-4-ethyl-2-methyl-1-oxa-4,9-diazaspiro[5.5]undecan-3-one salts are used in therapeutically effective amounts.

Generally an effective administered amount of a compound of the invention will depend on the relative efficacy of the compound chosen, the severity of the disorder being treated and the weight of the sufferer. The physician will determine the dosage of the present therapeutic agents which will be most suitable and it will vary with the form of administration and the particular compound chosen, and furthermore, it will vary with the patient under treatment, the age of the patient, the type of disease or condition being treated. When the composition is administered orally, larger quantities of the active agent will be required to produce the same effect as a smaller quantity given parenterally. The active compound will typically be administered once or more times a day for example 1, 2, 3 or 4 times daily, with typical total daily doses in the range of from 0.1 to 1000 mg/kg/day.

Particularly, the (R)-9-(2,5-difluorophenethyl)-4-ethyl-2-methyl-1-oxa-4,9-diazaspiro[5.5]undecan-3-one salts are useful for the treatment and/or prophylaxis of a sigma receptor and/or µ-opioid receptor mediated disease or condition.

In a preferred embodiment, all the salts according to the present invention are useful for the treatment and/or prophylaxis of a sigma receptor and/or µ-opioid receptor mediated disease or condition, preferably all the salts according to the present invention are useful for the treatment and/or prophylaxis of a sigma receptor and µ-opioid receptor mediated disease or condition.

In order to obtain new salts of (R)-9-(2,5-difluorophenethyl)-4-ethyl-2-methyl-1-oxa-4,9-diazaspiro[5.5]undecan-3-one, which is an oily product not suitable for development, several acids were selected according to the following criteria:

Acids with enough acidity to protonate the free base
Acids that are pharmaceutically acceptable compounds
The General Procedure to Prepare the Salts was as Follows:
(R)-9-(2,5-difluorophenethyl)-4-ethyl-2-methyl-1-oxa-4,9-diazaspiro[5.5]undecan-3-one and ca. 1 eq. of the corresponding acidic counter-ion were mixed and solvent was added to obtain a clear solution or a suspension.
When a suspension was obtained (slurry), the mixture was stirred between rt and 40° C. overnight.

When a clear solution was prepared, the solution was either cooled down (0-20° C.) to obtain a precipitated solid (precipitation) or evaporated to dryness under ambient conditions or with a rotavapor (evaporation).

In all cases, the recovered solids were isolated by centrifugation and dried prior XRPD analysis. Optionally, ultrasounds were used in order to help dissolving the reagents.

The results obtained with different acids and conditions are depicted in Table 1.

TABLE 1

Experimental data of the salt formation experiments with ca. 1 eq. of acid.

| Acid | Solvent | Acid solution | Method | Observation |
|---|---|---|---|---|
| Hydrochloric acid | Water | aq. 1M HCl | Precipitation | Off-white solid |
| | MIK | aq. 1M HCl | Precipitation | Off-white solid |
| | THF | aq. 1M HCl | Evaporation | Off-white solid |
| | Toluene | aq.1M HCl 1M | Evaporation | Off-white solid |
| | IPA | 1.25M HCl IPA | Precipitation | Off-white solid |
| | DCM | 1.25M HCl IPA | Evaporation | Off-white solid |
| | MeOH | 1.25M HCl MeOH | Evaporation | Off-white solid |
| | Xylene | 1.25M HCl MeOH | Evaporation | Off-white solid |
| | EtOH | 1.25M HCl EtOH | Precipitation | Off-white solid |
| | TBME | 1.25M HCl EtOH | Precipitation | Off-white solid |
| | Dioxane | 4M HCl Dioxane | Precipitation | Off-white solid |
| | AcOEt | 4M HCl Dioxane | Precipitation | Off-white solid |
| | AcOEt | 1.25M HCl MeOH | Evaporation | Off-white solid |
| | Heptane | 1.25M HCl IPA | Precipitation | Off-white solid |
| | Et₂O | aq. 1M HCl | Evaporation | Off-white solid |
| | CHCl₃ | 1.25M HCl MeOH | Evaporation | Off-white solid |
| | THF | 1.25M HCl EtOH | Precipitation | Off-white solid |
| | DCM | 1.25M HCl IPA | Evaporation | Off-white solid |
| | DCM | 1.25M HCl IPA | Evaporation | Off-white solid |
| Fumaric acid | MIK | — | Slurry | Off-white solid |
| | Toluene | — | Slurry | Off-white solid |
| | MeOH/DCM | — | Evaporation | Off-white solid |
| | THF/MeOH | — | Evaporation | Off-white solid |
| | EtOH/THF | — | Slurry | Off-white solid |
| | THF/EtOH | — | Slurry | Off-white solid |
| | ACN/THF | — | Slurry | Off-white solid |
| | TBME/ACN | — | Slurry | Off-white solid |
| Hydrobromic acid | IPA | — | Precipitation | Off-white solid |
| | MIK | — | Precipitation | Off-white solid |
| | THF | — | Precipitation | Off-white solid |
| | THF | — | Precipitation | Off-white solid |
| | Water | — | Evaporation | Off-white solid |
| Maleic acid | IPA | — | Precipitation | White solid |
| | MIK | — | Slurry | White solid |
| | Toluene | — | Slurry | White solid |
| | IPA | — | Precipitation | White solid |
| | MIK | — | Slurry | White solid |
| | Water | — | Evaporation | White solid |
| Benzenesulfonic acid | IPA | — | Precipitation | White solid |
| | MIK | — | Precipitation | White solid |
| | THF | — | Precipitation | White solid |
| | Toluene | — | Precipitation | White solid |
| | IPA | — | Precipitation | White solid |
| | Water | — | Evaporation | Off-white solid |
| Phosphoric acid | IPA | — | Precipitation | White solid |
| | MIK | — | Precipitation | White solid |
| | THF | — | Precipitation | White solid |
| Sulfuric acid | IPA | — | Precipitation | White solid |
| | MIK | — | Precipitation | White solid |
| | THF | — | Precipitation | White solid |
| Succinic acid | IPA | — | Precipitation | White solid |
| | MIK | — | Slurry | White solid |
| | THF | — | Evaporation | White solid |
| | Toluene | — | Evaporation | White solid |
| Oxalic acid | Water | — | Precipitation | White solid |
| | IPA | — | Precipitation | White solid |
| | MIK | — | Precipitation | White solid |
| | THF | — | Precipitation | White solid |
| | Toluene | — | Slurry | White solid |
| Malonic acid | IPA | — | Precipitation | White solid |
| | MIK | — | Precipitation | White solid |
| | THF | — | Precipitation | White solid |
| | Toluene | — | Evaporation | White solid |
| Methanesulfonic acid | Toluene | — | Precipitation | White solid |
| Ethanesulfonic acid | Toluene | — | Precipitation | Off-white solid |
| | Water | — | Evaporation | Off-white solid |
| | MIK | — | Evaporation | Off-white solid |
| | THF | — | Evaporation | Off-white solid |
| Nitric acid | Water | — | Precipitation | White solid |
| | IPA | — | Precipitation | White solid |
| | MIK | — | Precipitation | White solid |
| | THF | — | Precipitation | White solid |
| | Toluene | — | Precipitation | White solid |
| (S)-(+)-Mandelic acid | MIK | — | Evaporation | White solid |

Some of the salts, in particular solid salts, of (R)-9-(2,5-difluorophenethyl)-4-ethyl-2-methyl-1-oxa-4,9-diazaspiro[5.5]undecan-3-one may present the additional advantage of being useful for the obtention of other forms such as the crystalline forms of (R)-9-(2,5-difluorophenethyl)-4-ethyl-2-methyl-1-oxa-4,9-diazaspiro[5.5]undecan-3-one salts.

The inventors of the present invention have also surprisingly found and demonstrated that the novel amorphous and crystalline salts of (R)-9-(2,5-difluorophenethyl)-4-ethyl-2-methyl-1-oxa-4,9-diazaspiro[5.5]undecan-3-one herein disclosed are fairly stable over the time and have good flow and dissolution characteristics. Particularly, a novel and highly stable amorphous and crystalline salts form of the compound provides advantageous production, handling, storage and therapeutic properties.

Thus, the present invention also relates to amorphous and crystalline salts of (R)-9-(2,5-difluorophenethyl)-4-ethyl-2-methyl-1-oxa-4,9-diazaspiro[5.5]undecan-3-one, to their use and to several processes for their preparation.

For example, it is surprisingly found and demonstrated that some of the amorphous and crystalline salts of (R)-9-(2,5-difluorophenethyl)-4-ethyl-2-methyl-1-oxa-4,9-diazaspiro[5.5]undecan-3-one and specifically the hydrogen halides salts and simple carboxylic diacid salts provides advantageous production, handling, storage and/or therapeutic properties.

Further, among the acids suitable for obtaining amorphous and crystalline salts, it has been surprisingly found that the strong inorganic monoacids and the organic diacids provided good results in terms of easiness of preparation, physical stability, scaling-up, solubility, etc. This is particularly true for hydrochloride, hydrobromide, phosphate, sulfate, nitrate, fumarate, maleate, succinate, oxalate and malonate. These forms provide a clear improvement over the free base, which is an oily product and thus not suitable for development. In addition they may improve some specific properties, such as thermodynamic solubility For clarity reasons, the amorphous and crystalline salts of the present invention are sometimes referring to as the corresponding acid or as the amorphous and crystalline salt as such. There are two different ways of describing the same product. For example, malonate amorphous or crystalline salts are also referring to amorphous or crystalline salts of malonic acid, succinate amorphous or crystalline salts to amorphous or crystalline salts of succinic acid, oxalate amorphous or crystalline salts to amorphous or crystalline salts of oxalic acid, respectively etc.

In first aspect, the present invention relates to (R)-9-(2,5-difluorophenethyl)-4-ethyl-2-methyl-1-oxa-4,9-diazaspiro[5.5]undecan-3-one crystalline salts.

In another aspect, the present invention relates to (R)-9-(2,5-difluorophenethyl)-4-ethyl-2-methyl-1-oxa-4,9-diazaspiro[5.5]undecan-3-one amorphous salts.

In a preferred embodiment, the amorphous or crystalline salt of (R)-9-(2,5-difluorophenethyl)-4-ethyl-2-methyl-1-oxa-4,9-diazaspiro[5.5]undecan-3-one is selected from inorganic acids.

In a preferred embodiment, the amorphous or crystalline salt of (R)-9-(2,5-difluorophenethyl)-4-ethyl-2-methyl-1-oxa-4,9-diazaspiro[5.5]undecan-3-one is selected from organic acids.

In a preferred embodiment, the amorphous or crystalline salt of (R)-9-(2,5-difluorophenethyl)-4-ethyl-2-methyl-1-oxa-4,9-diazaspiro[5.5]undecan-3-one is selected from the group consisting of sulfonic acids.

In a preferred embodiment, the amorphous or crystalline salt of (R)-9-(2,5-difluorophenethyl)-4-ethyl-2-methyl-1-oxa-4,9-diazaspiro[5.5]undecan-3-one is selected from the group consisting of di-acids.

In a preferred embodiment, the amorphous or crystalline salt of (R)-9-(2,5-difluorophenethyl)-4-ethyl-2-methyl-1-oxa-4,9-diazaspiro[5.5]undecan-3-one is selected from the group consisting of mono-acids.

In a preferred embodiment, the amorphous or crystalline salt of (R)-9-(2,5-difluorophenethyl)-4-ethyl-2-methyl-1-oxa-4,9-diazaspiro[5.5]undecan-3-one is selected from hydrochloride, fumarate, hydrobromide, maleate, phosphate, sulfate, succinate, oxalate, malonate, mesylate, esylate, besylate, nitrate and (S)-(+)-mandelate.

In a preferred embodiment, the amorphous or crystalline salt of (R)-9-(2,5-difluorophenethyl)-4-ethyl-2-methyl-1-oxa-4,9-diazaspiro[5.5]undecan-3-one is selected from hydrochloride, fumarate, hydrobromide, maleate, phosphate, sulfate, succinate, oxalate, malonate, mesylate, esylate, besylate and nitrate.

In a preferred embodiment, the amorphous or crystalline salt of (R)-9-(2,5-difluorophenethyl)-4-ethyl-2-methyl-1-oxa-4,9-diazaspiro[5.5]undecan-3-one is selected from hydrochloride, hydrobromide, phosphate, sulfate and nitrate.

In a preferred embodiment, the amorphous or crystalline salt of (R)-9-(2,5-difluorophenethyl)-4-ethyl-2-methyl-1-oxa-4,9-diazaspiro[5.5]undecan-3-one is selected from fumarate, maleate, succinate, oxalate, malonate, mesylate, esylate, besylate, and (S)-(+)-mandelate.

In a preferred embodiment, the amorphous or crystalline salt of (R)-9-(2,5-difluorophenethyl)-4-ethyl-2-methyl-1-oxa-4,9-diazaspiro[5.5]undecan-3-one is selected from mesylate, esylate and besylate.

In a preferred embodiment, the amorphous or crystalline salt of (R)-9-(2,5-difluorophenethyl)-4-ethyl-2-methyl-1-oxa-4,9-diazaspiro[5.5]undecan-3-one is selected from fumarate, maleate, succinate, oxalate and malonate.

In a preferred embodiment, the amorphous or crystalline salt of (R)-9-(2,5-difluorophenethyl)-4-ethyl-2-methyl-1-oxa-4,9-diazaspiro[5.5]undecan-3-one is selected from fumarate, maleate, succinate, oxalate and malonate.

In a preferred embodiment, the amorphous or crystalline salt of (R)-9-(2,5-difluorophenethyl)-4-ethyl-2-methyl-1-oxa-4,9-diazaspiro[5.5]undecan-3-one is selected from mesylate, esylate, besylate and (S)-(+)-mandelate.

In a preferred embodiment, the amorphous or crystalline salt of (R)-9-(2,5-difluorophenethyl)-4-ethyl-2-methyl-1-oxa-4,9-diazaspiro[5.5]undecan-3-one is selected from mesylate, esylate and besylate.

In a preferred embodiment, the amorphous or crystalline salt of (R)-9-(2,5-difluorophenethyl)-4-ethyl-2-methyl-1-oxa-4,9-diazaspiro[5.5]undecan-3-one is (S)-(+)-mandelate.

In a preferred embodiment, the amorphous or crystalline salt of (R)-9-(2,5-difluorophenethyl)-4-ethyl-2-methyl-1-oxa-4,9-diazaspiro[5.5]undecan-3-one is selected from hydrochloride, fumarate, hydrobromide, maleate, phosphate, sulfate, succinate, oxalate, malonate, mesylate, esylate, besylate and nitrate.

In a preferred embodiment, the amorphous or crystalline salt of (R)-9-(2,5-difluorophenethyl)-4-ethyl-2-methyl-1-oxa-4,9-diazaspiro[5.5]undecan-3-one is selected from hydrochloride, fumarate, hydrobromide, maleate, phosphate, sulfate, succinate, oxalate, malonate, mesylate, esylate, besylate, nitrate, and (S)-(+)-mandelate.

In a preferred embodiment, the amorphous or crystalline salt of (R)-9-(2,5-difluorophenethyl)-4-ethyl-2-methyl-1-oxa-4,9-diazaspiro[5.5]undecan-3-one is selected from hydrochloride, fumarate, hydrobromide, maleate, phosphate, sulfate, succinate, oxalate, malonate, mesylate, esylate, besylate, nitrate and (S)-(+)-mandelate.

In a preferred embodiment, the amorphous or crystalline salt of (R)-9-(2,5-difluorophenethyl)-4-ethyl-2-methyl-1-oxa-4,9-diazaspiro[5.5]undecan-3-one is selected from hydrochloride, fumarate, hydrobromide, maleate, phosphate, sulfate, succinate, oxalate, malonate, mesylate, esylate, besylate and nitrate.

In a preferred embodiment, the amorphous or crystalline salt of (R)-9-(2,5-difluorophenethyl)-4-ethyl-2-methyl-1-oxa-4,9-diazaspiro[5.5]undecan-3-one is mesylate.

In a preferred embodiment, the amorphous or crystalline salt of (R)-9-(2,5-difluorophenethyl)-4-ethyl-2-methyl-1-oxa-4,9-diazaspiro[5.5]undecan-3-one is not the hydrochloride salt.

In a preferred embodiment, the amorphous or crystalline salt of (R)-9-(2,5-difluorophenethyl)-4-ethyl-2-methyl-1-oxa-4,9-diazaspiro[5.5]undecan-3-one is the hydrochloride salt.

In a preferred embodiment, the amorphous or crystalline salt of (R)-9-(2,5-difluorophenethyl)-4-ethyl-2-methyl-1-oxa-4,9-diazaspiro[5.5]undecan-3-one is the hydrobromide salt.

In a preferred embodiment, the amorphous or crystalline salt of (R)-9-(2,5-difluorophenethyl)-4-ethyl-2-methyl-1-oxa-4,9-diazaspiro[5.5]undecan-3-one is the fumarate salt.

In a preferred embodiment, the amorphous or crystalline salt of (R)-9-(2,5-difluorophenethyl)-4-ethyl-2-methyl-1-oxa-4,9-diazaspiro[5.5]undecan-3-one is the maleate salt.

In a preferred embodiment, the amorphous or crystalline salt of (R)-9-(2,5-difluorophenethyl)-4-ethyl-2-methyl-1-oxa-4,9-diazaspiro[5.5]undecan-3-one is the besylate salt.

In a preferred embodiment, the amorphous or crystalline salt of (R)-9-(2,5-difluorophenethyl)-4-ethyl-2-methyl-1-oxa-4,9-diazaspiro[5.5]undecan-3-one is the phosphate salt.

In a preferred embodiment, the amorphous or crystalline salt of (R)-9-(2,5-difluorophenethyl)-4-ethyl-2-methyl-1-oxa-4,9-diazaspiro[5.5]undecan-3-one is the sulfate salt.

In a preferred embodiment, the amorphous or crystalline salt of (R)-9-(2,5-difluorophenethyl)-4-ethyl-2-methyl-1-oxa-4,9-diazaspiro[5.5]undecan-3-one is the succinate salt.

In a preferred embodiment, the amorphous or crystalline salt of (R)-9-(2,5-difluorophenethyl)-4-ethyl-2-methyl-1-oxa-4,9-diazaspiro[5.5]undecan-3-one is the oxalate salt.

In a preferred embodiment, the amorphous or crystalline salt of (R)-9-(2,5-difluorophenethyl)-4-ethyl-2-methyl-1-oxa-4,9-diazaspiro[5.5]undecan-3-one is the malonate salt.

In a preferred embodiment, the amorphous or crystalline salt of (R)-9-(2,5-difluorophenethyl)-4-ethyl-2-methyl-1-oxa-4,9-diazaspiro[5.5]undecan-3-one is the esylate salt.

In a preferred embodiment, the amorphous or crystalline salt of (R)-9-(2,5-difluorophenethyl)-4-ethyl-2-methyl-1-oxa-4,9-diazaspiro[5.5]undecan-3-one is the nitrate salt.

In a preferred embodiment, the amorphous or crystalline salt of (R)-9-(2,5-difluorophenethyl)-4-ethyl-2-methyl-1-oxa-4,9-diazaspiro[5.5]undecan-3-one is the (S)-(+)-mandelate salt.

As noted previously, it has been reported that (R)-9-(2,5-difluorophenethyl)-4-ethyl-2-methyl-1-oxa-4,9-diazaspiro[5.5]undecan-3-one is selective sigma-1 ($\sigma_1$) receptor antagonist and/or μ-opioid receptor agonist, displaying strong analgesic activity in the treatment and prevention of pain (see WO 2015185209).

The present invention therefore further provides medicaments or pharmaceutical compositions comprising a (R)-9-(2,5-difluorophenethyl)-4-ethyl-2-methyl-1-oxa-4,9-diazaspiro[5.5]undecan-3-one amorphous or crystalline salt according to the present invention, together with at least a pharmaceutically acceptable carrier, adjuvant, or vehicle, for administration to a patient.

In one embodiment of the invention the (R)-9-(2,5-difluorophenethyl)-4-ethyl-2-methyl-1-oxa-4,9-diazaspiro[5.5]undecan-3-one amorphous or crystalline salt is used in therapeutically effective amounts.

Particularly, the (R)-9-(2,5-difluorophenethyl)-4-ethyl-2-methyl-1-oxa-4,9-diazaspiro[5.5]undecan-3-one amorphous or crystalline salts according to the present invention, are useful for the treatment and/or prophylaxis of a sigma receptor and/or μ-opioid receptor mediated disease or condition.

In a preferred embodiment, all the amorphous or crystalline salts according to the present invention are useful for the treatment and/or prophylaxis of a sigma receptor and/or μ-opioid receptor mediated disease or condition, preferably all the amorphous or crystalline salts according to the present invention are useful for the treatment and/or prophylaxis of a sigma receptor and μ-opioid receptor mediated disease or condition.

It has now been found that the (R)-9-(2,5-difluorophenethyl)-4-ethyl-2-methyl-1-oxa-4,9-diazaspiro[5.5]undecan-3-one amorphous or crystalline salts according to the present invention are particularly suitable for use as a medicament.

In a preferred embodiment, the invention relates to (R)-9-(2,5-difluorophenethyl)-4-ethyl-2-methyl-1-oxa-4,9-diazaspiro[5.5]undecan-3-one amorphous or crystalline salts for use as a medicament.

In a preferred embodiment, the present invention relates to the use of (R)-9-(2,5-difluorophenethyl)-4-ethyl-2-methyl-1-oxa-4,9-diazaspiro[5.5]undecan-3-one amorphous or crystalline salts for the manufacture of a medicament.

In a preferred embodiment, the present invention relates to (R)-9-(2,5-difluorophenethyl)-4-ethyl-2-methyl-1-oxa-4,9-diazaspiro[5.5]undecan-3-one amorphous or crystalline salts is for use in the manufacture of a medicament.

In a preferred embodiment, the present invention relates to (R)-9-(2,5-difluorophenethyl)-4-ethyl-2-methyl-1-oxa-4,9-diazaspiro[5.5]undecan-3-one amorphous or crystalline salts for use in the treatment and/or prophylaxis of pain.

In a preferred embodiment, the present invention relates to (R)-9-(2,5-difluorophenethyl)-4-ethyl-2-methyl-1-oxa-4,9-diazaspiro[5.5]undecan-3-one amorphous or crystalline salts for use in the treatment and/or prophylaxis of medium to severe pain, visceral pain, chronic pain, cancer pain, migraine, inflammatory pain, acute pain or neuropathic pain, allodynia or hyperalgesia, also preferably including mechanical allodynia or thermal hyperalgesia.

In a preferred embodiment, the present invention relates to a method for the treatment and/or prophylaxis of pain, said method comprises administering to a patient in need a (R)-9-(2,5-difluorophenethyl)-4-ethyl-2-methyl-1-oxa-4,9-diazaspiro[5.5]undecan-3-one amorphous or crystalline salt.

In a preferred embodiment, the present invention relates to a method for the treatment and/or prophylaxis of medium to severe pain, visceral pain, chronic pain, cancer pain, migraine, inflammatory pain, acute pain or neuropathic pain, allodynia or hyperalgesia, also preferably including mechanical allodynia or thermal hyperalgesia, said method comprises administering to a patient in need a (R)-9-(2,5-difluorophenethyl)-4-ethyl-2-methyl-1-oxa-4,9-diazaspiro[5.5]undecan-3-one amorphous or crystalline salt.

In a preferred embodiment, the present invention relates to the use of (R)-9-(2,5-difluorophenethyl)-4-ethyl-2-methyl-1-oxa-4,9-diazaspiro[5.5]undecan-3-one amorphous or crystalline salts for the manufacture of a medicament for the treatment and/or prophylaxis of pain.

In a preferred embodiment, the present invention relates to the use of (R)-9-(2,5-difluorophenethyl)-4-ethyl-2-methyl-1-oxa-4,9-diazaspiro[5.5]undecan-3-one amorphous or crystalline salts for the manufacture of a medicament for the treatment and/or prophylaxis of medium to severe pain, visceral pain, chronic pain, cancer pain, migraine, inflammatory pain, acute pain or neuropathic pain, allodynia or hyperalgesia, also preferably including mechanical allodynia or thermal hyperalgesia.

In a preferred embodiment, the present invention relates to (R)-9-(2,5-difluorophenethyl)-4-ethyl-2-methyl-1-oxa-4,9-diazaspiro[5.5]undecan-3-one amorphous or crystalline salts for use in the manufacture of a medicament for the treatment and/or prophylaxis of pain.

In a preferred embodiment, the present invention relates to (R)-9-(2,5-difluorophenethyl)-4-ethyl-2-methyl-1-oxa-4,9-diazaspiro[5.5]undecan-3-one amorphous or crystalline salts for use in the manufacture of a medicament for the treatment and/or prophylaxis of medium to severe pain, visceral pain, chronic pain, cancer pain, migraine, inflammatory pain, acute pain or neuropathic pain, allodynia or hyperalgesia, also preferably including mechanical allodynia or thermal hyperalgesia.

In a particular aspect, the present invention relates to polymorphs of (R)-9-(2,5-difluorophenethyl)-4-ethyl-2-methyl-1-oxa-4,9-diazaspiro[5.5]undecan-3-one salts, exhibiting advantages compared with other forms such as improved physicochemical characteristics
Higher solubility
Faster dissolution rate
Lower hygroscopicity In an embodiment, the invention refers to the (R)-9-(2,5-difluorophenethyl)-4-ethyl-2-methyl-1-oxa-4,9-diazaspiro[5.5]undecan-3-one salt in crystalline form selected from the group consisting of the polymorph P1, P2 or P3 of the hydrochloride salt, the polymorph P1 of the fumarate salt, the polymorph P1 of the hydrobromide salt, the polymorph P1, P2 or P3 of the maleate salt, the polymorph P1 of the phosphate salt, the polymorph P1 of the sulfate salt, the polymorph P1 of the succinate salt, the polymorph P1, P2 or P3 of the oxalate salt, the polymorph P1 of the malonate salt, the polymorph P1 of the mesylate salt, the polymorph P1 of the esylate salt, the polymorph P1 of the besylate salt, the polymorph P1 of the nitrate salt and the polymorph P1 of the (S)-(+)-mandelate salt.

In an embodiment, the invention refers to the polymorph P1 of the (R)-9-(2,5-difluorophenethyl)-4-ethyl-2-methyl-1-oxa-4,9-diazaspiro[5.5]undecan-3-one hydrochloric salt.

In an embodiment, the invention refers to the polymorph P1 of the (R)-9-(2,5-difluorophenethyl)-4-ethyl-2-methyl-1-oxa-4,9-diazaspiro[5.5]undecan-3-one hydrochloric salt, having the following XRPD pattern (FIG. 2):

| Pos. [°2θ] | Rel. Int. [%] |
|---|---|
| 5.5 | 71 |
| 9.8 | 2 |
| 11 | 100 |
| 13.7 | 3 |
| 15.4 | 10 |
| 16.5 | 50 |
| 17.4 | 3 |
| 18.5 | 34 |
| 19.3 | 2 |
| 19.8 | 5 |
| 22.1 | 8 |
| 22.6 | 6 |
| 23.1 | 7 |
| 23.4 | 11 |
| 23.6 | 21 |
| 27.1 | 2 |
| 29 | 6 |
| 32.4 | 2 |
| 33.6 | 1 |
| 34.5 | 2 |
| 39.2 | 6 |

In an embodiment, the invention refers to the polymorph P1 of the (R)-9-(2,5-difluorophenethyl)-4-ethyl-2-methyl-1-oxa-4,9-diazaspiro[5.5]undecan-3-one hydrochloric salt, having the following XRPD pattern:

| Pos. [°2θ] | Rel. Int. [%] |
|---|---|
| 5.5 | 71 |
| 11 | 100 |
| 15.4 | 10 |
| 16.5 | 50 |
| 18.5 | 34 |
| 23.4 | 11 |
| 23.6 | 21 |

In an embodiment, the invention refers to the polymorph P1 of the (R)-9-(2,5-difluorophenethyl)-4-ethyl-2-methyl-1-oxa-4,9-diazaspiro[5.5]undecan-3-one hydrochloric salt, having the following XRPD pattern:

| Pos. [°2θ] | Rel. Int. [%] |
|---|---|
| 5.5 | 71 |
| 11 | 100 |
| 16.5 | 50 |
| 18.5 | 34 |

In an embodiment, the invention refers to the polymorph P1 of the (R)-9-(2,5-difluorophenethyl)-4-ethyl-2-methyl-1-oxa-4,9-diazaspiro[5.5]undecan-3-one hydrochloric salt, having the following $^1$H-NMR (FIG. 3):

RMN-$^1$H (CDCl$_3$, 400 MHz, δ): 7.09-6.93 (m, 3H, ArH); 4.11 (q, 1H, J=6.8 Hz, CH); 3.54-3.43 (m, 4H, CH$_2$); 3.39-3.31 (m, 3H, CH$_2$); 3.20-3.11 (m, 4H, CH$_2$); 2.98-2.89 (m, 1H, CH$_2$); 2.61-2.51 (m, 1H, CH$_2$); 2.48-2.40 (m, 1H, CH$_2$); 2.28-2.24 (m, 1H, CH$_2$); 1.86-1.82 (m, 1H, CH$_2$); 1.44 (d, J=6.8 Hz, 3H, CH$_3$); 1.13 (t, J=7.2 Hz, 3H, CH$_3$).

In an embodiment, the invention refers to the polymorph P1 of the (R)-9-(2,5-difluorophenethyl)-4-ethyl-2-methyl-1-oxa-4,9-diazaspiro[5.5]undecan-3-one hydrochloric salt, having an endothermic peak of 250° C. (FIG. 4).

In a further embodiment, the invention refers to the polymorph P2 of the (R)-9-(2,5-difluorophenethyl)-4-ethyl-2-methyl-1-oxa-4,9-diazaspiro[5.5]undecan-3-one hydrochloric salt.

In a further embodiment, the invention refers to the polymorph P2 of the (R)-9-(2,5-difluorophenethyl)-4-ethyl-2-methyl-1-oxa-4,9-diazaspiro[5.5]undecan-3-one hydrochloric salt, having the following XRPD pattern (FIG. 5):

| Pos. [°2θ] | Rel. Int. [%] |
|---|---|
| 7.0 | 30 |
| 8.4 | 14 |
| 12.0 | 11 |
| 13.0 | 53 |
| 13.4 | 5 |
| 13.8 | 7 |
| 14.2 | 9 |
| 15.3 | 100 |
| 15.5 | 33 |
| 16.8 | 11 |
| 17.3 | 4 |
| 18.6 | 3 |
| 19.1 | 18 |
| 19.5 | 17 |
| 20.4 | 26 |
| 21.1 | 4 |
| 22.5 | 13 |
| 23.1 | 10 |
| 23.4 | 14 |
| 24.1 | 17 |
| 24.6 | 11 |
| 25.3 | 18 |
| 26.1 | 8 |

-continued

| Pos. [°2θ] | Rel. Int. [%] |
|---|---|
| 27.1 | 16 |
| 28.0 | 9 |
| 29.8 | 1 |
| 31.4 | 10 |
| 33.6 | 4 |
| 35.0 | 2 |
| 37.6 | 2 |

In a further embodiment, the invention refers to the polymorph P2 of the (R)-9-(2,5-difluorophenethyl)-4-ethyl-2-methyl-1-oxa-4,9-diazaspiro[5.5]undecan-3-one hydrochloric salt, having the following XRPD pattern:

| Pos. [°2θ] | Rel. Int. [%] |
|---|---|
| 7.0 | 30 |
| 8.4 | 14 |
| 12.0 | 11 |
| 13.0 | 53 |
| 15.3 | 100 |
| 15.5 | 33 |
| 16.8 | 11 |
| 19.1 | 18 |
| 19.5 | 17 |
| 23.4 | 14 |
| 24.1 | 17 |
| 24.6 | 11 |
| 20.4 | 26 |
| 22.5 | 13 |
| 23.1 | 10 |
| 25.3 | 18 |
| 27.1 | 16 |
| 31.4 | 10 |

In a further embodiment, the invention refers to the polymorph P2 of the (R)-9-(2,5-difluorophenethyl)-4-ethyl-2-methyl-1-oxa-4,9-diazaspiro[5.5]undecan-3-one hydrochloric salt, having the following XRPD pattern:

| Pos. [°2θ] | Rel. Int. [%] |
|---|---|
| 7.0 | 30 |
| 13.0 | 53 |
| 15.3 | 100 |
| 15.5 | 33 |

In a further embodiment, the invention refers to the polymorph P2 of the (R)-9-(2,5-difluorophenethyl)-4-ethyl-2-methyl-1-oxa-4,9-diazaspiro[5.5]undecan-3-one hydrochloric salt, having the following $^1$H-NMR (FIG. 6):

RMN-$^1$H (CDCl$_3$, 400 MHz, δ): 7.09-6.92 (m, 3H, ArH); 4.10 (q, 1H, J=6.8 Hz, CH); 3.54-3.43 (m, 4H, CH$_2$); 3.39-3.30 (m, 3H, CH$_2$); 3.20-3.15 (m, 4H, CH$_2$); 2.97-2.89 (m, 1H, CH$_2$); 2.60-2.52 (m, 1H, CH$_2$); 2.47-2.39 (m, 1H, CH$_2$); 2.28-2.24 (m, 1H, CH$_2$); 1.86-1.82 (m, 1H, CH$_2$); 1.44 (d, J=6.8 Hz, 3H, CH$_3$); 1.12 (t, J=7.2 Hz, 3H, CH$_3$).

In a further embodiment, the invention refers to the polymorph P2 of the (R)-9-(2,5-difluorophenethyl)-4-ethyl-2-methyl-1-oxa-4,9-diazaspiro[5.5]undecan-3-one hydrochloric salt having an endothermic peak at 249° C. (FIG. 7)

In a further embodiment, the invention refers to the polymorph P3 of the (R)-9-(2,5-difluorophenethyl)-4-ethyl-2-methyl-1-oxa-4,9-diazaspiro[5.5]undecan-3-one hydrochloric salt.

In a further embodiment, the invention refers to the polymorph P3 of the (R)-9-(2,5-difluorophenethyl)-4-ethyl-2-methyl-1-oxa-4,9-diazaspiro[5.5]undecan-3-one hydrochloric salt, having the following XRPD pattern (FIG. 8):

| Pos. [°2θ] | Rel. Int. [%] |
|---|---|
| 5.6 | 100 |
| 10.2 | 1 |
| 11.4 | 74 |
| 15.2 | 18 |
| 15.8 | 28 |
| 16.5 | 8 |
| 17.1 | 48 |
| 17.8 | 5 |
| 18.5 | 6 |
| 20.7 | 28 |
| 22.6 | 3 |
| 25.4 | 5 |

In a further embodiment, the invention refers to the polymorph P3 of the (R)-9-(2,5-difluorophenethyl)-4-ethyl-2-methyl-1-oxa-4,9-diazaspiro[5.5]undecan-3-one hydrochloric salt, having the following XRPD pattern:

| Pos. [°2θ] | Rel. Int. [%] |
|---|---|
| 5.6 | 100 |
| 11.4 | 74 |
| 15.2 | 18 |
| 15.8 | 28 |
| 17.1 | 48 |
| 20.7 | 28 |

In a further embodiment, the invention refers to the polymorph P3 of the (R)-9-(2,5-difluorophenethyl)-4-ethyl-2-methyl-1-oxa-4,9-diazaspiro[5.5]undecan-3-one hydrochloric salt, having the following XRPD pattern:

| Pos. [°2θ] | Rel. Int. [%] |
|---|---|
| 5.6 | 100 |
| 11.4 | 74 |
| 17.1 | 48 |

In an embodiment, the invention refers to the polymorph P1 of the (R)-9-(2,5-difluorophenethyl)-4-ethyl-2-methyl-1-oxa-4,9-diazaspiro[5.5]undecan-3-one fumaric salt.

In an embodiment, the invention refers to the polymorph P1 of the (R)-9-(2,5-difluorophenethyl)-4-ethyl-2-methyl-1-oxa-4,9-diazaspiro[5.5]undecan-3-one fumaric salt, having the following XRPD pattern (FIG. 9):

| Pos. [°2θ] | Rel. Int. [%] |
|---|---|
| 6.5 | 24 |
| 6.8 | 26 |
| 8.9 | 73 |
| 11.5 | 16 |
| 12.0 | 65 |
| 13.7 | 9 |
| 14.4 | 9 |
| 14.9 | 50 |
| 15.6 | 13 |
| 16.1 | 10 |
| 17.1 | 100 |
| 17.5 | 59 |
| 17.8 | 19 |
| 18.5 | 42 |
| 18.6 | 33 |
| 19.3 | 13 |
| 19.7 | 12 |

-continued

| Pos. [°2θ] | Rel. Int. [%] |
|---|---|
| 20.6 | 25 |
| 21.4 | 6 |
| 22.5 | 18 |
| 22.8 | 17 |
| 23.2 | 14 |
| 23.5 | 15 |
| 24.6 | 65 |
| 25.4 | 15 |
| 26.2 | 26 |
| 27.1 | 6 |
| 27.6 | 3 |
| 28.7 | 13 |
| 29.4 | 5 |
| 30.2 | 3 |
| 32.0 | 6 |
| 33.9 | 7 |
| 35.6 | 4 |
| 38.0 | 4 |
| 38.6 | 4 |

In an embodiment, the invention refers to the polymorph P1 of the (R)-9-(2,5-difluorophenethyl)-4-ethyl-2-methyl-1-oxa-4,9-diazaspiro[5.5]undecan-3-one fumaric salt, having the following XRPD pattern:

| Pos. [°2θ] | Rel. Int. [%] |
|---|---|
| 6.5 | 24 |
| 6.8 | 26 |
| 8.9 | 73 |
| 11.5 | 16 |
| 12.0 | 65 |
| 14.9 | 50 |
| 15.6 | 13 |
| 16.1 | 10 |
| 17.1 | 100 |
| 17.5 | 59 |
| 17.8 | 19 |
| 18.5 | 42 |
| 18.6 | 33 |
| 19.3 | 13 |
| 19.7 | 12 |
| 20.6 | 25 |
| 22.5 | 18 |
| 22.8 | 17 |
| 23.2 | 14 |
| 23.5 | 15 |
| 24.6 | 65 |
| 25.4 | 15 |
| 26.2 | 26 |
| 28.7 | 13 |

In an embodiment, the invention refers to the polymorph P1 of the (R)-9-(2,5-difluorophenethyl)-4-ethyl-2-methyl-1-oxa-4,9-diazaspiro[5.5]undecan-3-one fumaric salt, having the following XRPD pattern:

| Pos. [°2θ] | Rel. Int. [%] |
|---|---|
| 6.5 | 24 |
| 6.8 | 26 |
| 8.9 | 73 |
| 12.0 | 65 |
| 14.9 | 50 |
| 17.1 | 100 |
| 17.5 | 59 |
| 18.5 | 42 |
| 18.6 | 33 |
| 20.6 | 25 |
| 24.6 | 65 |
| 26.2 | 26 |

In an embodiment, the invention refers to the polymorph P1 of the (R)-9-(2,5-difluorophenethyl)-4-ethyl-2-methyl-1-oxa-4,9-diazaspiro[5.5]undecan-3-one fumaric salt, having the following XRPD pattern:

| Pos. [°2θ] | Rel. Int. [%] |
|---|---|
| 8.9 | 73 |
| 12.0 | 65 |
| 14.9 | 50 |
| 17.1 | 100 |
| 17.5 | 59 |
| 18.5 | 42 |
| 18.6 | 33 |
| 24.6 | 65 |

In an embodiment, the invention refers to the polymorph P1 of the (R)-9-(2,5-difluorophenethyl)-4-ethyl-2-methyl-1-oxa-4,9-diazaspiro[5.5]undecan-3-one fumaric salt, having the following XRPD pattern:

| Pos. [°2θ] | Rel. Int. [%] |
|---|---|
| 8.9 | 73 |
| 12.0 | 65 |
| 14.9 | 50 |
| 17.1 | 100 |
| 17.5 | 59 |
| 18.5 | 42 |
| 24.6 | 65 |

In an embodiment, the invention refers to the polymorph P1 of the (R)-9-(2,5-difluorophenethyl)-4-ethyl-2-methyl-1-oxa-4,9-diazaspiro[5.5]undecan-3-one fumaric salt, having the following XRPD pattern:

| Pos. [°2θ] | Rel. Int. [%] |
|---|---|
| 8.9 | 73 |
| 12.0 | 65 |
| 14.9 | 50 |
| 17.1 | 100 |
| 17.5 | 59 |
| 24.6 | 65 |

In an embodiment, the invention refers to the polymorph P1 of the (R)-9-(2,5-difluorophenethyl)-4-ethyl-2-methyl-1-oxa-4,9-diazaspiro[5.5]undecan-3-one fumaric salt, having the following XRPD pattern:

| Pos. [°2θ] | Rel. Int. [%] |
|---|---|
| 8.9 | 73 |
| 12.0 | 65 |
| 17.1 | 100 |
| 24.6 | 65 |

In an embodiment, the invention refers to the polymorph P1 of the (R)-9-(2,5-difluorophenethyl)-4-ethyl-2-methyl-1-oxa-4,9-diazaspiro[5.5]undecan-3-one fumaric salt, having the following $^1$H-NMR (FIG. 10):

RMN-$^1$H (DMSO, 400 MHz, δ): 7.24-7.15 (m, 2H, ArH); 7.10-7.04 (m, 1H, ArH); 6.60 (s, 2H, CH=); 4.09 (q, 1H, J=6.8 Hz, CH); 3.42-3.28 (m, 2H, CH$_2$); 3.23-3.14 (m, 2H, CH$_2$); 2.80-2.76 (m, 2H, CH$_2$); 2.69-2.60 (m, 4H, CH$_2$); 2.48-2.29 (m, 2H, CH$_2$); 1.92-1.87 (m, 1H, CH$_2$); 1.66-1.51 (m, 3H, CH$_2$); 1.25 (d, J=7.2 Hz, 3H, CH$_3$); 1.01 (t, J=6.8 Hz, 3H, CH$_3$).

In an embodiment, the invention refers to the polymorph P1 of the (R)-9-(2,5-difluorophenethyl)-4-ethyl-2-methyl-1-oxa-4,9-diazaspiro[5.5]undecan-3-one fumaric salt having an endothermic peak at 197° C. (FIG. 11)

In an embodiment, the invention refers to the polymorph P1 of the (R)-9-(2,5-difluorophenethyl)-4-ethyl-2-methyl-1-oxa-4,9-diazaspiro[5.5]undecan-3-one hydrobromic salt.

In an embodiment, the invention refers to the polymorph P1 of the (R)-9-(2,5-difluorophenethyl)-4-ethyl-2-methyl-1-oxa-4,9-diazaspiro[5.5]undecan-3-one hydrobromic salt, having the following XRPD pattern (FIG. 12):

| Pos. [°2θ] | Rel. Int. [%] |
| --- | --- |
| 5.5 | 100 |
| 9.7 | 9 |
| 13.7 | 22 |
| 15.0 | 16 |
| 16.1 | 19 |
| 16.6 | 23 |
| 17.1 | 13 |
| 17.8 | 11 |
| 18.5 | 30 |
| 19.0 | 15 |
| 19.6 | 23 |
| 20.2 | 10 |
| 20.7 | 3 |
| 22.1 | 34 |
| 22.7 | 42 |
| 23.3 | 25 |
| 23.7 | 24 |
| 25.0 | 9 |
| 26.8 | 9 |
| 28.1 | 7 |
| 28.7 | 3 |
| 29.2 | 15 |
| 32.6 | 5 |
| 33.2 | 8 |
| 34.7 | 5 |
| 36.3 | 3 |

In an embodiment, the invention refers to the polymorph P1 of the (R)-9-(2,5-difluorophenethyl)-4-ethyl-2-methyl-1-oxa-4,9-diazaspiro[5.5]undecan-3-one hydrobromic salt, having the following XRPD pattern:

| Pos. [°2θ] | Rel. Int. [%] |
| --- | --- |
| 5.5 | 100 |
| 13.7 | 22 |
| 15.0 | 16 |
| 16.1 | 19 |
| 16.6 | 23 |
| 17.1 | 13 |
| 17.8 | 11 |
| 18.5 | 30 |
| 19.0 | 15 |
| 19.6 | 23 |
| 20.2 | 10 |
| 22.1 | 34 |
| 22.7 | 42 |
| 23.3 | 25 |
| 23.7 | 24 |
| 29.2 | 15 |

In an embodiment, the invention refers to the polymorph P1 of the (R)-9-(2,5-difluorophenethyl)-4-ethyl-2-methyl-1-oxa-4,9-diazaspiro[5.5]undecan-3-one hydrobromic salt having the following XRPD pattern:

| Pos. [°2θ] | Rel. Int. [%] |
| --- | --- |
| 5.5 | 100 |
| 13.7 | 22 |
| 16.6 | 23 |
| 18.5 | 30 |
| 19.6 | 23 |
| 22.1 | 34 |
| 22.7 | 42 |
| 23.3 | 25 |
| 23.7 | 24 |

In an embodiment, the invention refers to the polymorph P1 of the (R)-9-(2,5-difluorophenethyl)-4-ethyl-2-methyl-1-oxa-4,9-diazaspiro[5.5]undecan-3-one hydrobromic salt having the following XRPD pattern:

| Pos. [°2θ] | Rel. Int. [%] |
| --- | --- |
| 5.5 | 100 |
| 18.5 | 30 |
| 22.1 | 34 |
| 22.7 | 42 |

In an embodiment, the invention refers to the polymorph P1 of the (R)-9-(2,5-difluorophenethyl)-4-ethyl-2-methyl-1-oxa-4,9-diazaspiro[5.5]undecan-3-one hydrobromic salt, having the following $^1$H-NMR (FIG. 13):

RMN-$^1$H (CD$_3$OD, 400 MHz, δ): 7.19-7.14 (m, 2H, ArH); 7.11-7.05 (m, 1H, ArH); 4.23 (q, 1H, J=6.8 Hz, CH); 3.56-3.33 (m, 8H, CH$_2$); 3.28-3.11 (m, 4H, CH$_2$); 2.45-2.35 (m, 1H, CH$_2$); 2.06-1.75 (m, 1H, CH$_2$); 1.93-1.84 (m, 2H, CH$_2$); 1.41 (d, J=7.2 Hz, 3H, CH$_3$); 1.15 (t, J=6.8 Hz, 3H, CH$_3$).

In an embodiment, the invention refers to the polymorph P1 of the (R)-9-(2,5-difluorophenethyl)-4-ethyl-2-methyl-1-oxa-4,9-diazaspiro[5.5]undecan-3-one hydrobromic salt, having an endothermic peak at 245° C. (FIG. 14).

In an embodiment, the invention refers to the polymorph P1 of the (R)-9-(2,5-difluorophenethyl)-4-ethyl-2-methyl-1-oxa-4,9-diazaspiro[5.5]undecan-3-one maleic salt.

In an embodiment, the invention refers to the polymorph P1 of the (R)-9-(2,5-difluorophenethyl)-4-ethyl-2-methyl-1-oxa-4,9-diazaspiro[5.5]undecan-3-one maleic salt, having the following XRPD pattern (FIG. 15):

| Pos. [°2θ] | Rel. Int. [%] |
| --- | --- |
| 6.5 | 15 |
| 8.8 | 95 |
| 11.4 | 20 |
| 11.7 | 37 |
| 12.1 | 31 |
| 13.4 | 20 |

-continued

| Pos. [°2θ] | Rel. Int. [%] |
|---|---|
| 14.4 | 44 |
| 15.6 | 7 |
| 16.1 | 13 |
| 17.1 | 100 |
| 17.4 | 77 |
| 17.6 | 40 |
| 17.9 | 20 |
| 18.2 | 35 |
| 18.8 | 27 |
| 19.7 | 14 |
| 20.2 | 18 |
| 20.5 | 40 |
| 21.3 | 5 |
| 22.0 | 34 |
| 22.5 | 12 |
| 22.8 | 29 |
| 23.0 | 24 |
| 23.8 | 12 |
| 24.2 | 60 |
| 25.0 | 38 |
| 25.5 | 29 |
| 26.2 | 10 |
| 26.6 | 14 |
| 27.1 | 23 |
| 28.5 | 6 |
| 28.8 | 11 |
| 29.7 | 5 |
| 30.6 | 6 |
| 32.5 | 5 |
| 34.5 | 7 |
| 35.0 | 4 |
| 36.3 | 8 |

In an embodiment, the invention refers to the polymorph P1 of the (R)-9-(2,5-difluorophenethyl)-4-ethyl-2-methyl-1-oxa-4,9-diazaspiro[5.5]undecan-3-one maleic salt, having the following XRPD pattern:

| Pos. [°2θ] | Rel. Int. [%] |
|---|---|
| 6.5 | 15 |
| 8.8 | 95 |
| 11.4 | 20 |
| 11.7 | 37 |
| 12.1 | 31 |
| 13.4 | 20 |
| 14.4 | 44 |
| 16.1 | 13 |
| 17.1 | 100 |
| 17.4 | 77 |
| 17.6 | 40 |
| 17.9 | 20 |
| 18.2 | 35 |
| 18.8 | 27 |
| 19.7 | 14 |
| 22.0 | 34 |
| 20.2 | 18 |
| 20.5 | 40 |
| 22.5 | 12 |
| 22.8 | 29 |
| 23.0 | 24 |
| 23.8 | 12 |
| 24.2 | 60 |
| 25.0 | 38 |
| 25.5 | 29 |
| 26.2 | 10 |
| 26.6 | 14 |
| 27.1 | 23 |
| 28.8 | 11 |

In an embodiment, the invention refers to the polymorph P1 of the (R)-9-(2,5-difluorophenethyl)-4-ethyl-2-methyl-1-oxa-4,9-diazaspiro[5.5]undecan-3-one maleic salt, having the following XRPD pattern:

| Pos. [°2θ] | Rel. Int. [%] | Pos. [°2θ] | Rel. Int. [%] |
|---|---|---|---|
| 8.8 | 95 | 18.2 | 35 |
| 11.4 | 20 | 18.8 | 27 |
| 11.7 | 37 | 20.5 | 40 |
| 12.1 | 31 | 22.0 | 34 |
| 13.4 | 20 | 22.8 | 29 |
| 14.4 | 44 | 23.0 | 24 |
| 17.1 | 100 | 24.2 | 60 |
| 17.4 | 77 | 25.0 | 38 |
| 17.6 | 40 | 25.5 | 29 |
| 17.9 | 20 | 27.1 | 23 |

In an embodiment, the invention refers to the polymorph P1 of the (R)-9-(2,5-difluorophenethyl)-4-ethyl-2-methyl-1-oxa-4,9-diazaspiro[5.5]undecan-3-one maleic salt, having the following XRPD pattern:

| Pos. [°2θ] | Rel. Int. [%] | Pos. [°2θ] | Rel. Int. [%] |
|---|---|---|---|
| 8.8 | 95 | 17.6 | 40 |
| 11.7 | 37 | 18.2 | 35 |
| 12.1 | 31 | 20.5 | 40 |
| 14.4 | 44 | 22.0 | 34 |
| 17.1 | 100 | 24.2 | 60 |
| 17.4 | 77 | 25.0 | 38 |

In an embodiment, the invention refers to the polymorph P1 of the (R)-9-(2,5-difluorophenethyl)-4-ethyl-2-methyl-1-oxa-4,9-diazaspiro[5.5]undecan-3-one maleic salt, having the following XRPD pattern:

| Pos. [°2θ] | Rel. Int. [%] |
|---|---|
| 8.8 | 95 |
| 14.4 | 44 |
| 17.1 | 100 |
| 17.4 | 77 |
| 17.6 | 40 |
| 20.5 | 40 |
| 24.2 | 60 |

In an embodiment, the invention refers to the polymorph P1 of the (R)-9-(2,5-difluorophenethyl)-4-ethyl-2-methyl-1-oxa-4,9-diazaspiro[5.5]undecan-3-one maleic salt, having the following XRPD pattern:

| Pos. [°2θ] | Rel. Int. [%] |
|---|---|
| 8.8 | 95 |
| 17.1 | 100 |
| 17.4 | 77 |
| 24.2 | 60 |

In an embodiment, the invention refers to the polymorph P2 of the (R)-9-(2,5-difluorophenethyl)-4-ethyl-2-methyl-1-oxa-4,9-diazaspiro[5.5]undecan-3-one maleic salt.

In an embodiment, the invention refers to the polymorph P2 of the (R)-9-(2,5-difluorophenethyl)-4-ethyl-2-methyl-1-oxa-4,9-diazaspiro[5.5]undecan-3-one maleic salt, having the following XRPD pattern (FIG. 16):

| Pos. [°2θ] | Rel. Int. [%] | Pos. [°2θ] | Rel. Int. [%] |
|---|---|---|---|
| 3.3 | 4 | 19.4 | 9 |
| 8.9 | 32 | 20.6 | 12 |
| 11.8 | 39 | 22.1 | 6 |

-continued

| Pos. [°2θ] | Rel. Int. [%] | Pos. [°2θ] | Rel. Int. [%] |
|---|---|---|---|
| 13.3 | 6 | 22.5 | 6 |
| 13.6 | 4 | 22.9 | 13 |
| 14.3 | 5 | 23.6 | 20 |
| 15.4 | 34 | 24.7 | 4 |
| 16.2 | 33 | 25.1 | 2 |
| 17.4 | 18 | 26.9 | 12 |
| 17.8 | 100 | 27.3 | 7 |
| 18.0 | 54 | 31.4 | 5 |
| 18.5 | 10 | 31.9 | 5 |

In an embodiment, the invention refers to the polymorph P2 of the (R)-9-(2,5-difluorophenethyl)-4-ethyl-2-methyl-1-oxa-4,9-diazaspiro[5.5]undecan-3-one maleic salt, having the following XRPD pattern:

| Pos. [°2θ] | Rel. Int. [%] | Pos. [°2θ] | Rel. Int. [%] |
|---|---|---|---|
| 8.9 | 32 | 20.6 | 12 |
| 11.8 | 39 | 18.0 | 54 |
| 15.4 | 34 | 18.5 | 10 |
| 16.2 | 33 | 22.9 | 13 |
| 17.4 | 18 | 23.6 | 20 |
| 17.8 | 100 | 26.9 | 12 |

In an embodiment, the invention refers to the polymorph P2 of the (R)-9-(2,5-difluorophenethyl)-4-ethyl-2-methyl-1-oxa-4,9-diazaspiro[5.5]undecan-3-one maleic salt, having the following XRPD pattern:

| Pos. [°2θ] | Rel. Int. [%] | Pos. [°2θ] | Rel. Int. [%] |
|---|---|---|---|
| 8.9 | 32 | 17.8 | 100 |
| 11.8 | 39 | 18.0 | 54 |
| 15.4 | 34 | 23.6 | 20 |
| 16.2 | 33 | | |

In an embodiment, the invention refers to the polymorph P2 of the (R)-9-(2,5-difluorophenethyl)-4-ethyl-2-methyl-1-oxa-4,9-diazaspiro[5.5]undecan-3-one maleic salt, having the following XRPD pattern:

| Pos. [°2θ] | Rel. Int. [%] | Pos. [°2θ] | Rel. Int. [%] |
|---|---|---|---|
| 8.9 | 32 | 16.2 | 33 |
| 11.8 | 39 | 17.8 | 100 |
| 15.4 | 34 | 18.0 | 54 |

In an embodiment, the invention refers to the polymorph P2 of the (R)-9-(2,5-difluorophenethyl)-4-ethyl-2-methyl-1-oxa-4,9-diazaspiro[5.5]undecan-3-one maleic salt, having the following $^1$H-NMR (FIG. 17), where the 1:1 stoichiometry is determined:

RMN-$^1$H (CD$_3$OD, 400 MHz, δ): 7.19-7.13 (m, 2H, ArH); 7.10-7.04 (m, 1H, ArH); 6.26 (s, 2H, CH═); 4.23 (q, 1H, J=6.8 Hz, CH); 3.56-3.33 (m, 8H, CH$_2$); 3.28-3.11 (m, 4H, CH$_2$); 2.38-2.33 (m, 1H, CH$_2$); 2.07-1.80 (m, 3H, CH$_2$); 1.41 (d, J=6.8 Hz, 3H, CH$_3$); 1.15 (t, J=7.2 Hz, 3H, CH$_3$).

In an embodiment, the invention refers to the polymorph P2 of the (R)-9-(2,5-difluorophenethyl)-4-ethyl-2-methyl-1-oxa-4,9-diazaspiro[5.5]undecan-3-one maleic salt, having an endothermic peak at 171° C. (FIG. 18).

In an embodiment, the invention refers to the polymorph P3 of the (R)-9-(2,5-difluorophenethyl)-4-ethyl-2-methyl-1-oxa-4,9-diazaspiro[5.5]undecan-3-one maleic salt.

In an embodiment, the invention refers to the polymorph P3 of the (R)-9-(2,5-difluorophenethyl)-4-ethyl-2-methyl-1-oxa-4,9-diazaspiro[5.5]undecan-3-one maleic salt having the following XRPD pattern (FIG. 19):

| Pos. [°2θ] | Rel. Int. [%] | Pos. [°2θ] | Rel. Int. [%] |
|---|---|---|---|
| 4.4 | 3 | 20.0 | 7 |
| 9.1 | 29 | 22.3 | 2 |
| 10.3 | 12 | 22.6 | 2 |
| 11.8 | 13 | 23.6 | 16 |
| 13.2 | 6 | 24.3 | 1 |
| 13.6 | 15 | 25.4 | 3 |
| 15.5 | 12 | 25.7 | 8 |
| 16.0 | 14 | 26.7 | 18 |
| 16.5 | 4 | 30.0 | 1 |
| 17.4 | 25 | 31.3 | 3 |
| 17.7 | 100 | 32.4 | 2 |
| 18.1 | 9 | 35.9 | 4 |
| 19.5 | 4 | | |

In an embodiment, the invention refers to the polymorph P3 of the (R)-9-(2,5-difluorophenethyl)-4-ethyl-2-methyl-1-oxa-4,9-diazaspiro[5.5]undecan-3-one maleic salt, having the following XRPD pattern:

| Pos. [°2θ] | Rel. Int. [%] | Pos. [°2θ] | Rel. Int. [%] |
|---|---|---|---|
| 9.1 | 29 | 17.7 | 100 |
| 10.3 | 12 | 16.0 | 14 |
| 11.8 | 13 | 17.4 | 25 |
| 13.6 | 15 | 23.6 | 16 |
| 15.5 | 12 | 26.7 | 18 |

In an embodiment, the invention refers to the polymorph P3 of the (R)-9-(2,5-difluorophenethyl)-4-ethyl-2-methyl-1-oxa-4,9-diazaspiro[5.5]undecan-3-one maleic salt, having the following XRPD pattern:

| Pos. [°2θ] | Rel. Int. [%] |
|---|---|
| 9.1 | 29 |
| 17.4 | 25 |
| 17.7 | 100 |

In an embodiment, the invention refers to the polymorph P3 of the (R)-9-(2,5-difluorophenethyl)-4-ethyl-2-methyl-1-oxa-4,9-diazaspiro[5.5]undecan-3-one maleic salt, having the following $^1$H-NMR (FIG. 20), where the 1:1 stoichiometry was determined:

RMN-$^1$H (CD$_3$OD, 400 MHz, δ): 7.19-7.13 (m, 2H, ArH); 7.10-7.04 (m, 1H, ArH); 6.26 (s, 2H, CH═); 4.23 (q, 1H, J=6.8 Hz, CH); 3.56-3.33 (m, 8H, CH$_2$); 3.28-3.11 (m, 4H, CH$_2$); 2.38-2.33 (m, 1H, CH$_2$); 2.05-1.77 (m, 3H, CH$_2$); 1.41 (d, J=6.8 Hz, 3H, CH$_3$); 1.15 (t, J=7.2 Hz, 3H, CH$_3$).

In an embodiment, the invention refers to the polymorph P3 of the (R)-9-(2,5-difluorophenethyl)-4-ethyl-2-methyl-1-oxa-4,9-diazaspiro[5.5]undecan-3-one maleic salt, having an endothermic peak at 171° C. (FIG. 21).

In an embodiment, the invention refers to the polymorph P1 of the (R)-9-(2,5-difluorophenethyl)-4-ethyl-2-methyl-1-oxa-4,9-diazaspiro[5.5]undecan-3-one benzenesulfonic salt.

In an embodiment, the invention refers to the polymorph P1 of the (R)-9-(2,5-difluorophenethyl)-4-ethyl-2-methyl-1-oxa-4,9-diazaspiro[5.5]undecan-3-one benzenesulfonic salt, having the following XRPD pattern (FIG. 22):

| Pos. [°2θ] | Rel. Int. [%] | Pos. [°2θ] | Rel. Int. [%] |
|---|---|---|---|
| 6.0 | 100 | 20.6 | 7 |
| 9.6 | 4 | 21.2 | 1 |
| 10.6 | 2 | 21.9 | 6 |
| 12.1 | 4 | 22.7 | 1 |
| 12.6 | 4 | 23.6 | 23 |
| 13.9 | 9 | 24.0 | 2 |
| 14.3 | 13 | 24.3 | 3 |
| 14.8 | 23 | 24.8 | 11 |
| 15.1 | 11 | 25.2 | 4 |
| 15.9 | 18 | 25.5 | 10 |
| 16.6 | 3 | 25.9 | 4 |
| 16.9 | 6 | 28.3 | 2 |
| 17.5 | 18 | 28.8 | 3 |
| 18.1 | 12 | 30.8 | 1 |
| 18.5 | 23 | 33.6 | 2 |
| 19.4 | 39 | 37.7 | 1 |
| 19.7 | 8 | 39.2 | 1 |
| 20.4 | 8 | | |

In an embodiment, the invention refers to the polymorph P1 of the (R)-9-(2,5-difluorophenethyl)-4-ethyl-2-methyl-1-oxa-4,9-diazaspiro[5.5]undecan-3-one benzenesulfonic salt, having the following XRPD pattern:

| Pos. [°2θ] | Rel. Int. [%] |
|---|---|
| 6.0 | 100 |
| 14.3 | 13 |
| 14.8 | 23 |
| 15.1 | 11 |
| 15.9 | 18 |
| 17.5 | 18 |
| 18.1 | 12 |
| 18.5 | 23 |
| 19.4 | 39 |
| 23.6 | 23 |
| 24.8 | 11 |
| 25.5 | 10 |

In an embodiment, the invention refers to the polymorph P1 of the (R)-9-(2,5-difluorophenethyl)-4-ethyl-2-methyl-1-oxa-4,9-diazaspiro[5.5]undecan-3-one benzenesulfonic salt, having the following XRPD pattern:

| Pos. [°2θ] | Rel. Int. [%] |
|---|---|
| 6.0 | 100 |
| 14.8 | 23 |
| 18.5 | 23 |
| 19.4 | 39 |
| 23.6 | 23 |

In an embodiment, the invention refers to the polymorph P1 of the (R)-9-(2,5-difluorophenethyl)-4-ethyl-2-methyl-1-oxa-4,9-diazaspiro[5.5]undecan-3-one benzenesulfonic salt, having the following $^1$H-NMR (FIG. 23), where the 1:1 stoichiometry was determined:

RMN-$^1$H (CD$_3$OD, 400 MHz, δ): 7.85-7.82 (m, 2H, ArH); 7.45-7.40 (m, 3H, ArH); 7.19-7.13 (m, 2H, ArH); 7.10-7.04 (m, 1H, ArH); 4.22 (q, 1H, J=6.8 Hz, CH); 3.55-3.34 (m, 8H, CH$_2$); 3.26-3.11 (m, 4H, CH$_2$); 2.42-2.35 (m, 1H, CH$_2$); 2.05-1.77 (m, 3H, CH$_2$); 1.41 (d, J=6.8 Hz, 3H, CH$_3$); 1.14 (t, J=7.2 Hz, 3H, CH$_3$).

In an embodiment, the invention refers to the polymorph P1 of the (R)-9-(2,5-difluorophenethyl)-4-ethyl-2-methyl-1-oxa-4,9-diazaspiro[5.5]undecan-3-one benzenesulfonic salt, having an endothermic peak at 169° C. (FIG. 24).

In an embodiment, the invention refers to the polymorph P2 of the (R)-9-(2,5-difluorophenethyl)-4-ethyl-2-methyl-1-oxa-4,9-diazaspiro[5.5]undecan-3-one benzenesulfonic salt.

In an embodiment, the invention refers to the polymorph P2 of the (R)-9-(2,5-difluorophenethyl)-4-ethyl-2-methyl-1-oxa-4,9-diazaspiro[5.5]undecan-3-one benzenesulfonic salt, having the following XRPD pattern (FIG. 25):

| Pos. [°2θ] | Rel. Int. [%] | Pos. [°2θ] | Rel. Int. [%] |
|---|---|---|---|
| 6.1 | 100 | 19.9 | 8 |
| 9.2 | 1 | 21.7 | 1 |
| 12.3 | 3 | 23.5 | 3 |
| 13.2 | 4 | 24.1 | 1 |
| 13.7 | 5 | 24.8 | 6 |
| 14.3 | 6 | 25.3 | 1 |
| 14.5 | 6 | 25.9 | 2 |
| 14.9 | 10 | 27.0 | 1 |
| 15.9 | 2 | 27.6 | 1 |
| 17.0 | 2 | 28.2 | 2 |
| 17.5 | 5 | 28.5 | 1 |
| 18.6 | 16 | 29.4 | 1 |
| 18.9 | 11 | 32.3 | 1 |
| 19.3 | 4 | 34.5 | 1 |
| 19.5 | 2 | 35.5 | 1 |

In an embodiment, the invention refers to the polymorph P2 of the (R)-9-(2,5-difluorophenethyl)-4-ethyl-2-methyl-1-oxa-4,9-diazaspiro[5.5]undecan-3-one benzenesulfonic salt, having the following XRPD pattern:

| Pos. [°2θ] | Rel. Int. [%] | Pos. [°2θ] | Rel. Int. [%] |
|---|---|---|---|
| 6.1 | 100 | 17.5 | 5 |
| 13.7 | 5 | 18.6 | 16 |
| 14.3 | 6 | 18.9 | 11 |
| 14.5 | 6 | 19.9 | 8 |
| 14.9 | 10 | 24.8 | 6 |

In an embodiment, the invention refers to the polymorph P2 of the (R)-9-(2,5-difluorophenethyl)-4-ethyl-2-methyl-1-oxa-4,9-diazaspiro[5.5]undecan-3-one benzenesulfonic salt, having the following XRPD pattern:

| Pos. [°2θ] | Rel. Int. [%] |
|---|---|
| 6.1 | 100 |
| 14.9 | 10 |
| 18.6 | 16 |
| 18.9 | 11 |

In an embodiment, the invention refers to the polymorph P2 of the (R)-9-(2,5-difluorophenethyl)-4-ethyl-2-methyl-1-oxa-4,9-diazaspiro[5.5]undecan-3-one benzenesulfonic salt having the following $^1$H-NMR (FIG. 26), where the 1:1 stoichiometry was determined:

RMN-$^1$H (CD$_3$OD, 400 MHz, δ): 7.85-7.82 (m, 2H, ArH); 7.45-7.40 (m, 2H, ArH); 7.18-7.12 (m, 2H, ArH); 7.09-7.03 (m, 1H, ArH); 4.22 (q, 1H, J=6.8 Hz, CH); 3.54-3.35 (m, 4H, CH$_2$); 3.28-3.07 (m, 8H, CH$_2$); 2.38-2.28 (m, 1H, CH$_2$); 2.00-1.77 (m, 3H, CH$_2$); 1.40 (d, J=7.2 Hz, 3H, CH$_3$); 1.14 (t, J=6.8 Hz, 3H, CH$_3$).

In an embodiment, the invention refers to the polymorph P2 of the (R)-9-(2,5-difluorophenethyl)-4-ethyl-2-methyl-1- oxa-4,9-diazaspiro[5.5]undecan-3-one benzenesulfonic salt, having an endothermic peak at 160° C. (FIG. 27).

In an embodiment, the invention refers to the polymorph P1 of the (R)-9-(2,5-difluorophenethyl)-4-ethyl-2-methyl-1-oxa-4,9-diazaspiro[5.5]undecan-3-one phosphoric salt.

In an embodiment, the invention refers to the polymorph P1 of the (R)-9-(2,5-difluorophenethyl)-4-ethyl-2-methyl-1-oxa-4,9-diazaspiro[5.5]undecan-3-one phosphoric salt, having the following XRPD pattern (FIG. 28):

| Pos. [°2θ] | Rel. Int. [%] |
|---|---|
| 7.1 | 74 |
| 9.4 | 16 |
| 12.3 | 79 |
| 12.8 | 32 |
| 14.2 | 2 |
| 15.5 | 7 |
| 16.2 | 25 |
| 16.7 | 15 |
| 17.8 | 10 |
| 18.5 | 14 |
| 18.8 | 100 |
| 19.5 | 17 |
| 19.8 | 9 |
| 20.8 | 20 |
| 21.7 | 19 |
| 22.3 | 11 |
| 23.3 | 8 |
| 23.9 | 6 |
| 24.2 | 24 |
| 24.7 | 18 |
| 25.7 | 28 |
| 26.2 | 11 |
| 26.5 | 3 |
| 26.9 | 9 |
| 27.9 | 5 |
| 28.5 | 4 |
| 29.0 | 3 |
| 29.3 | 2 |
| 29.9 | 4 |
| 31.2 | 14 |
| 31.8 | 4 |
| 32.8 | 4 |
| 33.0 | 3 |
| 34.8 | 2 |
| 35.4 | 1 |
| 36.0 | 1 |
| 37.4 | 2 |
| 38.1 | 2 |
| 39.0 | 8 |

In an embodiment, the invention refers to the polymorph P1 of the (R)-9-(2,5-difluorophenethyl)-4-ethyl-2-methyl-1-oxa-4,9-diazaspiro[5.5]undecan-3-one phosphoric salt, having the following XRPD pattern:

| Pos. [°2θ] | Rel. Int. [%] |
|---|---|
| 7.1 | 74 |
| 9.4 | 16 |
| 12.3 | 79 |
| 12.8 | 32 |
| 16.2 | 25 |
| 16.7 | 15 |
| 17.8 | 10 |
| 18.5 | 14 |
| 18.8 | 100 |
| 19.5 | 17 |
| 20.8 | 20 |
| 21.7 | 19 |
| 22.3 | 11 |
| 24.2 | 24 |
| 24.7 | 18 |
| 25.7 | 28 |
| 26.2 | 11 |
| 31.2 | 14 |

In an embodiment, the invention refers to the polymorph P1 of the (R)-9-(2,5-difluorophenethyl)-4-ethyl-2-methyl-1-oxa-4,9-diazaspiro[5.5]undecan-3-one phosphoric salt, having the following XRPD pattern:

| Pos. [°2θ] | Rel. Int. [%] |
|---|---|
| 7.1 | 74 |
| 12.3 | 79 |
| 12.8 | 32 |
| 16.2 | 25 |
| 18.8 | 100 |
| 20.8 | 20 |
| 24.2 | 24 |
| 25.7 | 28 |

In an embodiment, the invention refers to the polymorph P1 of the (R)-9-(2,5-difluorophenethyl)-4-ethyl-2-methyl-1-oxa-4,9-diazaspiro[5.5]undecan-3-one phosphoric salt having the following XRPD pattern:

| Pos. [°2θ] | Rel. Int. [%] |
|---|---|
| 7.1 | 74 |
| 12.3 | 79 |
| 12.8 | 32 |
| 18.8 | 100 |

In an embodiment, the invention refers to the polymorph P1 of the (R)-9-(2,5-difluorophenethyl)-4-ethyl-2-methyl-1-oxa-4,9-diazaspiro[5.5]undecan-3-one phosphoric salt, having the following $^1$H-NMR (FIG. 29):

RMN-$^1$H (CD$_3$OD, 400 MHz, δ): 7.22-7.18 (m, 1H, ArH); 7.16-7.10 (m, 1H, ArH); 7.07-7.00 (m, 1H, ArH); 4.22 (q, 1H, J=6.8 Hz, CH); 3.74-3.71 (m, 1H, CH$_2$); 3.53-3.34 (m, 6H, CH$_2$); 3.29-3.05 (m, 4H, CH$_2$); 2.32-2.27 (m, 1H, CH$_2$); 2.18-2.11 (m, 1H, CH$_2$); 2.05-1.97 (m, 1H, CH$_2$); 1.89-1.83 (m, 2H, CH$_2$); 1.40 (d, J=6.8 Hz, 3H, CH$_3$); 1.15 (t, J=7.2 Hz, 3H, CH$_3$).

In an embodiment, the invention refers to the polymorph P1 of the (R)-9-(2,5-difluorophenethyl)-4-ethyl-2-methyl-1-oxa-4,9-diazaspiro[5.5]undecan-3-one phosphoric salt, having an endothermic peak at 223° C. (FIG. 30).

In an embodiment, the invention refers to the polymorph P1 of the (R)-9-(2,5-difluorophenethyl)-4-ethyl-2-methyl-1-oxa-4,9-diazaspiro[5.5]undecan-3-one sulfuric salt.

In an embodiment, the invention refers to the polymorph P1 of the (R)-9-(2,5-difluorophenethyl)-4-ethyl-2-methyl-1-oxa-4,9-diazaspiro[5.5]undecan-3-one sulfuric salt, having the following XRPD pattern (FIG. 31):

| Pos. [°2θ] | Rel. Int. [%] |
|---|---|
| 7.3 | 83 |
| 7.8 | 20 |
| 10.4 | 8 |
| 13.2 | 21 |
| 15.2 | 23 |
| 15.5 | 9 |
| 17.0 | 100 |

-continued

| Pos. [°2θ] | Rel. Int. [%] |
|---|---|
| 17.6 | 6 |
| 18.4 | 10 |
| 20.2 | 24 |
| 21.0 | 64 |
| 22.1 | 10 |
| 23.2 | 8 |
| 23.4 | 4 |
| 23.8 | 13 |
| 24.4 | 23 |
| 25.7 | 8 |
| 26.7 | 8 |
| 32.2 | 4 |
| 33.1 | 7 |
| 34.7 | 2 |

In an embodiment, the invention refers to the polymorph P1 of the (R)-9-(2,5-difluorophenethyl)-4-ethyl-2-methyl-1-oxa-4,9-diazaspiro[5.5]undecan-3-one sulfuric salt, having the following XRPD pattern:

| Pos. [°2θ] | Rel. Int. [%] |
|---|---|
| 7.3 | 83 |
| 7.8 | 20 |
| 13.2 | 21 |
| 15.2 | 23 |
| 17.0 | 100 |
| 18.4 | 10 |
| 20.2 | 24 |
| 21.0 | 64 |
| 22.1 | 10 |
| 23.8 | 13 |
| 24.4 | 23 |

In an embodiment, the invention refers to the polymorph P1 of the (R)-9-(2,5-difluorophenethyl)-4-ethyl-2-methyl-1-oxa-4,9-diazaspiro[5.5]undecan-3-one sulfuric salt, having the following XRPD pattern:

| Pos. [°2θ] | Rel. Int. [%] |
|---|---|
| 7.3 | 83 |
| 7.8 | 20 |
| 13.2 | 21 |
| 15.2 | 23 |
| 17.0 | 100 |
| 20.2 | 24 |
| 21.0 | 64 |

In an embodiment, the invention refers to the polymorph P1 of the (R)-9-(2,5-difluorophenethyl)-4-ethyl-2-methyl-1-oxa-4,9-diazaspiro[5.5]undecan-3-one sulfuric salt, having the following XRPD pattern:

| Pos. [°2θ] | Rel. Int. [%] |
|---|---|
| 7.3 | 83 |
| 15.2 | 23 |
| 17.0 | 100 |
| 21.0 | 64 |

In an embodiment, the invention refers to the polymorph P1 of the (R)-9-(2,5-difluorophenethyl)-4-ethyl-2-methyl-1-oxa-4,9-diazaspiro[5.5]undecan-3-one sulfuric salt having the following $^1$H-NMR (FIG. 32):

RMN-$^1$H (CD$_3$OD, 400 MHz, δ): 7.20-7.13 (m, 2H, ArH); 7.10-7.04 (m, 1H, ArH); 4.23 (q, 1H, J=6.8 Hz, CH); 3.60-3.34 (m, 8H, CH$_2$); 3.27-3.14 (m, 4H, CH$_2$); 2.42-2.38 (m, 1H, CH$_2$); 2.09-2.01 (m, 1H, CH$_2$); 1.95-1.84 (m, 2H, CH$_2$); 1.41 (d, J=6.8 Hz, 3H, CH$_3$); 1.15 (t, J=7.2 Hz, 3H, CH$_3$).

In an embodiment, the invention refers to the polymorph P1 of the (R)-9-(2,5-difluorophenethyl)-4-ethyl-2-methyl-1-oxa-4,9-diazaspiro[5.5]undecan-3-one sulfuric salt having an endothermic peak at 167° C. (FIG. 33).

In an embodiment, the invention refers to the polymorph P1 of the (R)-9-(2,5-difluorophenethyl)-4-ethyl-2-methyl-1-oxa-4,9-diazaspiro[5.5]undecan-3-one succinic salt.

In an embodiment, the invention refers to the polymorph P1 of the (R)-9-(2,5-difluorophenethyl)-4-ethyl-2-methyl-1-oxa-4,9-diazaspiro[5.5]undecan-3-one succinic salt, having the following XRPD pattern (FIG. 34):

| Pos. [°2θ] | Rel. Int. [%] |
|---|---|
| 6.5 | 36 |
| 6.8 | 26 |
| 8.8 | 100 |
| 11.5 | 27 |
| 11.8 | 67 |
| 13.6 | 27 |
| 14.4 | 13 |
| 14.9 | 31 |
| 15.5 | 15 |
| 15.9 | 8 |
| 17.1 | 83 |
| 17.5 | 85 |
| 18.2 | 57 |
| 18.7 | 30 |
| 19.0 | 13 |
| 19.8 | 20 |
| 20.4 | 30 |
| 21.1 | 5 |
| 22.3 | 23 |
| 22.8 | 8 |
| 23.2 | 11 |
| 23.6 | 19 |
| 23.9 | 27 |
| 24.4 | 22 |
| 24.6 | 38 |
| 25.3 | 6 |
| 25.9 | 23 |
| 26.5 | 6 |
| 27.2 | 7 |
| 29.1 | 5 |
| 32.2 | 2 |
| 33.9 | 7 |
| 35.5 | 3 |

In an embodiment, the invention refers to the polymorph P1 of the (R)-9-(2,5-difluorophenethyl)-4-ethyl-2-methyl-1-oxa-4,9-diazaspiro[5.5]undecan-3-one succinic salt having the following XRPD pattern:

| Pos. [°2θ] | Rel. Int. [%] |
|---|---|
| 6.5 | 36 |
| 6.8 | 26 |
| 8.8 | 100 |
| 11.5 | 27 |
| 11.8 | 67 |
| 13.6 | 27 |
| 14.4 | 13 |
| 14.9 | 31 |
| 15.5 | 15 |
| 17.1 | 83 |
| 17.5 | 85 |
| 18.2 | 57 |
| 18.7 | 30 |
| 19.0 | 13 |
| 19.8 | 20 |

-continued

| Pos. [°2θ] | Rel. Int. [%] |
|---|---|
| 20.4 | 30 |
| 22.3 | 23 |
| 23.2 | 11 |
| 23.6 | 19 |
| 23.9 | 27 |
| 24.4 | 22 |
| 24.6 | 38 |
| 25.9 | 23 |

In an embodiment, the invention refers to the polymorph P1 of the (R)-9-(2,5-difluorophenethyl)-4-ethyl-2-methyl-1-oxa-4,9-diazaspiro[5.5]undecan-3-one succinic salt, having the following XRPD pattern:

| Pos. [°2θ] | Rel. Int. [%] |
|---|---|
| 6.5 | 36 |
| 6.8 | 26 |
| 8.8 | 100 |
| 11.5 | 27 |
| 11.8 | 67 |
| 13.6 | 27 |
| 14.9 | 31 |
| 17.1 | 83 |
| 17.5 | 85 |
| 20.4 | 30 |
| 18.2 | 57 |
| 18.7 | 30 |
| 19.8 | 20 |
| 22.3 | 23 |
| 23.9 | 27 |
| 24.4 | 22 |
| 24.6 | 38 |
| 25.9 | 23 |

In an embodiment, the invention refers to the polymorph P1 of the (R)-9-(2,5-difluorophenethyl)-4-ethyl-2-methyl-1-oxa-4,9-diazaspiro[5.5]undecan-3-one succinic salt, having the following XRPD pattern:

| Pos. [°2θ] | Rel. Int. [%] |
|---|---|
| 6.5 | 36 |
| 8.8 | 100 |
| 11.8 | 67 |
| 14.9 | 31 |
| 17.1 | 83 |
| 17.5 | 85 |
| 18.2 | 57 |
| 18.7 | 30 |
| 20.4 | 30 |
| 24.6 | 38 |

In an embodiment, the invention refers to the polymorph P1 of the (R)-9-(2,5-difluorophenethyl)-4-ethyl-2-methyl-1-oxa-4,9-diazaspiro[5.5]undecan-3-one succinic salt, having the following XRPD pattern:

| Pos. [°2θ] | Rel. Int. [%] |
|---|---|
| 8.8 | 100 |
| 11.8 | 67 |
| 17.1 | 83 |
| 17.5 | 85 |
| 18.2 | 57 |

In an embodiment, the invention refers to the polymorph P1 of the (R)-9-(2,5-difluorophenethyl)-4-ethyl-2-methyl-1-oxa-4,9-diazaspiro[5.5]undecan-3-one succinic salt having the following $^1$H-NMR (FIG. 35):

RMN-$^1$H (CD$_3$OD, 400 MHz, δ): 7.12-7.07 (m, 2H, ArH); 7.02-7.00 (m, 1H, ArH); 4.19 (q, 1H, J=6.8 Hz, CH); 3.53-3.44 (m, 2H, CH$_2$); 3.40-3.32 (m, 1H, CH$_2$); 3.23-3.20 (m, 1H, CH$_2$); 3.12-2.85 (m, 7H, CH$_2$); 2.77-2.68 (m, 1H, CH$_2$); 2.54 (2, 4H, CH$_2$); 2.21-2.15 (m, 1H, CH$_2$); 1.90-1.83 (m, 1H, CH$_2$); 1.80-1.70 (m, 2H, CH$_2$); 1.38 (d, J=6.8 Hz, 3H, CH$_3$); 1.13 (t, J=7.2 Hz, 3H, CH$_3$).

In an embodiment, the invention refers to the polymorph P1 of the (R)-9-(2,5-difluorophenethyl)-4-ethyl-2-methyl-1-oxa-4,9-diazaspiro[5.5]undecan-3-one succinic salt, having an endothermic peak at 132° C. (FIG. 36).

In an embodiment, the invention refers to the polymorph P1 of the (R)-9-(2,5-difluorophenethyl)-4-ethyl-2-methyl-1-oxa-4,9-diazaspiro[5.5]undecan-3-one oxalic salt.

In an embodiment, the invention refers to the polymorph P1 of the (R)-9-(2,5-difluorophenethyl)-4-ethyl-2-methyl-1-oxa-4,9-diazaspiro[5.5]undecan-3-one oxalic salt, having the following XRPD pattern (FIG. 37):

| Pos. [°2θ] | Rel. Int. [%] |
|---|---|
| 6.9 | 78 |
| 9.2 | 32 |
| 12.0 | 100 |
| 12.6 | 7 |
| 16.0 | 65 |
| 17.2 | 22 |
| 18.6 | 96 |
| 21.1 | 66 |
| 21.9 | 20 |
| 23.1 | 19 |
| 23.2 | 15 |
| 24.5 | 21 |
| 25.4 | 44 |
| 28.0 | 9 |

In an embodiment, the invention refers to the polymorph P1 of the (R)-9-(2,5-difluorophenethyl)-4-ethyl-2-methyl-1-oxa-4,9-diazaspiro[5.5]undecan-3-one oxalic salt having the following XRPD pattern:

| Pos. [°2θ] | Rel. Int. [%] |
|---|---|
| 6.9 | 78 |
| 9.2 | 32 |
| 12.0 | 100 |
| 16.0 | 65 |
| 17.2 | 22 |
| 18.6 | 96 |
| 21.1 | 66 |
| 21.9 | 20 |
| 23.1 | 19 |
| 23.2 | 15 |
| 24.5 | 21 |
| 25.4 | 44 |

In an embodiment, the invention refers to the polymorph P1 of the (R)-9-(2,5-difluorophenethyl)-4-ethyl-2-methyl-1-oxa-4,9-diazaspiro[5.5]undecan-3-one oxalic salt having the following XRPD pattern:

| Pos. [°2θ] | Rel. Int. [%] |
|---|---|
| 6.9 | 78 |
| 9.2 | 32 |
| 12.0 | 100 |
| 16.0 | 65 |

| Pos. [°2θ] | Rel. Int. [%] |
|---|---|
| 17.2 | 22 |
| 18.6 | 96 |
| 21.1 | 66 |
| 21.9 | 20 |
| 24.5 | 21 |
| 25.4 | 44 |

In an embodiment, the invention refers to the polymorph P1 of the (R)-9-(2,5-difluorophenethyl)-4-ethyl-2-methyl-1-oxa-4,9-diazaspiro[5.5]undecan-3-one oxalic salt having the following XRPD pattern:

| Pos. [°2θ] | Rel. Int. [%] |
|---|---|
| 6.9 | 78 |
| 9.2 | 32 |
| 12.0 | 100 |
| 16.0 | 65 |
| 18.6 | 96 |
| 21.1 | 66 |
| 25.4 | 44 |

In an embodiment, the invention refers to the polymorph P1 of the (R)-9-(2,5-difluorophenethyl)-4-ethyl-2-methyl-1-oxa-4,9-diazaspiro[5.5]undecan-3-one oxalic salt having the following XRPD pattern:

| Pos. [°2θ] | Rel. Int. [%] |
|---|---|
| 6.9 | 78 |
| 12.0 | 100 |
| 16.0 | 65 |
| 18.6 | 96 |
| 21.1 | 66 |

In an embodiment, the invention refers to the polymorph P1 of the (R)-9-(2,5-difluorophenethyl)-4-ethyl-2-methyl-1-oxa-4,9-diazaspiro[5.5]undecan-3-one oxalic salt, having the following $^1$H-NMR (FIG. 38):

RMN-$^1$H (CD$_3$OD, 400 MHz, δ): 7.18-7.12 (m, 2H, ArH); 7.09-7.03 (m, 1H, ArH); 4.23 (q, 1H, J=6.8 Hz, CH); 3.56-3.33 (m, 8H, CH$_2$); 3.28-3.11 (m, 4H, CH$_2$); 2.38-2.33 (m, 1H, CH$_2$); 2.08-2.00 (m, 1H, CH$_2$); 1.93-1.84 (m, 2H, CH$_2$); 1.41 (d, J=7.2 Hz, 3H, CH$_3$); 1.14 (t, J=6.8 Hz, 3H, CH$_3$).

In an embodiment, the invention refers to the polymorph P1 of the (R)-9-(2,5-difluorophenethyl)-4-ethyl-2-methyl-1-oxa-4,9-diazaspiro[5.5]undecan-3-one oxalic salt, having an endothermic peak at 188° C. (FIG. 39).

In an embodiment, the invention refers to the polymorph P2 of the (R)-9-(2,5-difluorophenethyl)-4-ethyl-2-methyl-1-oxa-4,9-diazaspiro[5.5]undecan-3-one oxalic salt.

In an embodiment, the invention refers to the polymorph P2 of the (R)-9-(2,5-difluorophenethyl)-4-ethyl-2-methyl-1-oxa-4,9-diazaspiro[5.5]undecan-3-one oxalic salt, having the following XRPD pattern (FIG. 40):

| Pos. [°2θ] | Rel. Int. [%] |
|---|---|
| 3.7 | 13 |
| 7.4 | 100 |
| 11.1 | 7 |
| 11.5 | 5 |
| 12.3 | 49 |
| 14.4 | 45 |
| 14.9 | 16 |
| 16.3 | 14 |
| 16.7 | 8 |
| 17.1 | 7 |
| 17.9 | 30 |
| 18.7 | 85 |
| 20.1 | 3 |
| 20.9 | 9 |
| 22.0 | 21 |
| 22.6 | 14 |
| 23.5 | 13 |
| 25.1 | 24 |
| 26.3 | 48 |
| 27.9 | 4 |
| 30.2 | 6 |
| 32.1 | 2 |
| 36.1 | 1 |

In an embodiment, the invention refers to the polymorph P2 of the (R)-9-(2,5-difluorophenethyl)-4-ethyl-2-methyl-1-oxa-4,9-diazaspiro[5.5]undecan-3-one oxalic salt, having the following XRPD pattern:

| Pos. [°2θ] | Rel. Int. [%] |
|---|---|
| 3.7 | 13 |
| 7.4 | 100 |
| 12.3 | 49 |
| 14.4 | 45 |
| 14.9 | 16 |
| 16.3 | 14 |
| 17.9 | 30 |
| 18.7 | 85 |
| 22.0 | 21 |
| 22.6 | 14 |
| 23.5 | 13 |
| 25.1 | 24 |
| 26.3 | 48 |

In an embodiment, the invention refers to the polymorph P2 of the (R)-9-(2,5-difluorophenethyl)-4-ethyl-2-methyl-1-oxa-4,9-diazaspiro[5.5]undecan-3-one oxalic salt, having the following XRPD pattern:

| Pos. [°2θ] | Rel. Int. [%] |
|---|---|
| 7.4 | 100 |
| 12.3 | 49 |
| 14.4 | 45 |
| 17.9 | 30 |
| 18.7 | 85 |
| 22.0 | 21 |
| 25.1 | 24 |
| 26.3 | 48 |

In an embodiment, the invention refers to the polymorph P2 of the (R)-9-(2,5-difluorophenethyl)-4-ethyl-2-methyl-1-oxa-4,9-diazaspiro[5.5]undecan-3-one oxalic salt, having the following XRPD pattern:

| Pos. [°2θ] | Rel. Int. [%] |
|---|---|
| 7.4 | 100 |
| 12.3 | 49 |
| 14.4 | 45 |

-continued

| Pos. [°2θ] | Rel. Int. [%] |
|---|---|
| 18.7 | 85 |
| 26.3 | 48 |

In an embodiment, the invention refers to the polymorph P2 of the (R)-9-(2,5-difluorophenethyl)-4-ethyl-2-methyl-1-oxa-4,9-diazaspiro[5.5]undecan-3-one oxalic salt, having the following $^1$H-NMR (FIG. 41):

RMN-$^1$H (CD$_3$OD, 400 MHz, δ): 7.18-7.12 (m, 2H, ArH); 7.09-7.03 (m, 1H, ArH); 4.23 (q, 1H, J=6.8 Hz, CH); 3.56-3.33 (m, 8H, CH$_2$); 3.28-3.11 (m, 4H, CH$_2$); 2.38-2.33 (m, 1H, CH$_2$); 2.08-2.00 (m, 1H, CH$_2$); 1.93-1.84 (m, 2H, CH$_2$); 1.41 (d, J=7.2 Hz, 3H, CH$_3$); 1.14 (t, J=6.8 Hz, 3H, CH$_3$).

In an embodiment, the invention refers to the polymorph P2 of the (R)-9-(2,5-difluorophenethyl)-4-ethyl-2-methyl-1-oxa-4,9-diazaspiro[5.5]undecan-3-one oxalic salt, having an endothermic peak at 188° C. (FIG. 42).

In an embodiment, the invention refers to the polymorph P1 of the (R)-9-(2,5-difluorophenethyl)-4-ethyl-2-methyl-1-oxa-4,9-diazaspiro[5.5]undecan-3-one malonic salt.

In an embodiment, the invention refers to the polymorph P1 of the (R)-9-(2,5-difluorophenethyl)-4-ethyl-2-methyl-1-oxa-4,9-diazaspiro[5.5]undecan-3-one malonic salt, having the following XRPD pattern (FIG. 43):

| Pos. [°2θ] | Rel. Int. [%] |
|---|---|
| 6.6 | 8 |
| 8.9 | 30 |
| 11.6 | 15 |
| 11.8 | 23 |
| 12.3 | 4 |
| 13.6 | 9 |
| 14.6 | 7 |
| 15.5 | 17 |
| 16.2 | 5 |
| 16.7 | 3 |
| 17.2 | 100 |
| 17.8 | 31 |
| 18.2 | 21 |
| 19.0 | 6 |
| 20.8 | 10 |
| 21.1 | 8 |
| 22.3 | 11 |
| 22.5 | 9 |
| 23.1 | 13 |
| 23.5 | 5 |
| 24.5 | 21 |
| 25.3 | 20 |
| 25.9 | 17 |
| 26.3 | 8 |
| 27.0 | 5 |
| 27.6 | 6 |
| 28.5 | 6 |
| 29.2 | 2 |
| 29.7 | 3 |
| 31.1 | 5 |
| 32.3 | 3 |
| 32.8 | 3 |
| 34.9 | 3 |
| 36.7 | 4 |
| 38.3 | 1 |

In an embodiment, the invention refers to the polymorph P1 of the (R)-9-(2,5-difluorophenethyl)-4-ethyl-2-methyl-1-oxa-4,9-diazaspiro[5.5]undecan-3-one malonic salt, having the following XRPD pattern:

| Pos. [°2θ] | Rel. Int. [%] |
|---|---|
| 8.9 | 30 |
| 11.6 | 15 |
| 11.8 | 23 |
| 23.1 | 13 |
| 15.5 | 17 |
| 17.2 | 100 |
| 17.8 | 31 |
| 18.2 | 21 |
| 20.8 | 10 |
| 22.3 | 11 |
| 24.5 | 21 |
| 25.3 | 20 |
| 25.9 | 17 |

In an embodiment, the invention refers to the polymorph P1 of the (R)-9-(2,5-difluorophenethyl)-4-ethyl-2-methyl-1-oxa-4,9-diazaspiro[5.5]undecan-3-one malonic salt, having the following XRPD pattern:

| Pos. [°2θ] | Rel. Int. [%] |
|---|---|
| 8.9 | 30 |
| 11.8 | 23 |
| 17.2 | 100 |
| 17.8 | 31 |
| 18.2 | 21 |
| 24.5 | 21 |
| 25.3 | 20 |

In an embodiment, the invention refers to the polymorph P1 of the (R)-9-(2,5-difluorophenethyl)-4-ethyl-2-methyl-1-oxa-4,9-diazaspiro[5.5]undecan-3-one malonic salt, having the following $^1$H-NMR (FIG. 44), where the 1:1 stoichiometry was determined:

RMN-$^1$H (CDCl$_3$, 400 MHz, δ): 7.06-6.93 (m, 3H, ArH); 4.12 (q, 1H, J=6.8 Hz, CH); 3.53-3.35 (m, 5H, CH$_2$); 3.21 (s, 2H, CH$_2$); 3.20-3.07 (m, 6H, CH$_2$); 2.96-2.90 (m, 1H, CH$_2$); 2.31-2.24 (m, 1H, CH$_2$); 2.23-2.14 (m, 1H, CH$_2$); 2.07-1.99 (m, 1H, CH$_2$); 1.88-1.83 (m, 1H, CH$_2$); 1.45 (d, J=6.8 Hz, 3H, CH$_3$); 1.14 (t, J=7.2 Hz, 3H, CH$_3$).

In an embodiment, the invention refers to the polymorph P1 of the (R)-9-(2,5-difluorophenethyl)-4-ethyl-2-methyl-1-oxa-4,9-diazaspiro[5.5]undecan-3-one malonic salt, having an endothermic peak at 144° C. (FIG. 45).

In an embodiment, the invention refers to the polymorph P1 of the (R)-9-(2,5-difluorophenethyl)-4-ethyl-2-methyl-1-oxa-4,9-diazaspiro[5.5]undecan-3-one ethanesulfonic salt.

In an embodiment, the invention refers to the polymorph P1 of the (R)-9-(2,5-difluorophenethyl)-4-ethyl-2-methyl-1-oxa-4,9-diazaspiro[5.5]undecan-3-one ethanesulfonic salt, having the following XRPD pattern (FIG. 46):

| Pos. [°2θ] | Rel. Int. [%] |
|---|---|
| 6.4 | 100 |
| 9.8 | 8 |
| 12.2 | 9 |
| 13.6 | 8 |
| 14.1 | 6 |
| 14.5 | 13 |
| 14.9 | 5 |
| 15.2 | 7 |
| 15.5 | 16 |
| 17.1 | 17 |
| 17.6 | 20 |
| 17.8 | 50 |
| 19.2 | 47 |
| 19.4 | 26 |

-continued

| Pos. [°2θ] | Rel. Int. [%] |
|---|---|
| 20.2 | 17 |
| 20.8 | 22 |
| 21.5 | 26 |
| 22.0 | 12 |
| 23.4 | 14 |
| 23.8 | 12 |
| 25.2 | 6 |
| 25.5 | 5 |
| 27.1 | 2 |
| 27.7 | 4 |
| 28.6 | 12 |
| 29.1 | 2 |
| 30.1 | 4 |
| 32.1 | 2 |
| 32.5 | 3 |
| 33.4 | 6 |
| 34.4 | 1 |
| 35.2 | 1 |
| 36.5 | 1 |
| 38.0 | 2 |
| 38.8 | 2 |

In an embodiment, the invention refers to the polymorph P1 of the (R)-9-(2,5-difluorophenethyl)-4-ethyl-2-methyl-1-oxa-4,9-diazaspiro[5.5]undecan-3-one ethanesulfonic salt, having the following XRPD pattern:

| Pos. [°2θ] | Rel. Int. [%] |
|---|---|
| 6.4 | 100 |
| 14.5 | 13 |
| 15.5 | 16 |
| 17.1 | 17 |
| 17.6 | 20 |
| 17.8 | 50 |
| 19.2 | 47 |
| 19.4 | 26 |
| 20.2 | 17 |
| 20.8 | 22 |
| 21.5 | 26 |
| 22.0 | 12 |
| 23.4 | 14 |
| 23.8 | 12 |
| 28.6 | 12 |

In an embodiment, the invention refers to the polymorph P1 of the (R)-9-(2,5-difluorophenethyl)-4-ethyl-2-methyl-1-oxa-4,9-diazaspiro[5.5]undecan-3-one ethanesulfonic salt, having the following XRPD pattern:

| Pos. [°2θ] | Rel. Int. [%] |
|---|---|
| 6.4 | 100 |
| 17.6 | 20 |
| 17.8 | 50 |
| 19.2 | 47 |
| 19.4 | 26 |
| 20.8 | 22 |
| 21.5 | 26 |

In an embodiment, the invention refers to the polymorph P1 of the (R)-9-(2,5-difluorophenethyl)-4-ethyl-2-methyl-1-oxa-4,9-diazaspiro[5.5]undecan-3-one ethanesulfonic salt, having the following XRPD pattern:

| Pos. [°2θ] | Rel. Int. [%] |
|---|---|
| 6.4 | 100 |
| 17.8 | 50 |
| 19.2 | 47 |

In an embodiment, the invention refers to the polymorph P1 of the (R)-9-(2,5-difluorophenethyl)-4-ethyl-2-methyl-1-oxa-4,9-diazaspiro[5.5]undecan-3-one ethanesulfonic salt, having the following $^1$H-NMR FIG. 47), where the 1:1 stoichiometry was determined:

RMN-$^1$H (CD$_3$OD, 400 MHz, δ): 7.19-7.14 (m, 2H, ArH); 7.10-7.03 (m, 1H, ArH); 4.23 (q, 1H, J=6.8 Hz, CH); 3.60-3.33 (m, 8H, CH$_2$); 3.27-3.13 (m, 4H, CH$_2$); 2.81 (q, 2H, J=7.2 Hz, CH$_2$); 2.38-2.33 (m, 1H, CH$_2$); 2.08-1.82 (m, 3H, CH$_2$); 1.41 (d, J=7.2 Hz, 3H, CH$_3$); 1.31 (t, 3H, J=7.2 Hz, CH); 1.15 (t, J=6.8 Hz, 3H, CH$_3$).

In an embodiment, the invention refers to the polymorph P1 of the (R)-9-(2,5-difluorophenethyl)-4-ethyl-2-methyl-1-oxa-4,9-diazaspiro[5.5]undecan-3-one ethanesulfonic salt, having an endothermic peak at 124° C. (FIG. 48)

In an embodiment, the invention refers to the polymorph P1 of the (R)-9-(2,5-difluorophenethyl)-4-ethyl-2-methyl-1-oxa-4,9-diazaspiro[5.5]undecan-3-one methanesulfonic salt.

In an embodiment, the invention refers to the polymorph P1 of the (R)-9-(2,5-difluorophenethyl)-4-ethyl-2-methyl-1-oxa-4,9-diazaspiro[5.5]undecan-3-one nitric salt.

In an embodiment, the invention refers to the polymorph P1 of the (R)-9-(2,5-difluorophenethyl)-4-ethyl-2-methyl-1-oxa-4,9-diazaspiro[5.5]undecan-3-one nitric salt, having the following XRPD pattern (FIG. 49):

| Pos. [°2θ] | Rel. Int. [%] |
|---|---|
| 7.4 | 45 |
| 8.6 | 12 |
| 11.2 | 21 |
| 11.6 | 18 |
| 12.8 | 60 |
| 13.5 | 24 |
| 13.6 | 28 |
| 14.8 | 7 |
| 15.4 | 39 |
| 15.6 | 14 |
| 16.9 | 15 |
| 17.5 | 62 |
| 18.2 | 26 |
| 18.6 | 100 |
| 19.1 | 5 |
| 20.3 | 8 |
| 21.2 | 29 |
| 22.5 | 20 |
| 22.8 | 11 |
| 23.6 | 10 |
| 24.7 | 15 |
| 24.9 | 15 |
| 25.7 | 8 |
| 25.9 | 26 |
| 26.2 | 10 |
| 27.2 | 5 |
| 27.5 | 5 |
| 27.9 | 8 |
| 28.3 | 8 |
| 28.8 | 6 |
| 29.9 | 3 |
| 30.8 | 14 |
| 34.2 | 5 |
| 37.0 | 2 |
| 37.6 | 2 |

In an embodiment, the invention refers to the polymorph P1 of the (R)-9-(2,5-difluorophenethyl)-4-ethyl-2-methyl-1-oxa-4,9-diazaspiro[5.5]undecan-3-one nitric salt, having the following XRPD pattern:

| Pos. [°2θ] | Rel. Int. [%] |
| --- | --- |
| 7.4 | 45 |
| 8.6 | 12 |
| 11.2 | 21 |
| 11.6 | 18 |
| 12.8 | 60 |
| 13.5 | 24 |
| 13.6 | 28 |
| 15.4 | 39 |
| 15.6 | 14 |
| 16.9 | 15 |
| 17.5 | 62 |
| 18.2 | 26 |
| 22.8 | 11 |
| 23.6 | 10 |
| 24.7 | 15 |
| 18.6 | 100 |
| 21.2 | 29 |
| 22.5 | 20 |
| 24.9 | 15 |
| 25.9 | 26 |
| 26.2 | 10 |
| 30.8 | 14 |

In an embodiment, the invention refers to the polymorph P1 of the (R)-9-(2,5-difluorophenethyl)-4-ethyl-2-methyl-1-oxa-4,9-diazaspiro[5.5]undecan-3-one nitric salt, having the following XRPD pattern:

| Pos. [°2θ] | Rel. Int. [%] |
| --- | --- |
| 7.4 | 45 |
| 11.2 | 21 |
| 12.8 | 60 |
| 13.5 | 24 |
| 13.6 | 28 |
| 15.4 | 39 |
| 17.5 | 62 |
| 18.2 | 26 |
| 18.6 | 100 |
| 21.2 | 29 |
| 22.5 | 20 |
| 25.9 | 26 |

In an embodiment, the invention refers to the polymorph P1 of the (R)-9-(2,5-difluorophenethyl)-4-ethyl-2-methyl-1-oxa-4,9-diazaspiro[5.5]undecan-3-one nitric salt, having the following XRPD pattern:

| Pos. [°2θ] | Rel. Int. [%] |
| --- | --- |
| 7.4 | 45 |
| 12.8 | 60 |
| 15.4 | 39 |
| 17.5 | 62 |
| 18.6 | 100 |

In an embodiment, the invention refers to the polymorph P1 of the (R)-9-(2,5-difluorophenethyl)-4-ethyl-2-methyl-1-oxa-4,9-diazaspiro[5.5]undecan-3-one nitric salt, having the following XRPD pattern:

| Pos. [°2θ] | Rel. Int. [%] |
| --- | --- |
| 7.4 | 45 |
| 12.8 | 60 |
| 17.5 | 62 |
| 18.6 | 100 |

In an embodiment, the invention refers to the polymorph P1 of the (R)-9-(2,5-difluorophenethyl)-4-ethyl-2-methyl-1-oxa-4,9-diazaspiro[5.5]undecan-3-one nitric salt, having the following $^1$H-NMR (FIG. 50):

RMN-$^1$H (CD$_3$OD, 400 MHz, δ): 7.19-7.13 (m, 2H, ArH); 7.10-7.03 (m, 1H, ArH); 4.23 (q, 1H, J=6.8 Hz, CH); 3.55-3.33 (m, 8H, CH$_2$); 3.28-3.24 (m, 2H, CH$_2$); 3.14-3.10 (m, 2H, CH$_2$); 2.40-2.28 (m, 1H, CH$_2$); 2.08-1.74 (m, 3H, CH$_2$); 1.41 (d, J=6.8 Hz, 3H, CH$_3$); 1.14 (t, J=7.2 Hz, 3H, CH$_3$).

In an embodiment, the invention refers to the polymorph P1 of the (R)-9-(2,5-difluorophenethyl)-4-ethyl-2-methyl-1-oxa-4,9-diazaspiro[5.5]undecan-3-one nitric salt, having an endothermic peak at 175° C. (FIG. 51).

In an embodiment, the invention refers to the polymorph P1 of the (R)-9-(2,5-difluorophenethyl)-4-ethyl-2-methyl-1-oxa-4,9-diazaspiro[5.5]undecan-3-one S(+)-mandelic salt.

In an embodiment, the invention refers to the polymorph P1 of the (R)-9-(2,5-difluorophenethyl)-4-ethyl-2-methyl-1-oxa-4,9-diazaspiro[5.5]undecan-3-one S(+)-mandelic salt, having the following XRPD pattern (FIG. 52):

| Pos. [°2θ] | Rel. Int. [%] |
| --- | --- |
| 8.6 | 42 |
| 8.9 | 56 |
| 9.1 | 61 |
| 10.0 | 11 |
| 10.5 | 11 |
| 13.2 | 28 |
| 13.4 | 22 |
| 13.8 | 35 |
| 15.1 | 28 |
| 15.4 | 44 |
| 15.9 | 100 |
| 16.3 | 76 |
| 17.4 | 19 |
| 18.1 | 60 |
| 18.9 | 35 |
| 19.7 | 17 |
| 20.2 | 13 |
| 20.6 | 37 |
| 21.2 | 43 |
| 22.0 | 20 |
| 22.5 | 14 |
| 23.0 | 39 |
| 23.9 | 28 |
| 24.2 | 34 |
| 24.5 | 14 |
| 26.8 | 4 |
| 27.7 | 14 |
| 28.4 | 12 |
| 29.3 | 10 |
| 32.1 | 3 |

In an embodiment, the invention refers to the polymorph P1 of the (R)-9-(2,5-difluorophenethyl)-4-ethyl-2-methyl-1-oxa-4,9-diazaspiro[5.5]undecan-3-one S(+)-mandelic salt, having the following XRPD pattern:

| Pos. [°2θ] | Rel. Int. [%] |
| --- | --- |
| 8.6 | 42 |
| 8.9 | 56 |

-continued

| Pos. [°2θ] | Rel. Int. [%] |
|---|---|
| 9.1 | 61 |
| 13.2 | 28 |
| 13.4 | 22 |
| 13.8 | 35 |
| 15.1 | 28 |
| 15.4 | 44 |
| 15.9 | 100 |
| 16.3 | 76 |
| 17.4 | 19 |
| 18.1 | 60 |
| 18.9 | 35 |
| 19.7 | 17 |
| 20.6 | 37 |
| 21.2 | 43 |
| 22.0 | 20 |
| 23.0 | 39 |
| 23.9 | 28 |
| 24.2 | 34 |

In an embodiment, the invention refers to the polymorph P1 of the (R)-9-(2,5-difluorophenethyl)-4-ethyl-2-methyl-1-oxa-4,9-diazaspiro[5.5]undecan-3-one S(+)-mandelic salt, having the following XRPD pattern:

| Pos. [°2θ] | Rel. Int. [%] |
|---|---|
| 8.6 | 42 |
| 8.9 | 56 |
| 9.1 | 61 |
| 13.2 | 28 |
| 13.8 | 35 |
| 15.1 | 28 |
| 15.4 | 44 |
| 15.9 | 100 |
| 16.3 | 76 |
| 18.1 | 60 |
| 18.9 | 35 |
| 20.6 | 37 |
| 21.2 | 43 |
| 23.0 | 39 |
| 23.9 | 28 |
| 24.2 | 34 |

In an embodiment, the invention refers to the polymorph P1 of the (R)-9-(2,5-difluorophenethyl)-4-ethyl-2-methyl-1-oxa-4,9-diazaspiro[5.5]undecan-3-one S(+)-mandelic salt, having the following XRPD pattern:

| Pos. [°2θ] | Rel. Int. [%] |
|---|---|
| 8.6 | 42 |
| 8.9 | 56 |
| 9.1 | 61 |
| 13.8 | 35 |
| 15.4 | 44 |
| 15.9 | 100 |
| 16.3 | 76 |
| 18.1 | 60 |
| 18.9 | 35 |
| 20.6 | 37 |
| 21.2 | 43 |
| 23.0 | 39 |

In an embodiment, the invention refers to the polymorph P1 of the (R)-9-(2,5-difluorophenethyl)-4-ethyl-2-methyl-1-oxa-4,9-diazaspiro[5.5]undecan-3-one S(+)-mandelic salt, having the following XRPD pattern:

| Pos. [°2θ] | Rel. Int. [%] |
|---|---|
| 8.9 | 56 |
| 9.1 | 61 |
| 15.9 | 100 |
| 16.3 | 76 |
| 18.1 | 60 |

In an embodiment, the invention refers to the polymorph P1 of the (R)-9-(2,5-difluorophenethyl)-4-ethyl-2-methyl-1-oxa-4,9-diazaspiro[5.5]undecan-3-one S(+)-mandelic salt, having the following $^1$H-NMR (FIG. 53):

RMN-$^1$H (CD$_3$OD, 400 MHz, δ): 7.49-7.46 (m, 2H, ArH); 7.33-7.23 (m, 3H, ArH); 7.15-7.00 (m, 3H, ArH); 4.98 (s, 1H, CH); 4.19 (q, 1H, J=6.8 Hz, CH); 3.51-3.43 (m, 2H, CH$_2$); 3.40-3.33 (m, 2H, CH$_2$); 3.18-2.94 (m, 7H, CH$_2$); 2.26.-2.20 (m, 1H, CH$_2$); 1.95-1.88 (m, 1H, CH$_2$); 1.83-1.74 (m, 2H, CH$_2$); 1.39 (d, J=6.8 Hz, 3H, CH$_3$); 1.13 (t, J=7.2 Hz, 3H, CH$_3$).

In an embodiment, the invention refers to the polymorph P1 of the (R)-9-(2,5-difluorophenethyl)-4-ethyl-2-methyl-1-oxa-4,9-diazaspiro[5.5]undecan-3-one S(+)-mandelic salt, having an endothermic peak at 84.5° C. (FIG. 54).

In an embodiment, the invention refers to the polymorph P1 of the (R)-9-(2,5-difluorophenethyl)-4-ethyl-2-methyl-1-oxa-4,9-diazaspiro[5.5]undecan-3-one maleic salt.

In an embodiment, the invention refers to the polymorph P2 of the (R)-9-(2,5-difluorophenethyl)-4-ethyl-2-methyl-1-oxa-4,9-diazaspiro[5.5]undecan-3-one maleic salt.

In an embodiment, the invention refers to the polymorph P3 of the (R)-9-(2,5-difluorophenethyl)-4-ethyl-2-methyl-1-oxa-4,9-diazaspiro[5.5]undecan-3-one maleic salt.

EXPERIMENTAL PART

The following abbreviations are used:
ACN: acetonitrile
AcOH: acetic acid
AcOiBu: isobutyl acetate
aq.: aqueous
DCM: dichloromethane
DMSO: dimethylsulfoxide
Eq: equivalent
EtOAc: ethyl acetate
EtOH: ethanol
EX: example
h: hour/s
MeOH: methanol
MIK: methyl isobutyl ketone
Min: minutes
MTBE: methyl tert-butylether
IPA: isopropanol
rt: room temperature
Sat: saturated
Sol.: solution
THF: tetrahydrofuran
Analytical Techniques The following techniques have been used in this invention for characterize and identify either (R)-9-(2,5-difluorophenethyl)-4-ethyl-2-methyl-1-oxa-4,9-diazaspiro[5.5]undecan-3-one or its different salts:

XRPD

XRPD analysis was performed using a PANalytical X'Pert diffractometer with Cu Kα radiation in Bragg-Brentano geometry. The system is equipped with a monodimensional, real time multiple strip detector. Diffractograms were recorded from 3° to 40° (2θ) at a scan rate of 17.6° per minute.

DSC

DSC analyses were recorded with a Mettler Toledo DSC2. The samples were weighed into a 40 µL aluminum crucible with a pinhole lid and heated from 25 to 300° C. at a rate of 10° C./min, under nitrogen (50 mL/min).

Proton nuclear magnetic resonance ($^1$H-NMR) characterization $^1$H-NMR analyses were recorded in deuterated methanol (d4-CH$_3$OH) or chloroform (d-CHCl$_3$) in a Varian Mercury 400 spectrometer, equipped with a broadband probe ATB 1H/19F/X of 5 mm. Spectra were acquired dissolving 5-10 mg of sample in 0.7 mL of deuterated solvent.

Preliminary Miscibility Assays on (R)-9-(2,5-difluorophenethyl)-4-ethyl-2-methyl-1-oxa-4,9-diazaspiro[5.5]undecan-3-One Free Base In order to determine the most suitable solvents to be used, the miscibility of (R)-9-(2,5-difluorophenethyl)-4-ethyl-2-methyl-1-oxa-4,9-diazaspiro[5.5]undecan-3-one free base was studied in selected solvents (see Table 2). The number of volumes needed to "dissolve" the oil in the corresponding solvent at room temperature is reported in the table. In general, the oil is freely miscible with in all the solvents tested.

TABLE 2

Miscibility results of (R)-9-(2,5-difluorophenethyl)-4-ethyl-2-methyl-1-oxa-4,9-diazaspiro[5.5]undecan-3-one free base in different solvents

| Solvent | Miscibility |
|---|---|
| H$_2$O | 10 V |
| IPA | 10 V |
| MIK | 10 V |
| THF | 10 V |
| Toluene | 10 V | wherein MIK stands for methyl isobutyl ketone. IPA stands for isopropanol and THF stands for tetrahydrofuran.

Characterization ($^1$H NMR) of (R)-9-(2,5-difluorophenethyl)-4-ethyl-2-methyl-1-oxa-4,9-diazaspiro[5.5]undecan-3-one free base The free base obtained by chemical synthesis was obtained as an oil and was characterized by $^1$H nuclear magnetic resonance (FIG. 1).

Salt Formation

The acids used to investigate the salts of (R)-9-(2,5-difluorophenethyl)-4-ethyl-2-methyl-1-oxa-4,9-diazaspiro[5.5]undecan-3-one were selected according to the following criteria:

Acids with enough acidity to protonate the free base
Acids that are pharmaceutically acceptable compounds The pKa properties of the acids forming salts with (R)-9-(2,5-difluorophenethyl)-4-ethyl-2-methyl-1-oxa-4,9-diazaspiro[5.5]undecan-3-one are summarized in Table 3.

TABLE 3

Summary of the acidic counter-ions forming salts with (R)-9-(2,5-difluorophenethyl)-4-ethyl-2-methyl-1-oxa-4,9-diazaspiro[5.5]undecan-3-one

| Acid | pKa$_1$ | pKa$_2$ | pKa$_3$ |
|---|---|---|---|
| Hydrochloric acid | −7 | | |
| Fumaric acid | 3 | 4.4 | |
| Hydrobromic acid | −6 | | |
| Maleic acid | 3 | 4.4 | |
| Benzenesulfonic acid | 0.7 | | |
| Phosphoric acid | 2 | 7.1 | 12.3 |
| Sulfuric acid | −3 | 1.9 | |
| Succinic acid | 4.2 | 5.6 | |
| Oxalic acid | 1.3 | 4.3 | |
| Malonic acid | 2.8 | 5.7 | |
| Methanesulfonic acid | −1.2 | | |
| Ethanesulfonic acid | 2.1 | | |
| Nitric acid | −1.4 | | |
| (S)-(+)-Mandelic acid | 3.4 | | |

The general procedure to prepare the salts was as follows:

Grinding experiments: in a microtube of 2 mL, the free base and ca. 1 eq. of the corresponding acidic counter-ion were added. 1 drop of solvent and 2 stainless steel balls were added and the resulting mixture was ground in a ball mill (3×15 min, 30 Hz). The recovered solids were dried prior XRPD analysis.

Slurry, precipitation and evaporation experiments: in a microtube of 2 mL, the free base and ca. 1 eq. of the corresponding acidic counter-ion were mixed. Solvent was added to obtain a clear solution or a suspension:

When a suspension was obtained, the mixture was stirred at rt or 40° C. overnight.

When a clear solution was prepared, the solution was either cooled down to 0-5° C. or −20° C. to obtain a solid precipitated (precipitation) or evaporated to dryness under ambient conditions or with a rotavapor (evaporation).

In both situations, the recovered solids were isolated by centrifugation and dried prior XRPD analysis.

The results obtained (Table 4) indicate that (R)-9-(2,5-difluorophenethyl)-4-ethyl-2-methyl-1-oxa-4,9-diazaspiro[5.5]undecan-3-one forms salts with four classes of acids:

Inorganic acids: HCl, HBr, H$_3$PO$_4$, H$_2$SO$_4$ and nitric acid
Sulfonic acids: benzensulfonic, methanesulfonic and ethanesulfonic acid
Non substituted C1-C4 carboxylic di-acids: maleic, fumaric, oxalic, malonic and succinic acid
(S)-(+)-Mandelic acid.

TABLE 4

Experimental data of the salt formation experiments with ca. 1 eq. of acid.

| Acid | Solvent | Acid solution | Method | XRPD Result |
|---|---|---|---|---|
| Hydrochloric acid | water | aq. 1M HCl | Precipitation | P1 |
| | IPA | aq. 1M HCl | Slow evaporation | P2 |
| | MIK | aq. 1M HCl | Precipitation | P1 |
| | THF | aq. 1M HCl | Slow evaporation | P1 + P2 |
| | Toluene | aq. 1M HCl | Fast evaporation | P2 |
| | IPA | 1.25M HCl IPA | Precipitation | P1 |
| | DCM | 1.25M HCl IPA | Fast evaporation | P1 + 1 peak |
| | MeOH | 1.25M HCl MeOH | Fast evaporation | P1 |

TABLE 4-continued

Experimental data of the salt formation experiments with ca. 1 eq. of acid.

| Acid | Solvent | Acid solution | Method | XRPD Result |
|---|---|---|---|---|
| | Xylene | 1.25M HCl MeOH | Fast evaporation | P1 |
| | EtOH | 1.25M HCl EtOH | Precipitation | P1 |
| | TBME | 1.25M HCl EtOH | Precipitation | P1 |
| | Dioxane | 4M HCl Dioxane | Precipitation | P1 |
| | AcOEt | 4M HCl Dioxane | Precipitation | P1 |
| | AcOEt | 1.25M HCl MeOH | Slow evaporation | P1 |
| | Heptane | 1.25M HCl IPA | Precipitation | P1 |
| | Et$_2$O | aq. 1M HCl | Slow evaporation | P2 |
| | CHCl$_3$ | 1.25M HCl MeOH | Slow evaporation | P1 |
| | THF | 1.25M HCl EtOH | Precipitation | P1 |
| | DCM | 1.25M HCl IPA | Fast evaporation | P1 |
| | DCM | 1.25M HCl IPA | Fast evaporation | P1 |
| Fumaric acid | AcOiBu | — | Slurry | P1 |
| | MIK | — | Slurry | P1 |
| | Toluene | — | Slurry | P1 |
| | AcOiBu | — | Grinding | P1 |
| | DCM | — | Grinding | P1 |
| | MeOH | — | Slow evaporation | P1 |
| | THF | — | Slurry | P1 |
| | EtOH | — | Slurry | P1 |
| | THF | — | Slurry | P1 |
| | ACN | — | Slurry | P1 |
| | TBME | — | Slurry | P1 |
| | IPA | — | Crystallization | P1 |
| | Water | — | Crystallization | P1 |
| Hydrobromic acid | IPA | — | Precipitation | P1 |
| | MIK | — | Precipitation | P1 |
| | THF | — | Precipitation | P1 |
| | THF | — | Precipitation | P1 |
| | Water | — | Evaporation | P1 |
| Maleic acid | IPA | — | Precipitation | P1 |
| | MIK | — | Slurry | P2 |
| | Toluene | — | Slurry | P1 + P3 |
| | IPA | — | Precipitation | P3 |
| | MIK | — | Slurry | P2 |
| | Water | — | Evaporation | P1 + P2 |
| | THF | — | Evaporation | P1 + P3 |
| Benzenesulfonic acid | IPA | — | Precipitation | P1 |
| | MIK | — | Precipitation | P1 |
| | THF | — | Precipitation | P1 |
| | Toluene | — | Precipitation | P1 |
| | IPA | — | Precipitation | P1 |
| | Water | — | Evaporation | P1 + P2 |
| Phosphoric acid | IPA | — | Precipitation | P1 |
| | MIK | — | Precipitation | P1 |
| | THF | — | Precipitation | P1 |
| Sulfuric acid | IPA | — | Precipitation | P1 |
| | MIK | — | Precipitation | P1 |
| | THF | — | Precipitation | P1 |
| Succinic acid | IPA | — | Precipitation | P1 |
| | MIK | — | Slurry | P1 |
| | THF | — | Evaporation | P1 |
| | Toluene | — | Evaporation | P1 |
| Oxalic acid | Water | — | Precipitation | P2 |
| | IPA | — | Precipitation | P1 |
| | MIK | — | Precipitation | P2 |
| | THF | — | Precipitation | P1 |
| | Toluene | — | Slurry | P1 + P3 |
| Malonic acid | IPA | — | Precipitation | P1 |
| | MIK | — | Precipitation | P1 |
| | Toluene | — | Evaporation | NA |
| Methanesulfonic acid | Toluene | — | Precipitation | P1 |
| Ethanesulfonic acid | Toluene | — | Precipitation | P1 |
| | Water | — | Evaporation | P1 |
| | MIK | — | Evaporation | P1 |
| | THF | — | Evaporation | P1 |
| | MIK | — | Evaporation | P1 |
| Nitric acid | Water | — | Precipitation | P1 |
| | IPA | — | Precipitation | P1 |
| | MIK | — | Precipitation | P1 |
| | THF | — | Precipitation | P1 |
| | Toluene | — | Precipitation | P1 |

In addition, other experimental conditions were applied in two cases, as depicted in Table 5.

TABLE 5

Experimental data of salt preparation by special methodologies.

| Acid | Solvent | Experimental description | XRPD Result |
|---|---|---|---|
| Maleic acid | — | The previously obtained maleate salts (P2 and P3) were subjected to a thermal treatment (above solid-solid transition observed in DSC thermogram) and the solids were analyzed by XRPD. | P1 |
| Benzenesulfonic acid | Water | The solids obtained from the slow evaporation from a water solution were exposed to 90% RH and RT for 14 days. | P2 |

A summary of the results of the different salts obtained from (R)-9-(2,5-difluorophenethyl)-4-ethyl-2-methyl-1-oxa-4,9-diazaspiro[5.5]undecan-3-one, is shown in Table 6.

TABLE 6

Summary of the different salt forms obtained with (R)-9-(2,5-difluorophenethyl)-4-ethyl-2-methyl-1-oxa-4,9-diazaspiro[5.5]undecan-3-one.

| Acid Structure | Acid Name | Crystalline forms | Mp (° C.) by DSC |
|---|---|---|---|
| HBr | Hydrobromic acid | 1 Form | 245 |
| HCl | Hydrochloric acid | 3 Forms | 250 (P1) |
| HNO$_3$ | Nitric acid | 1 Form | 175 |
| H$_3$PO$_4$ | Phosphoric acid | 1 Form | 223 |
| H$_2$SO$_4$ | Sulfuric acid | 1 Form | 167 |
| PhSO$_3$H | Benzenesulfonic acid | 2 Forms | 169 (P1) |
| EtSO$_3$H | Ethanesulfonic acid | 1 Form | 124 |
| Cis-HOOC—CH=CH—COOH | Maleic acid | 3 Forms | 171 (P1) |
| Trans-HOOC—CH=CH—COOH | Fumaric acid | 1 Form | 196 |
| HOOC—CH$_2$—COOH | Malonic acid | 1 Form | 145 |
| HOOC—COOH | Oxalic acid | 2 Forms | 188 (P1) |
| HOOC—CH$_2$—CH$_2$—COOH | Succinic acid | 1 Form | 132 |
| O=C(O)C(O)Ph | (S)-(+)-Mandelic acid | 1 Form | 85 |

The invention claimed is:

1. A salt of (R)-9-(2,5-difluorophenethyl)-4-ethyl-2-methyl-1-oxa-4,9-diazaspiro[5.5]undecan-3-one, wherein the salt is selected from the group consisting of hydrochloride, fumarate, hydrobromide, maleate, phosphate, sulfate, succinate, oxalate, malonate, mesylate, esylate, besylate, nitrate and (S)-(+)-mandelate, and wherein the salt is in amorphous form or crystalline form.

2. The salt according to claim 1, which is selected from the group consisting of the polymorph P1, P2 or P3 of the hydrochloride salt, the polymorph P1 of the fumarate salt, the polymorph P1 of the hydrobromide salt, the polymorph P1, P2 or P3 of the maleate salt, the polymorph P1 of the phosphate salt, the polymorph P1 of the sulfate salt, the polymorph P1 of the succinate salt, the polymorph P1, P2 or P3 of the oxalate salt, the polymorph P1 of the malonate salt, the polymorph P1 of the mesylate salt, the polymorph P1 of the esylate salt, the polymorph P1 of the besylate salt, the polymorph P1 of the nitrate salt and the polymorph P1 of the (S)-(+)-mandelate salt.

3. A pharmaceutical composition comprising the salt according to claim 1.

4. A method for the treatment of a $\sigma_1$-receptor and/or $\mu$-opioid receptor mediated disease or condition in a subject in need thereof, comprising administration of the salt according to claim 1, wherein the disease or condition is pain.

5. The method according to claim 4, wherein the pain is medium to severe pain, visceral pain, chronic pain, cancer pain, migraine, inflammatory pain, acute pain or neuropathic pain, allodynia or hyperalgesia.

6. The method according to claim 5, wherein the pain is medium to severe pain, chronic pain, acute pain or neuropathic pain.

7. A pharmaceutical composition comprising the salt according to claim 2.

8. A method for the treatment of a $\sigma_1$-receptor and/or $\mu$-opioid receptor mediated disease or condition in a subject in need thereof, comprising administration of the salt according to claim 2, wherein the disease or condition is pain.

9. The method according to claim 8, wherein the pain is medium to severe pain, visceral pain, chronic pain, cancer pain, migraine, inflammatory pain, acute pain or neuropathic pain, allodynia or hyperalgesia.

10. The method according to claim 9, wherein the pain is medium to severe pain, chronic pain, acute pain or neuropathic pain.

* * * * *